United States Patent
Claure et al.

(10) Patent No.: US 6,512,938 B2
(45) Date of Patent: Jan. 28, 2003

(54) SYSTEM AND METHOD FOR CLOSED LOOP CONTROLLED INSPIRED OXYGEN CONCENTRATION

(76) Inventors: Nelson R. Claure, 11731 SW. 122nd Ave., Miami, FL (US) 33186; Eduardo H. Bancalari, 1925 Brickell Ave., Apt. D 808, Miami, FL (US) 33129

( * ) Notice: Subject to any disclaimer, the term of this patent is extended or adjusted under 35 U.S.C. 154(b) by 140 days.

(21) Appl. No.: 09/735,319

(22) Filed: Dec. 12, 2000

(65) Prior Publication Data

US 2002/0072659 A1 Jun. 13, 2002

(51) Int. Cl.[7] .................................................. A61B 5/00
(52) U.S. Cl. ......................................... 600/323; 600/322
(58) Field of Search .................................. 600/323, 322, 600/326, 328, 301; 128/204.22, 204.23, 204.21, 205.11

(56) References Cited

U.S. PATENT DOCUMENTS

| | | |
|---|---|---|
| 2,414,747 A | 1/1947 | Kirschbaum |
| 3,734,091 A | 5/1973 | Taplin |
| 4,121,578 A | 10/1978 | Torzala |
| 4,326,513 A | 4/1982 | Schulz et al. |
| 4,612,928 A | 9/1986 | Tiep et al. |
| 4,665,911 A | 5/1987 | Williams et al. |
| 4,671,297 A | 6/1987 | Schulze, Jr. |
| 4,869,253 A * | 9/1989 | Craig et al. .................. 600/323 |
| 4,889,116 A | 12/1989 | Taube |
| 4,932,402 A | 6/1990 | Snook et al. |
| 4,972,842 A | 11/1990 | Korten et al. |

(List continued on next page.)

FOREIGN PATENT DOCUMENTS

EP                 0658331 A1 *   6/1995

OTHER PUBLICATIONS

P.E. Morozoff & R.W. Evans. "Closed–Loop Control of Sao2 in the Neonate". (Biomedical Instrumentation & Technology 1992;26:117–123).*

(List continued on next page.)

*Primary Examiner*—Steven O. Douglas
*Assistant Examiner*—Khoa D. Huynh
(74) *Attorney, Agent, or Firm*—Stetina Brunda Garred & Brucker

(57) ABSTRACT

A system and method for delivering fractionally inspired oxygen ($FiO_2$) to a patient in response to receiving an arterial hemoglobin oxygen saturation signal ($SpO_2$) are disclosed. The $SpO_2$ is measured, for example, by using a pulse oximeter. An algorithm receives a signal indicating the $SpO_2$. The algorithm determines wither the $SpO_2$ is in the normoxemia range, hypoxemia range or hyperoxemia range. The algorithm also determines trends by calculating a slope of second-to-second changes in the $SpO_2$. Based on the current $SpO_2$ and the trend, the algorithm determines the appropriate $FiO_2$ for the patient and instructs a device, such as a mechanical ventilator or an air oxygen mixer as to the appropriate $FiO_2$ to be delivered to the patient. The system initializes various parameters with default values, but a user (e.g., a nurse) can also update the settings at any time. The system also provides alerts for various conditions, for example, standard pulse oximeter alarms, as well as notification when an episode of hyperoxemia or hypoxemia occurs, when it lasts for more than a specified period of time (e.g., two minutes) in spite of $FiO_2$ adjustments and when the adjustments set the $FiO_2$ at certain levels. The user is also alerted when $SpO_2$ signal is lost.

14 Claims, 39 Drawing Sheets

U.S. PATENT DOCUMENTS

| | | | |
|---|---|---|---|
| 4,986,268 A | | 1/1991 | Tehrani |
| 5,103,814 A | | 4/1992 | Maher |
| 5,119,815 A | * | 6/1992 | Chance |
| 5,251,632 A | * | 10/1993 | Delpy .................. 128/204.23 |
| 5,315,990 A | | 5/1994 | Mondry |
| 5,365,922 A | | 11/1994 | Raemer |
| 5,388,575 A | | 2/1995 | Taube |
| 5,560,352 A | * | 10/1996 | Heim et al. ............ 128/204.21 |
| 5,682,877 A | * | 11/1997 | Mondry ................. 128/204.22 |
| 5,752,509 A | * | 5/1998 | Lachmann et al. .... 128/204.23 |
| 6,035,223 A | * | 3/2000 | Baker, Jr. ................... 600/323 |
| 6,148,814 A | * | 11/2000 | Clemmer et al. |
| 6,192,260 B1 | * | 2/2001 | Chance ....................... 600/323 |
| 6,272,363 B1 | * | 8/2001 | Casciani et al. ............ 600/323 |
| 6,387,324 B1 | * | 5/2002 | Patterson et al. |

OTHER PUBLICATIONS

Thomas East et al. "Can Pulse Oximetry be Used to Reliably Predict Arterial Oxygenation". (Society of Critical Care Medicine Jan.–Feb. 1995; poster presentation).*

Vinod K. Bhutani et al. "Adpative Control of Inspired Oxygen Divery to the Neonate" (Pediatric Pulmonology 1992; 14:110–117).*

Fleur T. Tehrani. "A Mircocomputer Oxygen Control System for Ventilatory Therapy". (Annals of Biomedical Engineering 1992;vol. 20:547–558).*

Thomas P. Laubscher et al. "Automatic Selection of Tidal Volume, . . . for Close–Loo Controlled Ventilation". (International Journal of Clinical Monitoring and Computing 1994; 11:10–30).*

Robert Rudowski. "Lung Function . . . A Personal Computer–Based System".(Computer Methods and Program in Biomedicine 1990; 31:33–42).*

Michael Jastremski et al. "A Model for Technology Assessment as Applied to Closed Loop Infusion Systems". (Critical Care Medicine Oct. 1995; vol. 23:1–18).*

F. Lemaire & Alain Hart. "A Knowledge–Based System for Assisted Ventilation of Patients in ICU". (International Journal of Clinical Monitoring and Computing 1992; 9:239–250).*

Dwayne R. Westenskow. "Automating Patient Care with Closed–Loop Control". (Images, Signals and Devices 1986; vol. 3, No. 2, pp. 14–20).*

M. Blasovszky et al. "Improving Instrumentation for Hospital Care of Neonates in Hungary". (IEEE Engineering In Medicine and Biology Mar.–Apr. 1998; pp. 59–65).*

Norbert Weiler et al. "Adaptive Lung Ventilation . . . Automatic Response to Transitions to and from One–Lung Ventilation". (Journal of Clinical Monitoring and Computing 1998; 14:245–252).*

Hillary Don. "Hypoxemia". pp. 62–63.*

James H. Strickland et al. "A Computer–Controlled Ventilator Weaning System". (Chest 1991; vol. 100:pp. 1096–1099).*

Suzanne M. Burns. "Weaning from Mechanical Ventilation: A Method for Assessment and Planning". (Clinical Issues Aug. 1991; vol. 2, No. 3, pp. 372–387).*

1999 Abstract Form from 1999 ALA/ATS International Conference (2 pages) with hard copy of Power Point presentation (22 pages) presented at American Thoracic Society–American Lung Association meeting in Apr. of 1999 in San Diego California and at the Society of Pediatric Research—American Academy of Pediatric meeting in May of 1999 in San Francisco, California. Abstract and documents apply to both meetings.

* cited by examiner

| Parameter | Default Value |
|---|---|
| Sampling/Update Rate | 1 Hz |
| SpO$_2$ OK High Limit | 100% |
| SpO$_2$ OK Low Limit | 20% |
| SpO$_2$ OK Time Min | 5 sec. |
| SpO$_2$ Out Time Min | 5 sec. |
| SpO$_2$ Time in High Norm Low Range Min | 3 sec. |
| SpO$_2$ Time to Zero Counters | 10 sec. |
| SpO$_2$ Norm Adjust Interval | 40 sec., 20 - 60 sec. |
| SpO$_2$ Norm Wean Interval | 45 sec. |
| SpO$_2$ Norm Base Calc Min Interval | 30 sec. |
| SpO$_2$ Normal Base | 94% |
| SpO$_2$ Slope High Limit | 5%/sec. |
| SpO$_2$ Slope Low Limit | -5%/sec. |
| SpO$_2$ High Wean Level | 30 sec. |
| SpO$_2$ Hight Adjust Interval | 30 sec., 20 - 60 sec. |
| SpO$_2$ Low Adjust Interval | 20 sec., 5 - 40 sec. |
| SpO$_2$ Low Alarm Limit | 60 sec. |
| FiO$_2$ Base High Limit | 60% |
| FiO$_2$ Base Calc Interval | 300 sec. |
| FiO$_2$ at Min for Base Calc Interval | 30 sec. |
| FiO$_2$ at Max for Base Calc Interval | 60 sec. |
| FiO$_2$ Max | 100% |

*Fig. 4*

| User Setting | Valid Range | Default Value |
|---|---|---|
| SpO$_2$ Target Range High Limit | 94 - 100% | 96% |
| SpO$_2$ Target Range Low Limit | 85 - 94% | 88% |
| FiO$_2$ Base | 21 - 60% | 30% |
| FiO$_2$ Backup | 21 - 100% | 40% |
| FiO$_2$ Min |  | 21% |
| FiO$_2$ Set | (same as FiO$_2$ Base on control start) | |
| Control Switch | ON or OFF | OFF |
| FiO$_2$ Base Calculation Switch | ON or OFF | OFF |

*Fig. 5*

SYSTEM AND METHOD FOR CLOSED LOOP CONTROLLED INSPIRED OXYGEN CONCENTRATION

CROSS-REFERENCE TO RELATED APPLICATIONS (Not Applicable)

STATEMENT RE: FEDERALLY SPONSORED RESEARCH/DEVELOPMENT (Not Applicable)

BACKGROUND OF THE INVENTION

The present invention relates generally to oxygen delivery systems and more particularly to a closed loop system and method for automatically delivering fractionally inspired oxygen ($FiO_2$).

Very low birth weight infants often present with episodes of hypoxemia. These episodes are detected by arterial oxygen saturation monitoring by pulse oximetry ($SpO_2$) and are usually assisted with a transient increase in the fraction of inspired oxygen ($FiO_2$).

Given the rapid onset and frequency at which most of these episodes of hypoxemia occur, maintaining $SpO_2$ within a normal range by manual $FiO_2$ adjustment during each episode is a difficult and time-consuming task. Nurses and respiratory therapists respond to high/low $SpO_2$ alarms. Under routine clinical conditions, the response time is variable and the $FiO_2$ adjustment is not well defined. This exposes the infants to periods of hypoxemia and hyperoxemia which may increase the risk of neonatal chronic lung disease and retinopathy of prematurity.

Thus, a need exists for a system that can automatically adjust $FiO_2$. Prior art systems exist which automatically adjusts $FiO_2$. Such systems have had positive results. However, existing systems fail to respond to rapid $SpO_2$ changes and require manual intervention. Thus, a need exists for an automated system for adjusting $FiO_2$ which will respond to rapid $SpO_2$ changes. The system should not require manual intervention, but should allow for manual intervention, if desired. The system should also allow for gradually weaning the $FiO_2$ as soon as an episode begins to resolve.

BRIEF SUMMARY OF THE INVENTION

In accordance with the present invention, a system is provided for delivering fractionally inspired oxygen ($FiO_2$) to a patient. The system includes a device, such as a pulse oximeter, for obtaining an arterial hemoglobin oxygen saturation signal ($SpO_2$). An algorithm uses the $SpO_2$ to determine the appropriate $FiO_2$ to deliver to the patient. The algorithm adjusts the $FiO_2$ level of an air-oxygen mixer of an oxygen delivery device, such as a mechanical ventilator.

In accordance with other aspects of the invention, $SpO_2$ levels, including a target (normoxemia) range, are defined. $SpO_2$ values above the normoxemia range are considered to be hyperoxemic and values below the normoxemia range are considered to be hypoxemic.

In accordance with further aspects of the invention, a determination is made as to whether the $SpO_2$ signal is a valid signal. If the $SpO_2$ signal is not a valid signal, the $FiO_2$ to be delivered to the patient is determined based on a backup value. If the $SpO_2$ signal is a valid signal and closed loop mode is not enabled, the $FiO_2$ to be delivered to the patient is determined based on a backup value. If the signal is valid and closed loop mode is enabled, the $FiO_2$ to be delivered to the patient is determined based on the current $SpO_2$ and the trend. The trend is determined by calculating a slope using previous $SpO_2$ values. The determined $FiO_2$ is then delivered to the patient, for example, using a ventilator or an air-oxygen gas mixer.

In accordance with still further aspects of the invention, a user interface is provided. The user interface displays status information. The user interface also displays alerts. The user interface can also be used to view and modify user settings/parameters.

BRIEF DESCRIPTION OF THE DRAWINGS

These, as well as other features of the present invention, will become more apparent upon reference to the drawings wherein:

FIG. 4 is a table of exemplary variables and defaults values used in the present invention;

FIG. 5 is a table of exemplary user settings and default values used in the present invention;

DETAILED DESCRIPTION OF THE INVENTION

Figure 1:
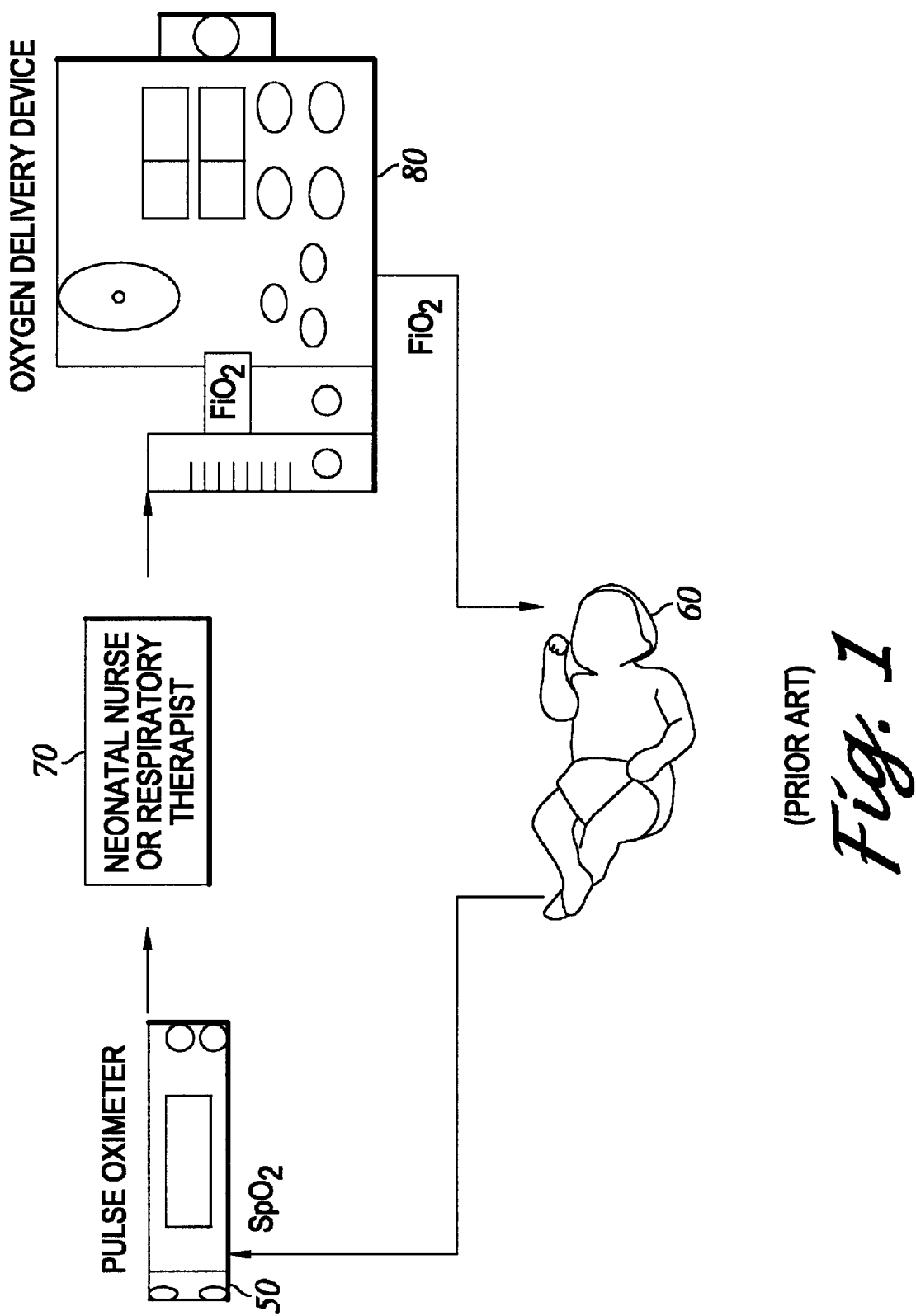
FIG. 1 is a block diagram of a prior art system for manually adjusting the fraction of inspired oxygen ($FiO_2$)

Traditionally, as shown in FIG. 1, a device, such as a pulse oximeter 50, is used to determine arterial hemoglobin oxygen saturation of a patient 60. A nurse 70 monitors the pulse oximeter 50. The nurse 70 adjusts the fractionally inspired oxygen ($FiO_2$) delivered to the patient 60 using a mechanical ventilator or air-oxygen mixer 80. Typically, ventilator device 80 mixes pure oxygen with air to give the patient a mixture of air having a percentage of oxygen. For example, a ventilator 80 may deliver a 90% oxygen/10% air mixture to the patient 60. The exact mixture of air required varies among patients and can vary for a given patient over a period of time. When a patient receives too much oxygen, a condition known as hyperoxemia occurs and if a patient does not receive enough oxygen, a condition known as hypoxemia occurs. "Normoxemia" occurs if the proper amount of oxygen is delivered (i.e., neither hyperoxemia nor hypoxemia occurs). A traditional system, such as the one shown in FIG. 1, is an "open system" because it requires human intervention (e.g., by a nurse 70).

Figure 2:
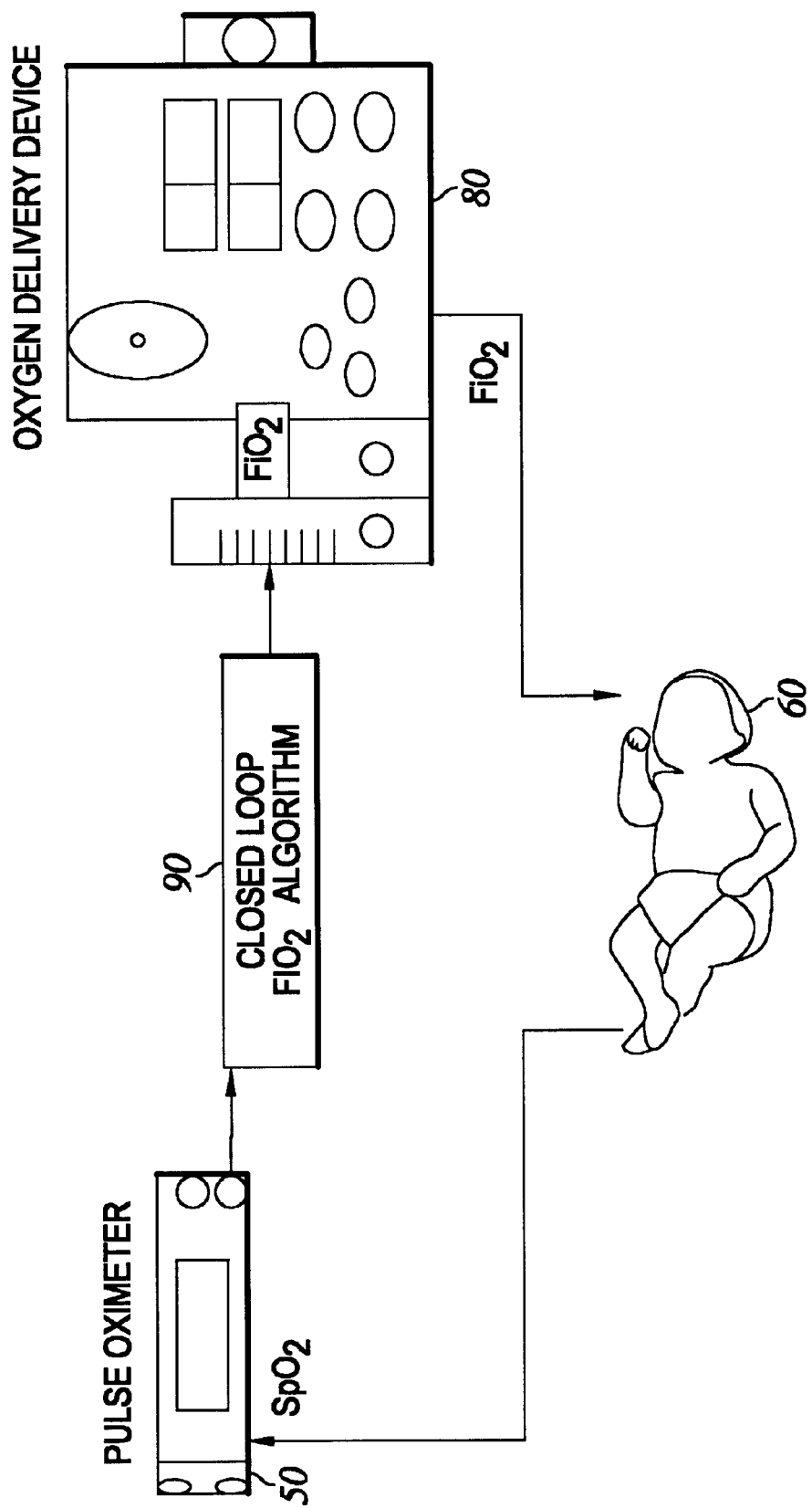
FIG. 2 is a block diagram of a system for automatically adjusting $FiO_2$ in accordance with the present invention.

As shown in FIG. 2, the present invention is a "closed system" which uses an algorithm 90 (described in detail below) to deliver $FiO_2$ in response to receiving an arterial hemoglobin oxygen saturation signal ($SpO_2$). In exemplary embodiments of the invention, the algorithm acquires information on arterial oxygen-hemoglobin oxygen saturation ($SpO_2$) measured by a pulse oximeter 50 and uses this measurement as input to determine the adjustment required, if any, to the fractionally inspired oxygen concentration ($FiO_2$) delivered to a patient on a continuous basis via a ventilator 80. It will be appreciated that the algorithm described herein can be applied to various modes of oxygen delivery, for example, mechanical ventilators, oxy-hood, nasal cannulas, and/or Continuous Positive Airway Pressure (CPAP) systems or incubators. The delay between the new $FiO_2$ setting and the actual oxygen concentration change is important. In most oxygen delivery modes the delay is relatively short (e.g., less than 15 seconds). However, there are significantly longer delays in large hoods or incubators. The closed-loop control system of the present invention is capable of changing the inspired gas concentration fast enough to follow rapid and frequent hypoxemic episodes. In exemplary embodiments of the present invention, $SpO_2$ is read from the analog output of a pulse oximeter. However, alternative embodiments allow for reading from other outputs, e.g., from any serial output.

Even though the invention does not require human intervention, manual adjustments and overrides can be performed. The system described herein is ideally suited for patients who are very low birth weight infants. However, it will be appreciated that the present invention is not so limited. The invention can be used for patients of all ages.

The present invention includes an algorithm 90 that continuously acquires the patient's $SpO_2$ information and adjusts the $FiO_2$ delivered to the patient (e.g., via a mechanical ventilator 80) to maintain $SpO_2$ within a specific range set by a user (e.g., a nurse). In exemplary embodiments, the algorithm 90 calculates and adjusts the $FiO_2$ once per second on a "closed loop" basis using a direct electronic interface between the algorithm 90 and the ventilator's air-oxygen blender control.

The algorithm 90 defines $SpO_2$ ranges based on a user-defined target range of normoxemia. Hyperoxemia is assumed to occur when $SpO_2$ exceeds the normoxemia target range and hypoxemia is assumed to occur when $SpO_2$ falls below the normoxemia target range. The differential control feedback functions are used to deal with the patient variability changes in $FiO_2$ which in combination with the algorithm's rules modulate the magnitude and timing of $FiO_2$ adjustments during periods of normoxemia or during a hypoxemic or hyperoxemic episode. The factors used to determine the adjustments are the current $SpO_2$ level, direction and rate of $SpO_2$ change, degree and duration of the hypoxemic or hyperoxemic episode, current $FiO_2$ setting, and the individual patient's basal $FiO_2$ requirement during normoxemia.

$FiO_2$ adjustments during hyperoxemia and normoxemia are of smaller magnitude and slower pace than those occurring during hypoxemia. However, the rules and control functions in the algorithm are designed to enable the algorithm to modify its responses to changing conditions, from slow and subtle $SpO_2$ changes during periods of stability to rapidly falling $SpO_2$ during an acute period of hypoxemia.

The algorithm 90 also has a backup function in the event that there is missing $SpO_2$ information. The backup function locks the $FiO_2$ after a short wait period at a backup level preset by the user or at the current $FiO_2$ level, whichever is higher until $SpO_2$ information is available again.

In addition to the standard pulse oximeter alarms, the algorithm alerts the user when an episode of hyperoxemia or hypoxemia occurs, when it lasts for more than a specified period of time (e.g., two minutes) in spite of $FiO_2$ adjustments, and when the adjustments set the $FiO_2$ at certain levels for example, a low level of 0.21 (room air) and a high level of 1.0 (pure oxygen). The user is also alerted when $SpO_2$ signal is lost. These alerts are intended to notify the user (e.g., nurse) to verify proper function of the $SpO_2$ measurement, $FiO_2$ delivery and communication links.

Figure 3:
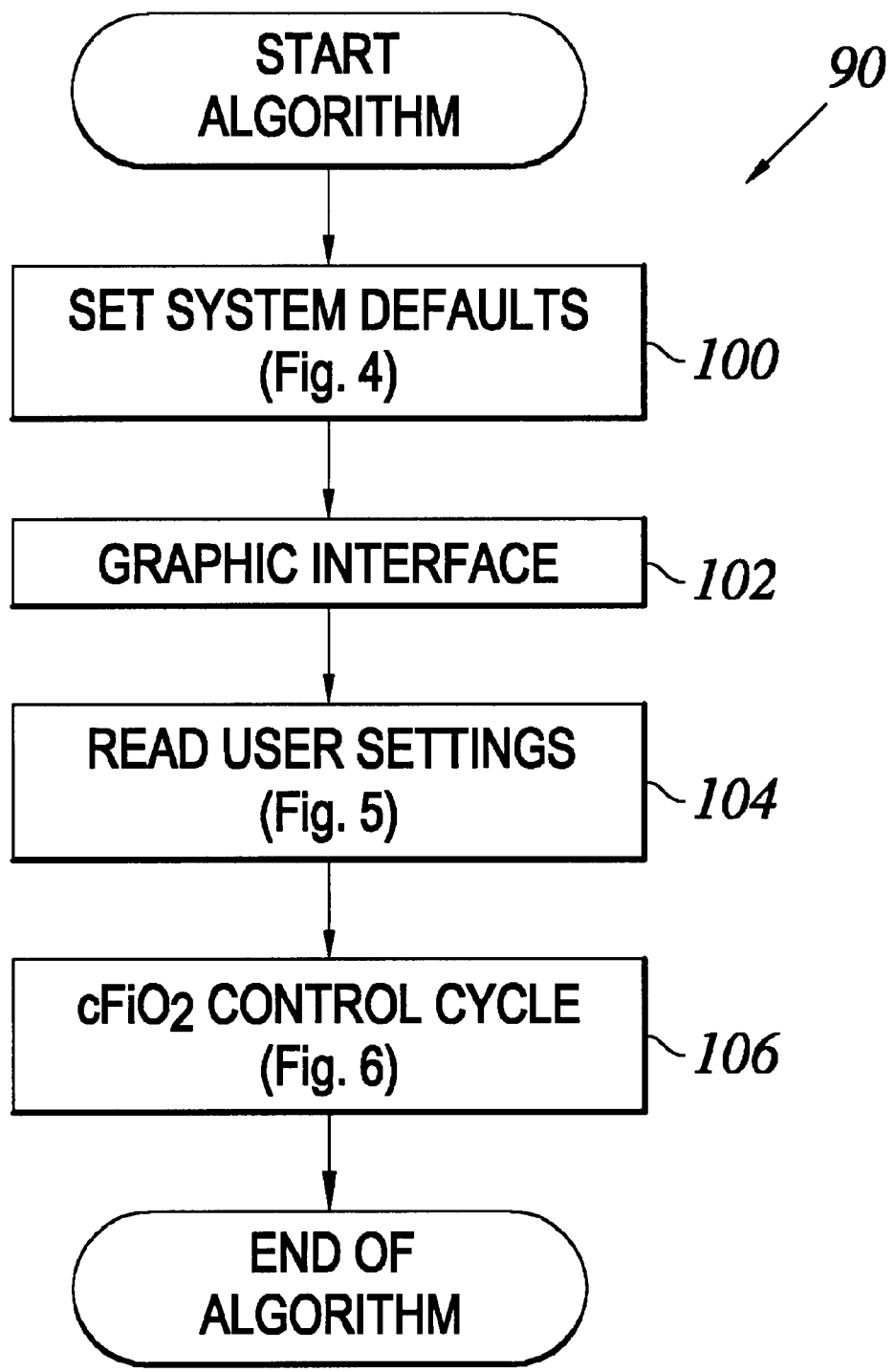
FIG. 3 is a flow diagram illustrating exemplary logic for automatically adjusting $FiO_2$ in accordance with the present invention.

FIG. 3 is a flow diagram illustrating exemplary logic performed by algorithm 90. The algorithm classifies $SpO_2$ according to ranges set by the user. The user sets a target range for normoxemia (e.g., an exemplary default range is 88%–96%). An $SpO_2$ above the range for normoxemia (e.g., greater than 96%) is considered hyperoxemic. An $SpO_2$ below the range for normoxemia (e.g., less than 88%) is considered hypoxemic. Because of its importance, hypoxemia is further subdivided. In exemplary embodiments, hypoxemia is further subdivided into the following ranges: less than 75%; 75–85%; and 85% to the low limit of the target range, (for example, using the exemplary default range, 85%–88%). $FiO_2$ is adjusted based on the current $SpO_2$, the $SpO_2$ trend and the time that $SpO_2$ has been within the range, as well as basal and current $FiO_2$ settings.

The logic of FIG. 3 moves from a start block to block 100 where system defaults are set. Various system defaults or parameters, such as those shown in the table of FIG. 4 are preset. The parameters (variables) in Table 4 are described in further detail later. These variables can be modified by the application and/or by the user.

Figure 21:
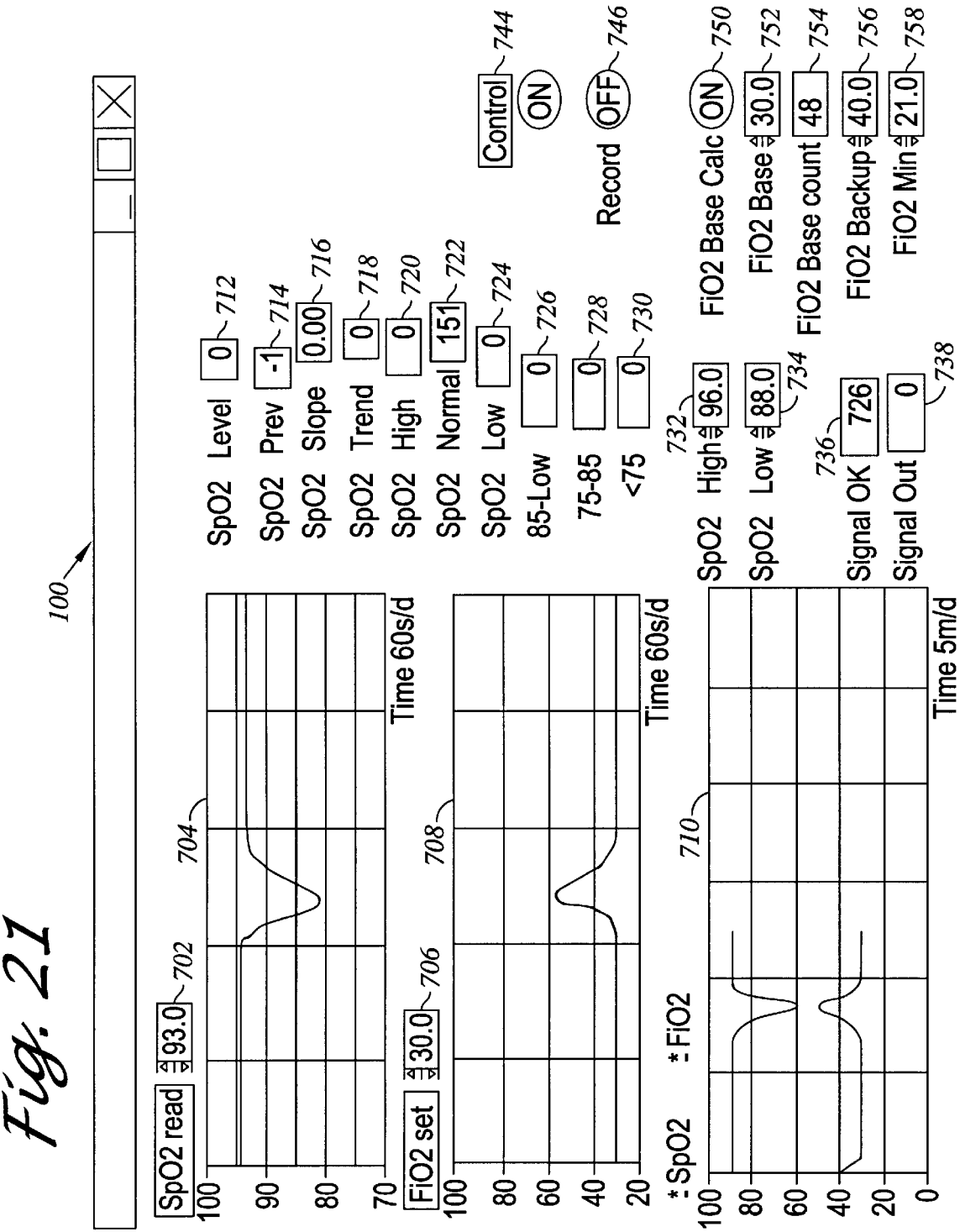
FIG. 21 is an exemplary graphical user interface illustrating $SpO_2$ and $FiO_2$ values over a specified period of time.

After system defaults are set, the logic of FIG. 3 moves to block 102 where a user interface is displayed. An exemplary user interface is illustrated in FIG. 21 and described later.

The logic of FIG. 3 then moves to block 104 where user settings are read. User settings, such as those shown in FIG. 5, should be set prior to commencement of the closed loop execution (i.e., prior to entering the control cycle). Preferably, the settings can also be set or modified during execution of the algorithm. Preferably, a suitable user interface (such as the one shown in FIG. 21) is provided to allow the user to set/modify these values. Although the user can set/modify these values, preferably system defaults (such as those shown in FIG. 5) are provided.

In exemplary embodiments of the invention $SpO_2$ Target Range High Limit and $SpO_2$ Target Range Low Limit define the patient's desired target range. In the exemplary embodiment shown in FIG. 5, $SpO_2$ Target Range Low Limit must be in the range between 85%–94% and has a default value of 88% and $SpO_2$ Target Range High Limit must be in the range between 94%–100% and has a default value of 96%. Thus, the default target range is 88%–96%.

$FiO_2$ Base is the patient's basal oxygen requirement to maintain normal $SpO_2$. $FiO_2$ Base can be kept fixed at the user setting or automatically adjusted by the algorithm to changes in the basal oxygen needs. $FiO_2$ Base is also the initial level for $FiO_2$ Set when closed loop is switched ON. The default setting for $FiO_2$ Base can alternatively be obtained from the user setting during manual (normal) mode used before closed loop is ON. In the exemplary embodiment shown in FIG. 5, $FiO_2$ Base must be in the range between 21%–60% and has a default value of 30%.

$FiO_2$ Backup is the default value for $FiO_2$ Set when the system is started, when $SpO_2$ Signal is OUT or when closed-loop switch is OFF. $FiO_2$ Backup should not be lower than the basal ($FiO_2$ Base). In the exemplary embodiment shown in FIG. 5, $FiO_2$ Backup must be in the range between 21%–100% and has a default value of 40%.

$FiO_2$ Min is the minimum level at which $FiO_2$ Set, $FiO_2$ Base and $FiO_2$ Backup can be set. In the exemplary embodiment shown in FIG. 5, $FiO_2$ Min has a default value of 21% (room air).

$FiO_2$ Max (not shown in FIG. 5) is a default parameter. For example, $FiO_2$ Max is initially set at a default of 100% (pure oxygen), but can be user selectable.

Figure 6:
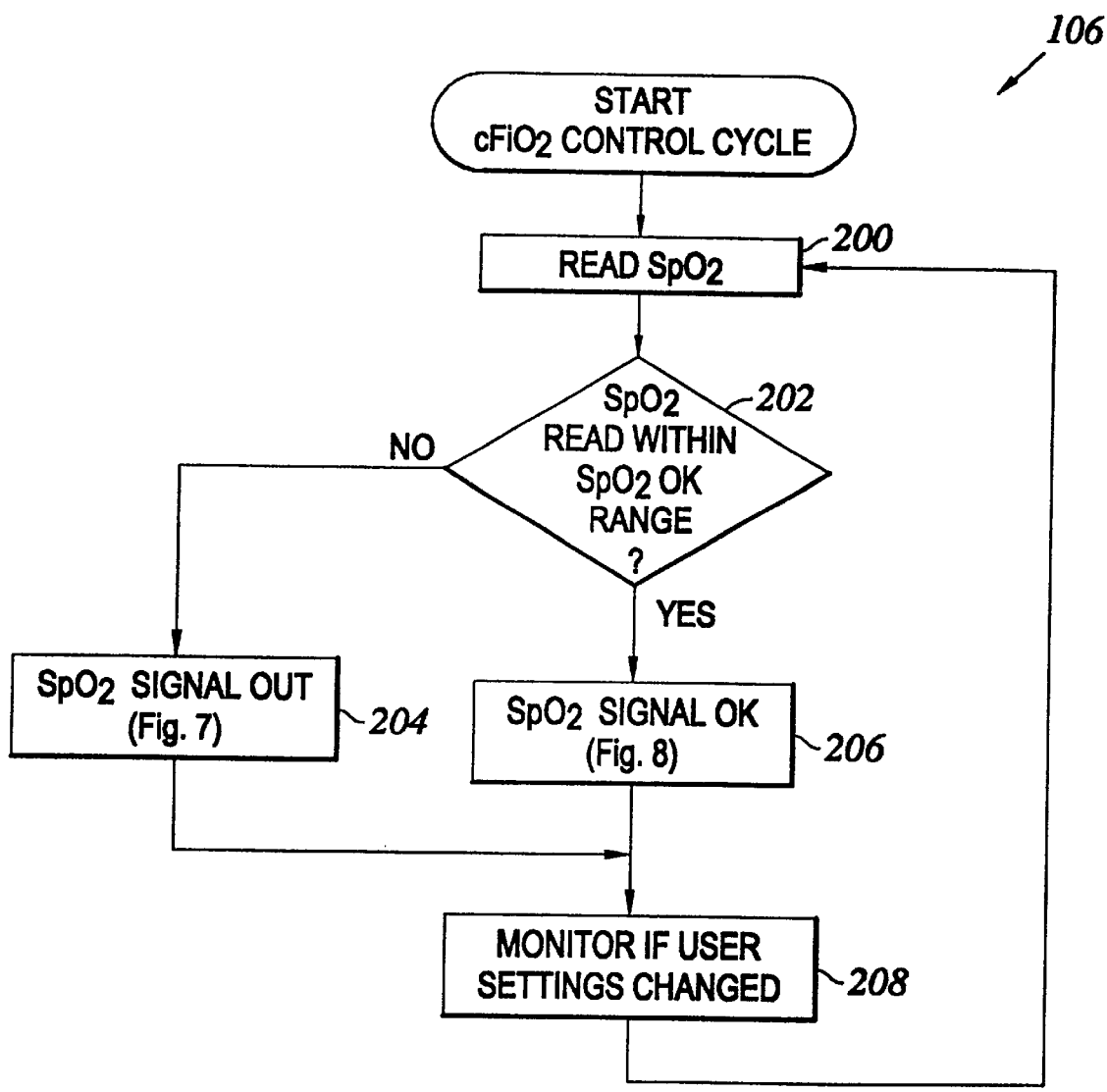
FIG. 6 is flow diagram illustrating exemplary logic for performing a control cycle as shown in FIG. 3.

After the user settings are read, the logic of FIG. 3 proceeds to block 106 where a control cycle is performed as shown in FIG. 6 and described in detail next. The control cycle is initiated when the user switches closed-loop to ON. If closed-loop is set to OFF, the control cycle loop continues, but $FiO_2$ Set is returned to the $FiO_2$ Backup level. $FiO_2$ Set is the actual parameter set at the air-oxygen mixer.

Figure 7A:
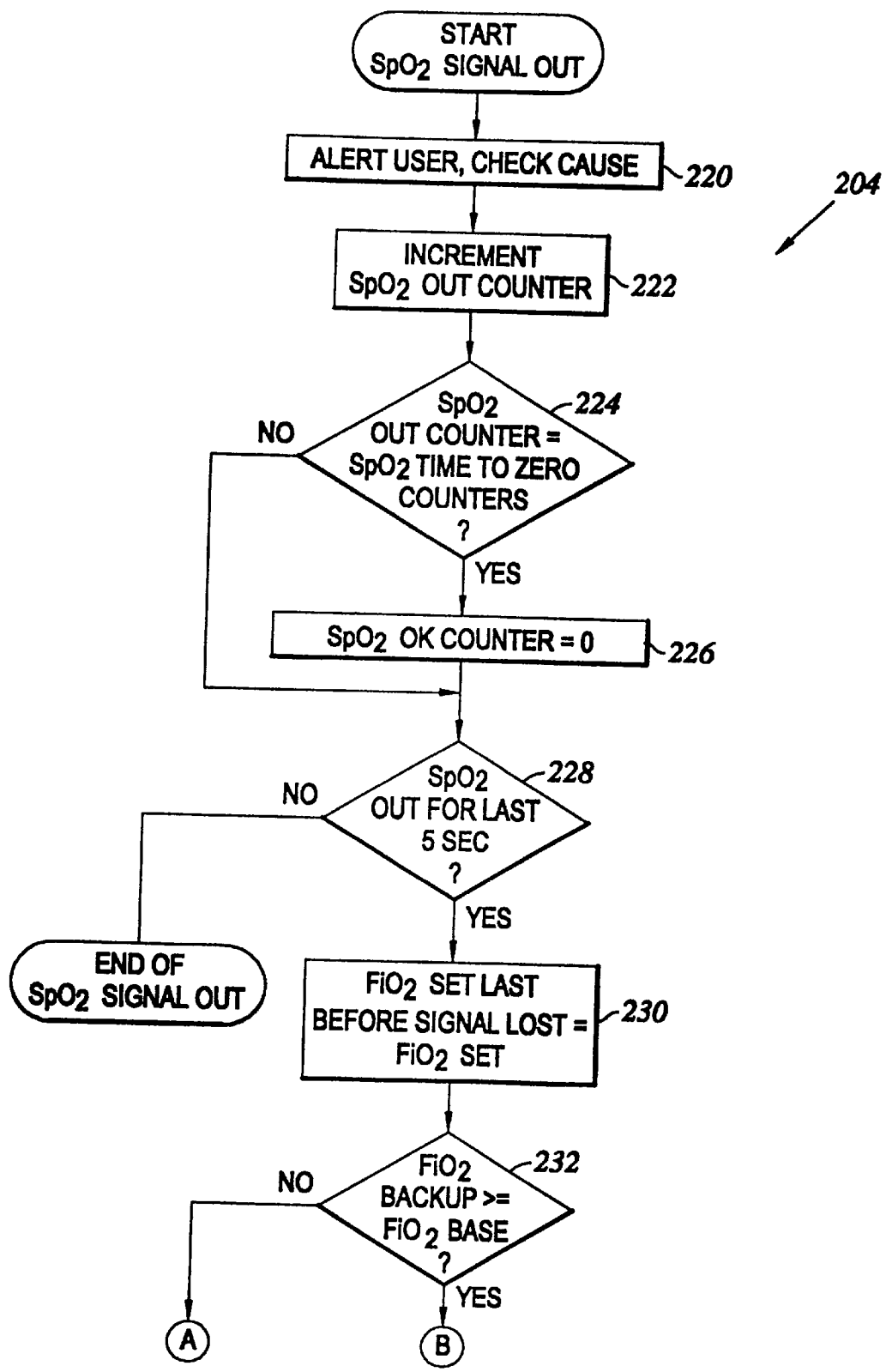
FIG. 7 is a flow diagram illustrating exemplary logic for performing backup processing when a valid $SpO_2$ signal is not received as shown in FIG. 6.
Figure 7B:
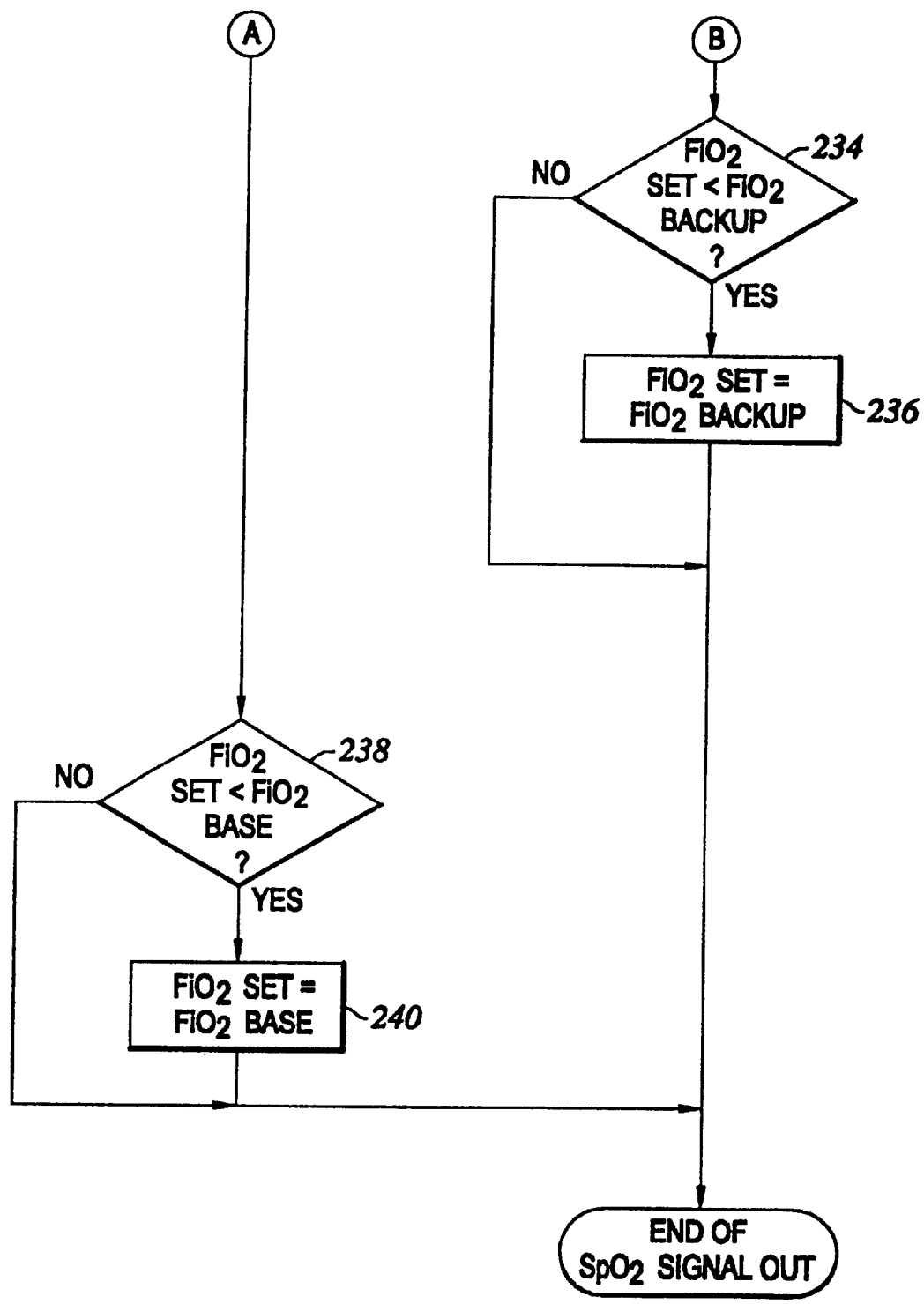

FIG. 6 is a flow diagram illustrating exemplary logic for performing a control cycle in accordance with the present invention. The logic moves from a start block to block 200 where $SpO_2$ (e.g., $SpO_2$ output signal from pulse oximeter 50) is read. The $SpO_2$ that is read is stored as $SpO_2$ Read. Next, the logic moves to decision block 202 where a test is made to determine if $SpO_2$ Read is within the acceptable $SpO_2$ range. For example, as shown in FIG. 4, in exemplary embodiments, the default range is between 20 and 100%. If $SpO_2$ Read is not within the acceptable range (no in decision block 202), the logic moves to block 204 where $SpO_2$ signal OUT processing is performed as shown in FIG. 7 and described below. Most oximeters provide a 0% reading when signal is OUT when communication between the oximeter and algorithm is by means of the analog output of the pulse oximeter. Alternatively, if serial communication exists between the oximeter and the algorithm, $SpO_2$ information can be monitored by proper communication handshake. If $SpO_2$ is within the $SpO_2$ OK range (yes in decision block 202), the logic moves to block 206 where $SpO_2$ Signal OK processing is performed as shown in detail in FIG. 8 and described later. After $SpO_2$ signal OUT processing has been performed (block 204) or $SpO_2$ OK processing has been performed (block 206), the logic moves to block 208 to monitor whether user settings have been changed. Preferably, the user can change various settings at any time. If user settings have been changed, variables are updated accordingly. The logic then returns to block 200 where $SpO_2$ is read and processed again. In exemplary embodiments, $SpO_2$ is read and processed (e.g., $FiO_2$ adjusted accordingly) every second. Thus, the $SpO_2$ is continuously monitored every second until the system is shut off.

FIG. 7 illustrates exemplary logic for performing $SpO_2$ Signal OUT (e.g., backup mode) processing in accordance with the present invention. In backup mode processing, $FiO_2$ Set (i.e., the actual parameter set at the air-oxygen mixer) is locked at the $FiO_2$ Backup level, at the $FiO_2$ Base level or at the current level (whichever is higher) until feedback information is available again.

The logic of FIG. 7 moves from a start block to block 220 where the user is alerted and the cause is checked. There are various reason why a pulse oximeter may fail to provide information, for example, poor signal quality during motion or low perfusion (or both), a loose probe or a probe no longer in place, or a break on the communication link between the oximeter and the algorithm 90. Next, the logic moves to block 222 where $SpO_2$ Out Counter is incremented. $SpO_2$ Out Counter is used to confirm that signal loss is not related to some type of temporary variability or error. Only after a minimum interval has passed is $SpO_2$ Signal OK Counter reset. This allows activities to resume normally if there was a short drop-out period. Next, the logic moves to decision block 224 where a test is made to determine if $SpO_2$ Out Counter is equal to $SpO_2$ Time to Zero Counters. If so, the logic moves to block 226 where $SpO_2$ OK Counter is set to zero. For example, in the exemplary embodiment shown in FIG. 4, the default value is ten seconds. Thus, if $SpO_2$ Out Counter is equal to ten, $SpO_2$ OK Counter will be reset to zero. The illustrated embodiment assumes that $SpO_2$ is read and processed once a second. However, it will be appreciated that the algorithm can be modified to accommodate reading and processing $SpO_2$ values at a different interval.

Next, the logic moves to decision block 228 where a test is made to determine if $SpO_2$ Out Counter has been set for the last five seconds (e.g., $SpO_2$ Out Counter is greater than or equal to five). While the logic illustrated is based on a lost $SpO_2$ signal for five consecutive seconds, it will be appreciated that other time periods can be used. Preferably, the default value can be modified by the user. A short wait will provide early additional oxygen if hypoxemia is accompanied by motion of the extremities (which is often observed), whereas a longer wait will generally apply to cases where hypoxemia is not frequent and signal loss is not accompanied by hypoxemia. If $SpO_2$ has not been set for the specified period of time (e.g., five seconds), the logic of FIG. 7 ends.

If, however, $SpO_2$ has been lost (OUT) for the last five seconds or other specified period of time (yes in decision block 228), the logic moves to block 230 where $FiO_2$ Set Last Before Signal Lost is set to $FiO_2$ Set. When $FiO_2$ is set to the backup level, the algorithm stores the last $FiO_2$ value in memory. This $FiO_2$ Set Last Before Signal Lost value is used under some conditions to set $FiO_2$ as soon as $SpO_2$ is available again. Next, the logic moves to decision block 232 where a test is made to determine if $FiO_2$ Backup is greater than or equal to $FiO_2$ Base. If so, the logic moves to decision block 234 where a test is made to determine if $FiO_2$ Set is less than $FiO_2$ Backup. If so, the logic moves to block 236 where $FiO_2$ Set is set to $FiO_2$ Backup. The logic of FIG. 7 then ends and processing returns to FIG. 6.

If $FiO_2$ Backup is less than $FiO_2$ Base (no in decision block 232), the logic moves to decision block 238 where a test is made to determine if $FiO_2$ Set is less than $FiO_2$ Base. If so, the logic moves to block 240 where $FiO_2$ Set is set to $FiO_2$ Base. If not, $FiO_2$ set does not get changed. The logic of FIG. 7 then ends and processing returns to FIG. 6.

Figure 8A:
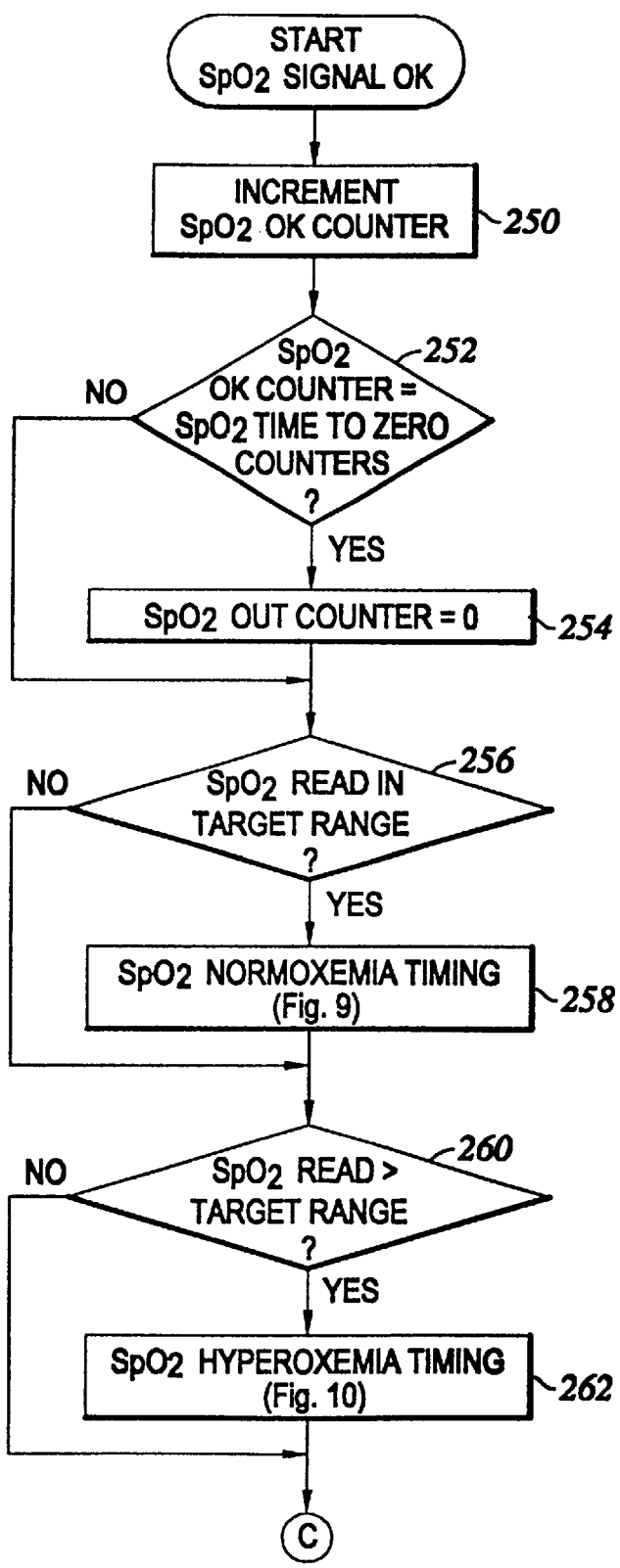
FIGS. 8–20 are a flow diagram illustrating exemplary logic for processing a valid $SpO_2$ signal as shown in FIG. 6.
Figure 8B:
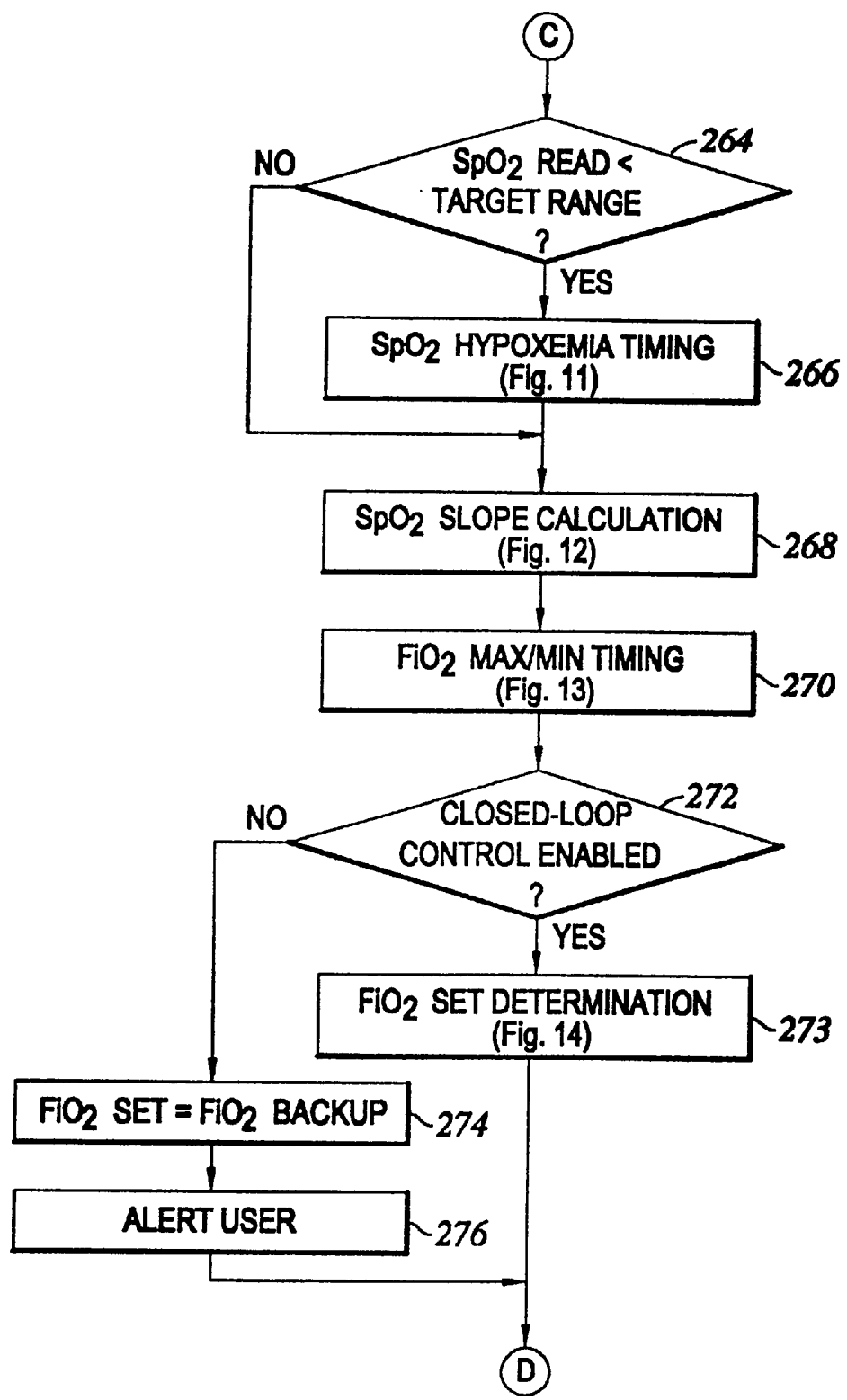
Figure 8C:
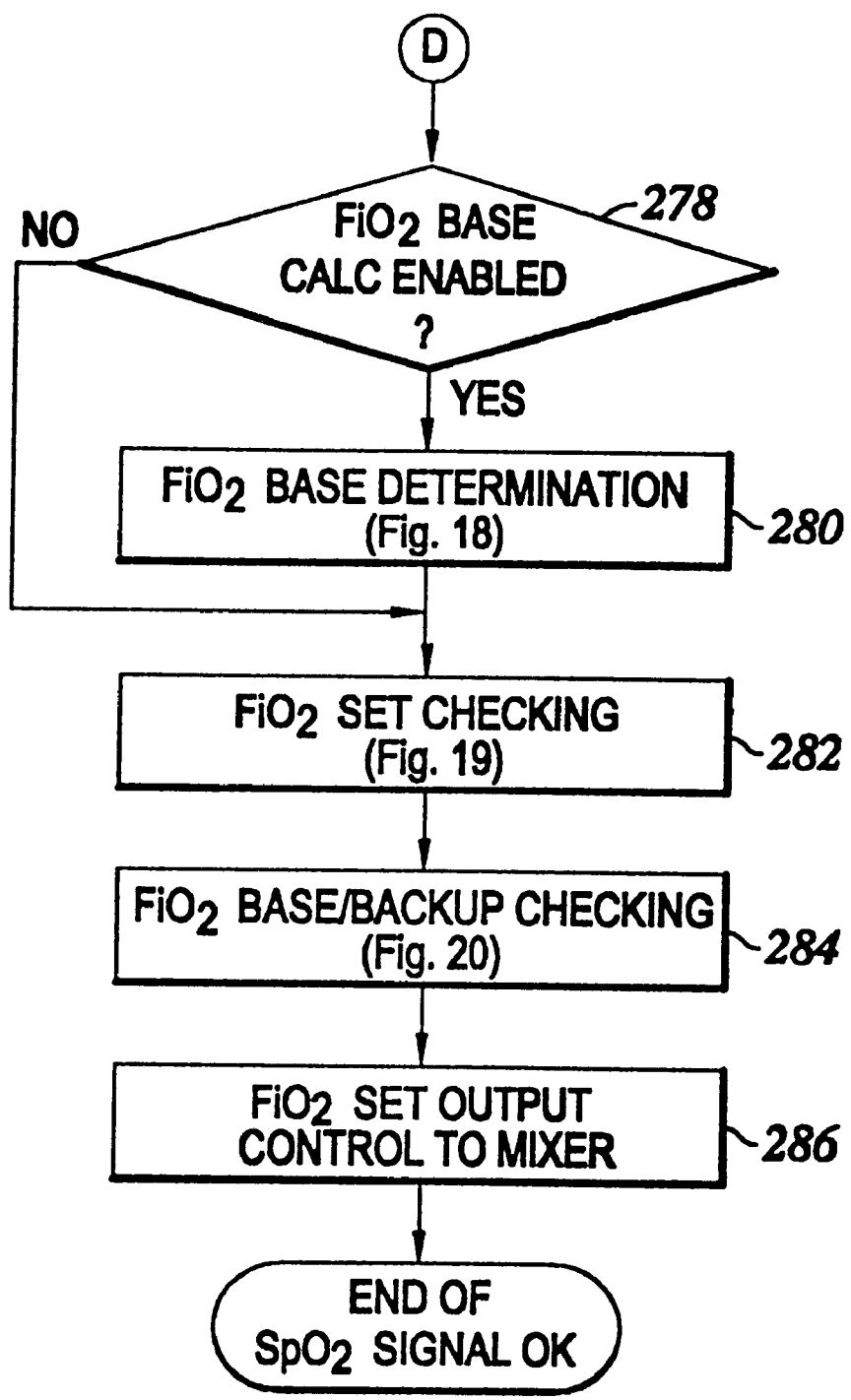

FIG. 8 illustrates exemplary logic for performing $SpO_2$ Signal OK processing in accordance with the present invention. The counters of time spent with $SpO_2$ within each range are updated continuously. These counters are used to classify and confirm the actual $SpO_2$ level (normoxemia, hyperoxemia or hypoxemia) and discriminate against short variability. Only after a minimum time has elapsed since $SpO_2$ has reached any specific range is it considered to be a new $SpO_2$ level. In the exemplary embodiment illustrated in FIG. 4, the default time period before being considered a new level defaults to three seconds ($SpO_2$ Time in High Norm Low Range Min). This short interval can be affected by short variability, therefore, other counters for previous $SpO_2$ ranges are reset only after a longer interval ($SpO_2$ Time to Zero Counters, which defaults to ten seconds in the exemplary embodiment shown in FIG. 4) has elapsed. In this way, $SpO_2$ Read is confirmed to be out of any specific range only after the longer time period (e.g., ten seconds). $SpO_2$ Read is confirmed to be in the new range after three seconds (or whatever value $SpO_2$ Time in High Norm Low Range Min is set to) but it is confirmed to be out of the previous range only after ten seconds (or whatever value Time to Zero Counters is set to). In this way, if $SpO_2$ Read returns shortly after to the previous range, all activities in that range will resume immediately.

The logic of FIG. 8 moves from a start block to block 250 where $SpO_2$ OK Counter is incremented. Next, the logic moves to decision block 252 where a test is made to determine if $SpO_2$ OK Counter is equal to $SpO_2$ Time to Zero Counters. If so, the logic moves to block 254 where $SpO_2$ Out Counter is set to zero. Next, appropriate timing processing is performed based on $SpO_2$ Read. If $SpO_2$ Read is in the target range for normoxemia, for example, 88%–96%, (yes in decision block 256), the logic moves to block 258 where normoxemia timing is performed as shown in detail in FIG. 9 and described next.

Figure 9:
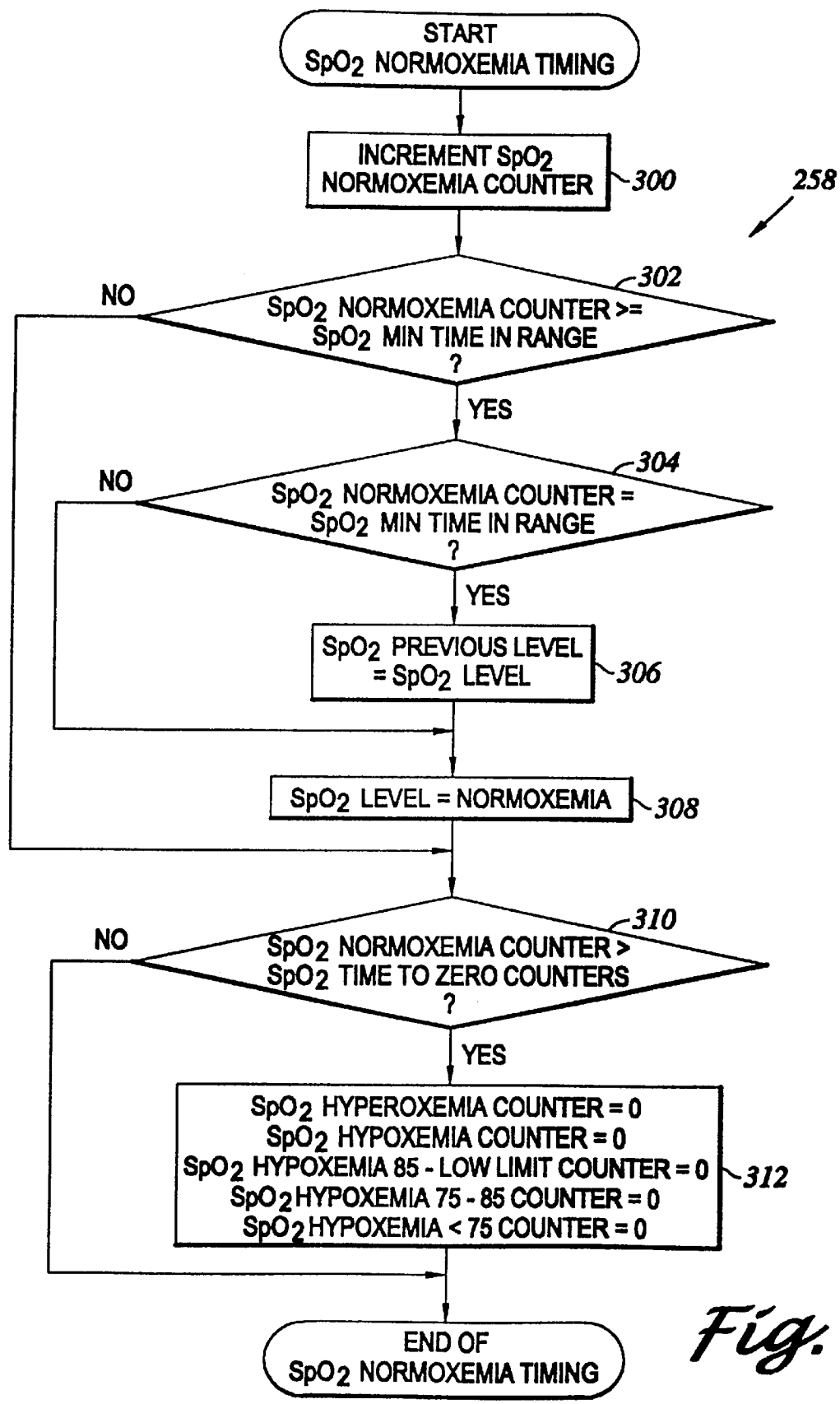

FIG. 9 illustrates exemplary logic for performing normoxemia timing in accordance with the present invention. As shown in FIG. 9, and described below, normoxemia is considered the new $SpO_2$ level only after a specified period of time (e.g., three seconds) has elapsed since $SpO_2$ entered the target range, however, counters for other $SpO_2$ ranges are reset only after a longer interval (e.g., ten seconds) has elapsed. The logic of FIG. 9 moves from a start block to block 300 where $SpO_2$ Normoxemia Counter is incremented. Next, the logic moves to decision block 302 where a test is made to determine if $SpO_2$ Normoxemia Counter is greater than or equal to $SpO_2$ Min Time in Range ($SpO_2$ Time in High Norm Low Range, e.g., three seconds). If so, the logic moves to decision block 304 where a test is made to determine if $SpO_2$ Normoxemia Counter is equal to $SpO_2$ Min Time in Range. If so, the logic moves to block 306 where $SpO_2$ Previous Level is set to $SpO_2$ Level. Regardless of the outcome of decision block 304, the logic proceeds to block 308 where $SpO_2$ Level is set to Normoxemia. Regardless of the outcome of decision block 302, the logic moves to decision block 310 where a test is made to determine if $SpO_2$ Normoxemia Counter is greater than $SpO_2$ Time to Zero Counters. If so, the logic moves to block 312 where counters ($SpO_2$ Hyperoxemia Counter, $SpO_2$ Hypoxemia Counter, $SpO_2$ Hypoxemia 85-Low Limit Counter, $SpO_2$ Hypoxemia 75–85 Counter and $SpO_2$ Hypoxemia less than 75 Counter) are set to zero. The logic of FIG. 9 then ends and processing returns to FIG. 8.

Returning to FIG. 8, if $SpO_2$ Read is greater than the target range (yes in decision block 260), the logic moves to block 262 where hyperoxemia timing is performed as shown in detail in FIG. 10 and described next.

Figure 10:
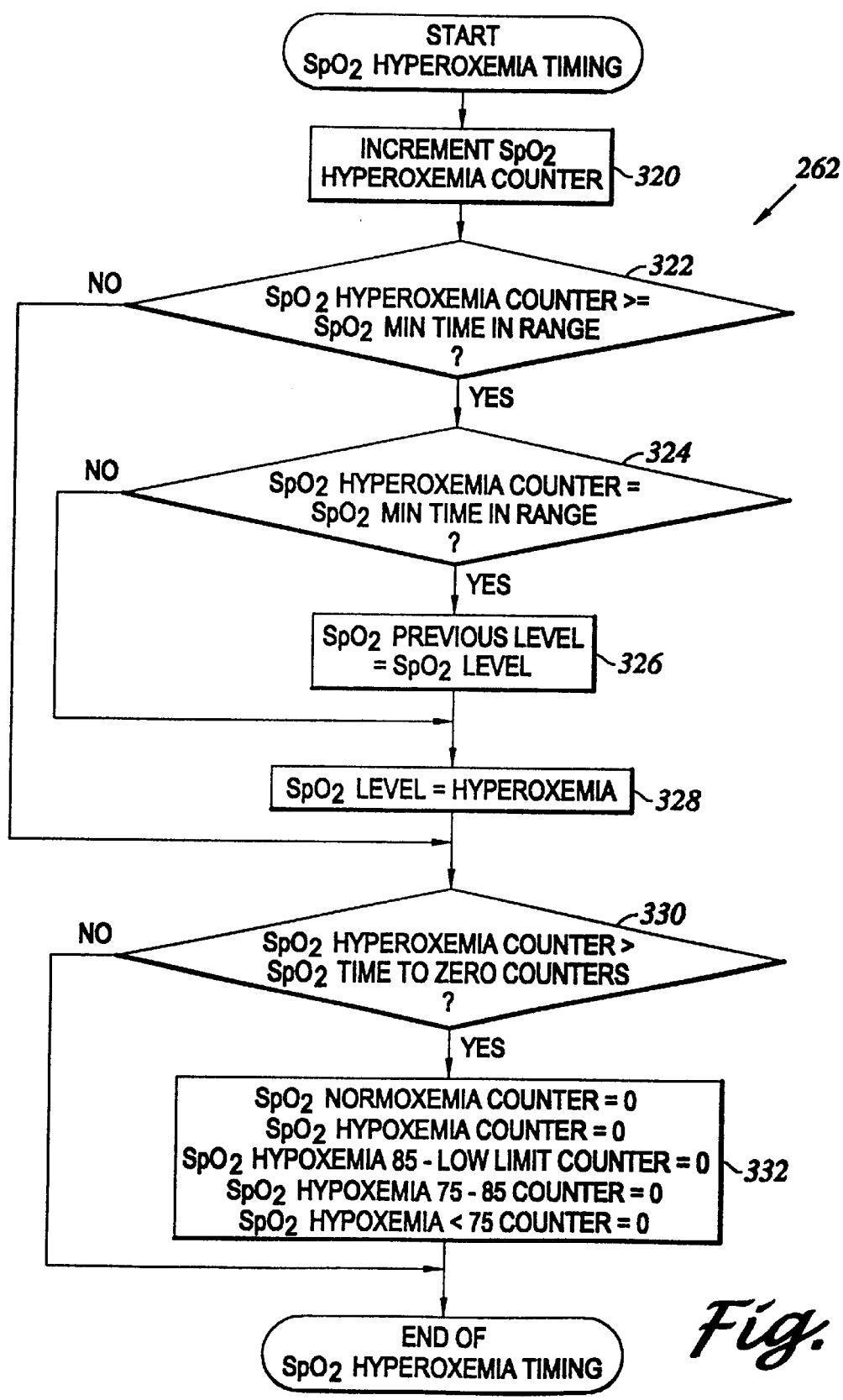
Figure 11A:
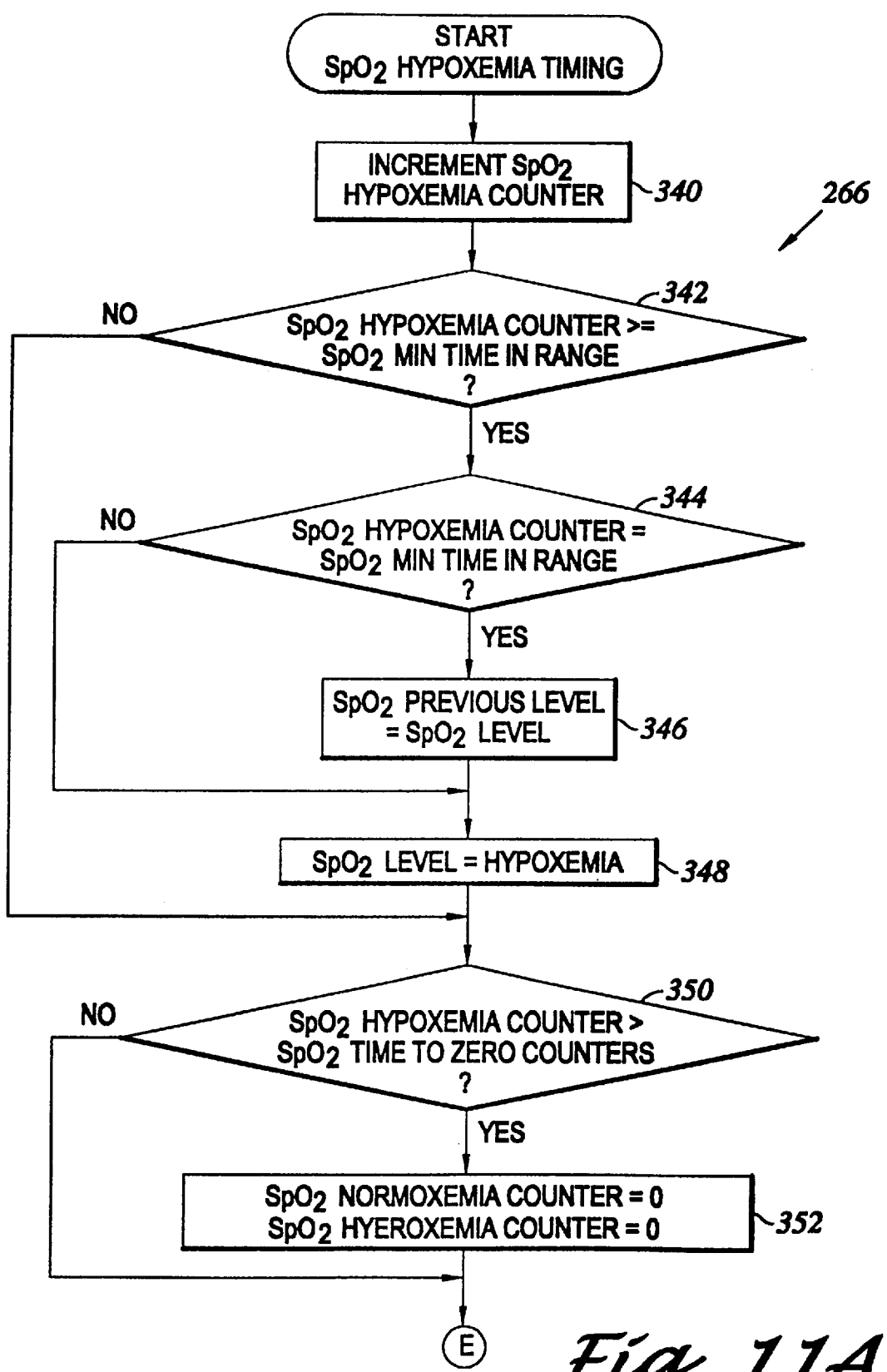
Figure 11B:
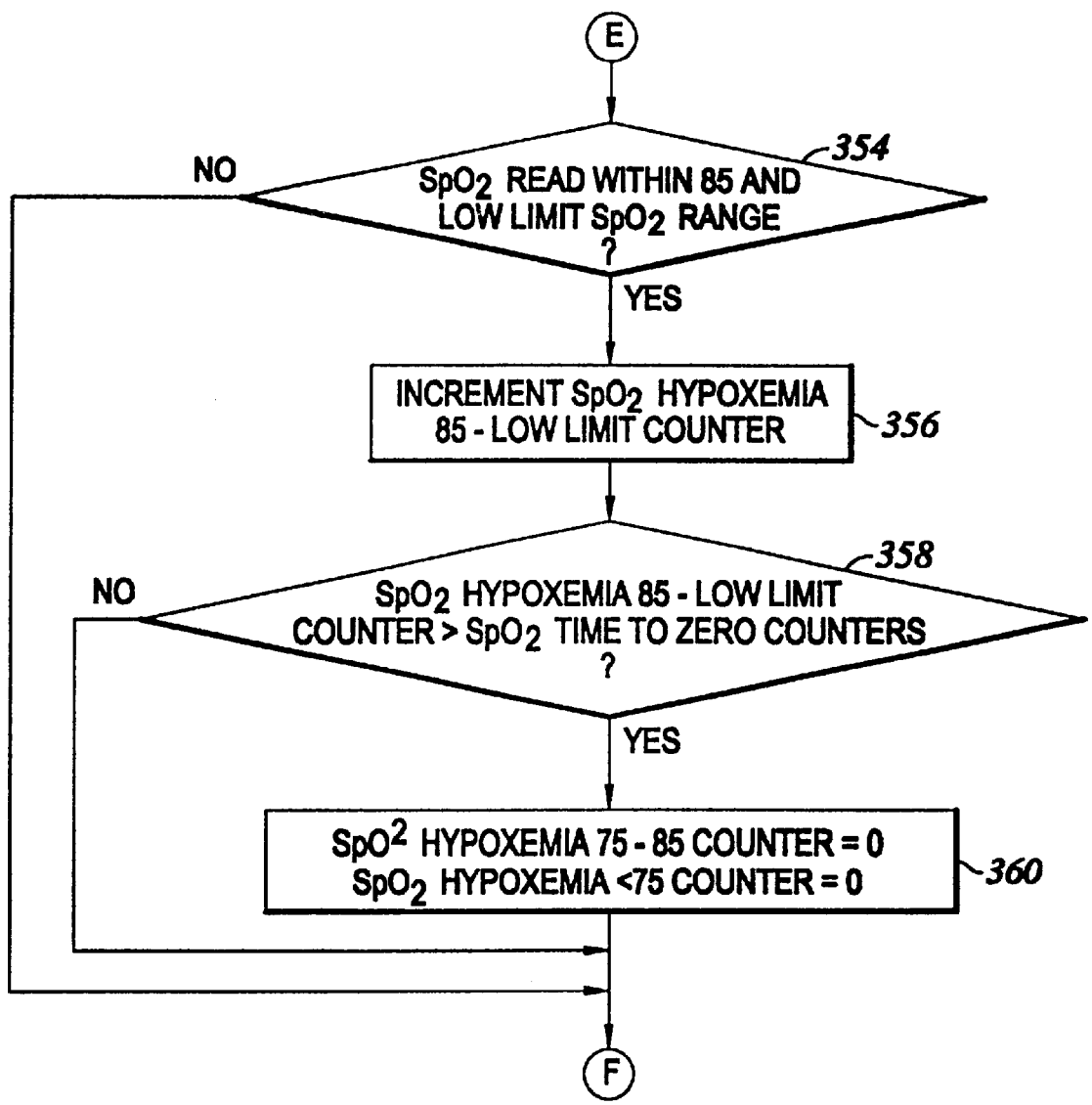
Figure 11C:
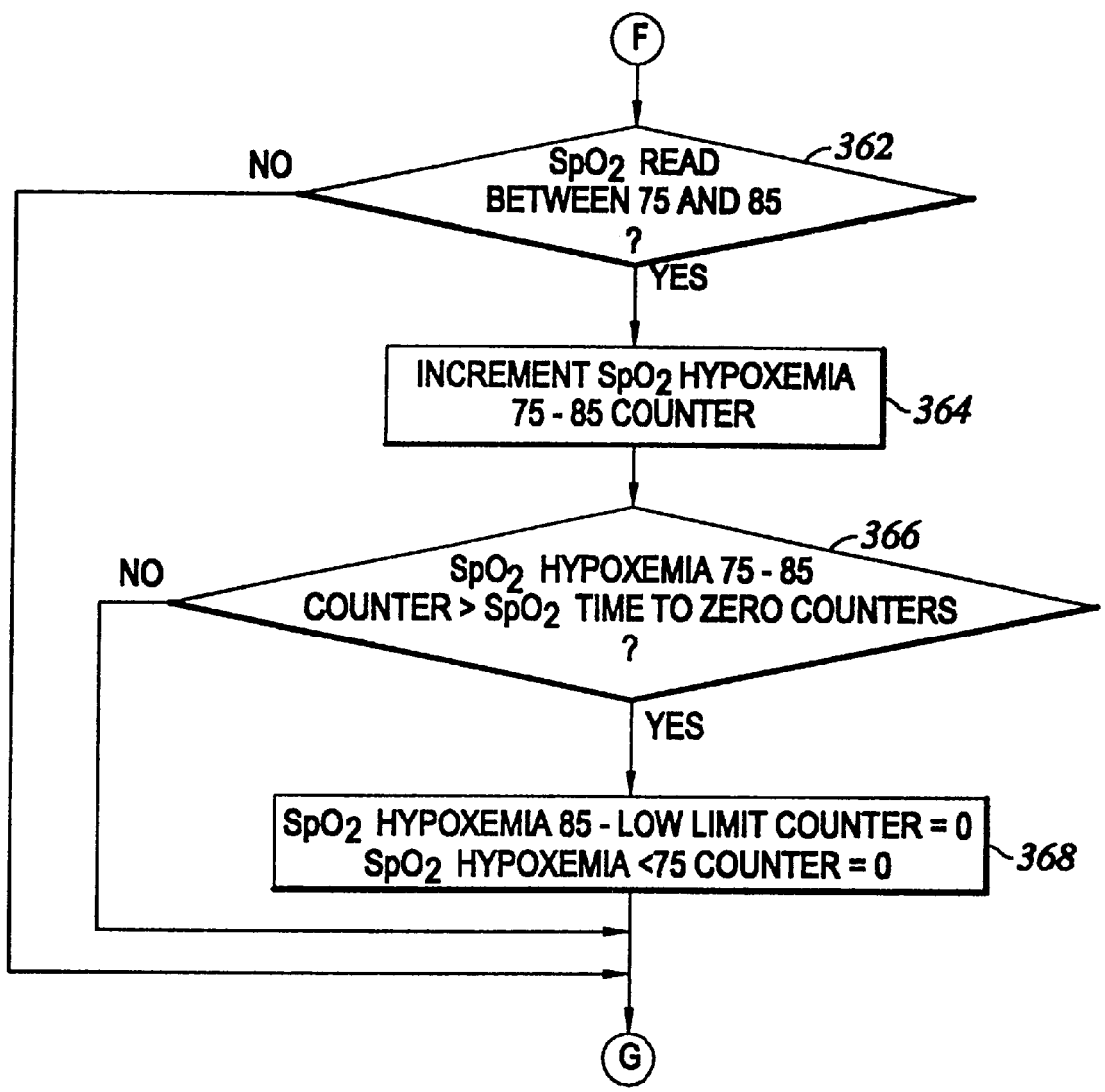
Figure 11D:
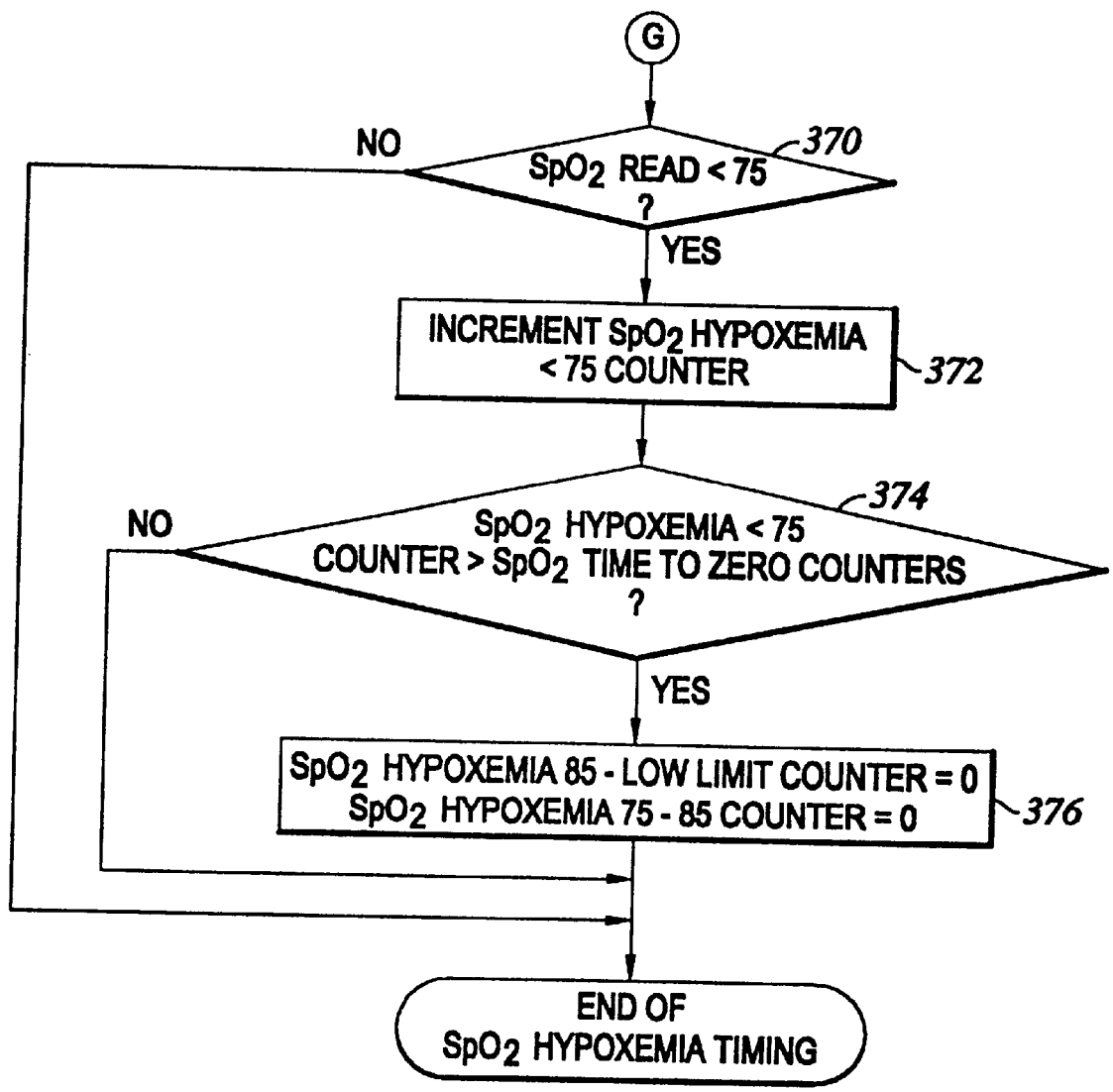

FIG. 10 illustrates exemplary logic for performing hyperoxemia timing in accordance with the present invention. As shown in FIG. 10 and described below, hyperoxemia is considered the new $SpO_2$ level only after a specified period of time (e.g., three seconds) has elapsed since $SpO_2$ entered the hyperoxemia range, however, counters for other $SpO_2$ ranges are reset only after a longer interval (e.g., ten seconds) has elapsed. The logic of FIG. 10 moves from a start block to block 320 where $SpO_2$ Hyperoxemia Counter is incremented. Next, the logic moves to decision block 322 where a test is made to determine if $SpO_2$ Hyperoxemia Counter is greater than or equal to $SpO_2$ Min Time in Range. If so, the logic moves to decision block 324 where a test is made to determine if $SpO_2$ Hyperoxemia Counter is equal to the $SpO_2$ Min Time in Range. If so, the logic moves to block 326 where $SpO_2$ Previous Level is set to $SpO_2$ Level. Regardless of the outcome of decision block 324, the logic proceeds to block 328 where $SpO_2$ Level is set to Hyperoxemia. Regardless of the outcome of decision block 322, the logic moves to decision block 330 where a test is made to determine if $SpO_2$ Hyperoxemia Counter is greater than $SpO_2$ Time to Zero Counters. If so, the logic moves to block 332 where counters ($SpO_2$ Normoxemia Counter, $SpO_2$ Hypoxemia Counter, $SpO_2$ Hypoxemia 85-Low Limit Counter, $SpO_2$ Hypoxemia 75–85 Counter and $SpO_2$ Hypoxemia less than 75 Counter) are set to zero. The logic of FIG. 10 then ends and processing returns to FIG. 8.

Returning to FIG. 8, if $SpO_2$ Read is less than the target range (yes in decision block 264), the logic moves to block 266 where hypoxemia timing is performed as shown in detail in FIG. 11 and described next.

FIG. 11 illustrates exemplary logic for performing hypoxemia timing in accordance with the present invention. As shown in FIG. 11, and described below, hypoxemia is considered the new $SpO_2$ level only after a specified period of time (e.g., three seconds) has elapsed since $SpO_2$ entered the hypoxemia range, however, counters for other $SpO_2$ ranges are reset only after a longer interval (e.g., ten seconds) has elapsed. The logic of FIG. 11 moves from a start block to block 340 where $SpO_2$ Hypoxemia Counter is incremented. Next, the logic moves to decision block 342 where a test is made to determine if $SpO_2$ Hypoxemia Counter is greater than or equal to $SpO_2$ Min Time in Range. If so, the logic moves to decision block 344 where a test is made to determine if $SpO_2$ Hypoxemia Counter is equal to $SpO_2$ Min Time in Range. If so, the logic moves to block 346 where $SpO_2$ Previous Level is set to $SpO_2$ Level. Regardless of the outcome of decision block 344, the logic proceeds to block 348 where $SpO_2$ Level is set to Hypoxemia. Regardless of the outcome of decision block 342, the logic of FIG. 11 proceeds to decision block 350 where a test is made to determine if $SpO_2$ Hypoxemia Counter is greater than $SpO_2$ Time to Zero Counters. If so, the logic moves to block 352 where counters ($SpO_2$ Normoxemia Counter and $SpO_2$ Hyperoxemia Counter) are set to zero.

As described above, hypoxemia is subdivided into ranges, for example, less than 75%, 75%–85% and 85% to the low limit for normoxemia. Hypoxemia counters for the various sub-ranges are set based on $SpO_2$ Read, as appropriate. If $SpO_2$ Read is between 85 and $SpO_2$ Target Range Low Limit, for example, using the exemplary default range, between 85%–88%, (yes in decision block 354), the logic moves to block 356 where $SpO_2$ Hypoxemia 85-Low Limit Counter is incremented. The logic then moves to decision block 358 where a test is made to determine if $SpO_2$ Hypoxemia 85-Low Limit Counter is greater than Time to Zero Counters. If so, the logic moves to block 360 where counters ($SpO_2$ Hypoxemia 75–85 Counter and $SpO_2$ Hypoxemia less than 75 Counter) are set to zero. If $SpO_2$ Read is between 75 and 85 (yes in decision block 362), the logic moves to block 364 where $SpO_2$ Hypoxemia 75–85 Counter is incremented. The logic then moves to decision block 366 where a test is made to determine if $SpO_2$ Hypoxemia 75–85 Counter is greater than $SpO_2$ Time to Zero Counters. If so, the logic moves to block 368 where counters ($SpO_2$ Hypoxemia 85-Low Limit Counter and $SpO_2$ Hypoxemia less than 75 Counter) are set to zero. If $SpO_2$ Read is less than 75 (yes in decision block 370), the logic moves to block 372 where $SpO_2$ Hypoxemia less than 75 Counter is incremented. The logic then proceeds to decision block 374 where a test is made to determine if $SpO_2$ Hypoxemia less than 75 Counter is greater than $SpO_2$ Time to Zero Counters. If so, the logic moves to block 376 where counters ($SpO_2$ Hypoxemia 85-Low Limit Counter and $SpO_2$ Hypoxemia 75–85 Counter) are set to zero. The logic of FIG. 11 then ends and processing returns to FIG. 8.

Returning to FIG. 8, after appropriate timing processing has been performed (e.g., normoxemia timing in block 258, hyperoxemia timing in block 262 or hypoxemia in block 266), the logic of FIG. 8 moves to block 268 where the $SpO_2$ slope calculation is performed as illustrated in detail in FIG. 12 and described next.

Figure 12:
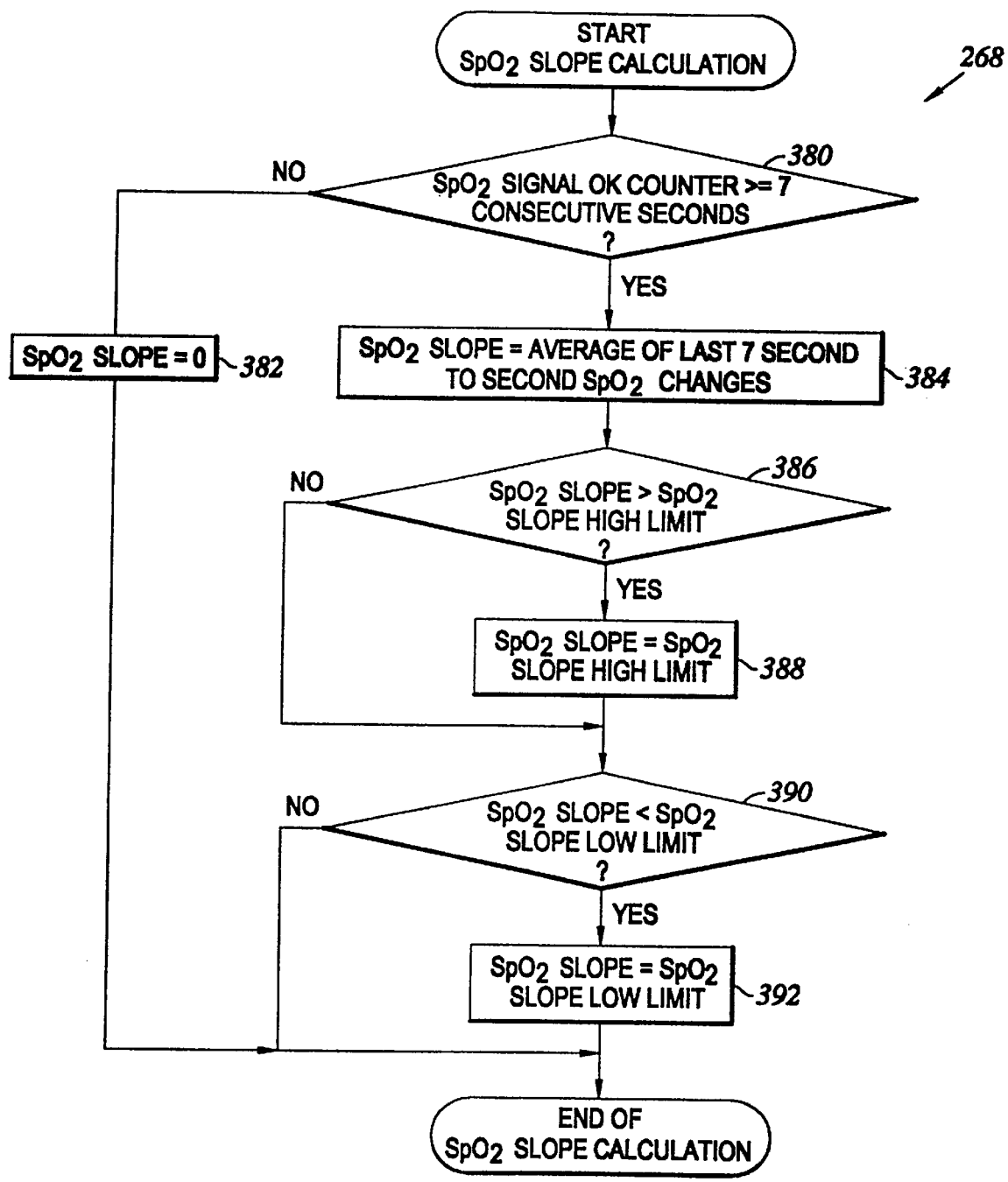

FIG. 12 illustrates exemplary logic for performing the $SpO_2$ slope calculation in accordance with the present invention. Since $SpO_2$ is read and processed every second, the slope is calculated every second. When a slope is calculated, it is calculated based on the current $SpO_2$ reading and the previous seven consecutive $SpO_2$ readings. It will be appreciated that a value other than seven may be used for the number of previous values to use when calculating the slope. All of the readings used in calculating the slope should be within the range where $SpO_2$ signal is considered OK. The slope is the average of the second-to-second $SpO_2$ change. The calculated slope is limited to a specified range. For example, in the illustrated embodiment shown in FIG. 4, the range defaults to +/−5% per second ($SpO_2$ Slope High Limit and $SpO_2$ Slope Low Limit). In various embodiments, multiple slopes can be calculated to track fast, medium, and slow changes simultaneously. The multiple slopes can then be used at different times within the $FiO_2$ Set Determination procedure (shown in FIG. 14).

The logic of FIG. 12 moves from a start block to decision block 380 where a test is made to determine if $SpO_2$ Signal OK Counter is greater than or equal to seven consecutive seconds. If not, the logic moves to block 382 where $SpO_2$ Slope is set to zero and the logic of FIG. 12 ends and processing returns to FIG. 8.

If however, $SpO_2$ Signal OK Counter is greater than or equal to seven consecutive seconds (yes in decision block 380), the logic moves to block 384 where $SpO_2$ Slope is set to the average of the last seven second-to-second $SpO_2$ changes. Next, logic is performed to ensure that the slope is within the allowable limits. If in decision block 386 it is determined that $SpO_2$ Slope is greater then $SpO_2$ Slope High Limit (e.g., a change of more than 5%), the logic moves to block 388 where $SpO_2$ Slope is set to $SpO_2$ Slope High limit (e.g., $SpO_2$ Slope is set to +5%). If it is determined in decision block 390 that $SpO_2$ Slope is less than $SpO_2$ Slope Low Limit, the logic moves to block 392 where $SpO_2$ Slope is set to $SpO_2$ Slope Low Limit (e.g., $SpO_2$ Slope is set to −5%). The logic of FIG. 12 then ends and processing returns to FIG. 8.

Returning to FIG. 8, after the slope has been calculated (block 268), the logic moves to block 270 where $FiO_2$ Max/Min timing is performed as illustrated in detail in FIG. 13 and described next.

Figure 13:
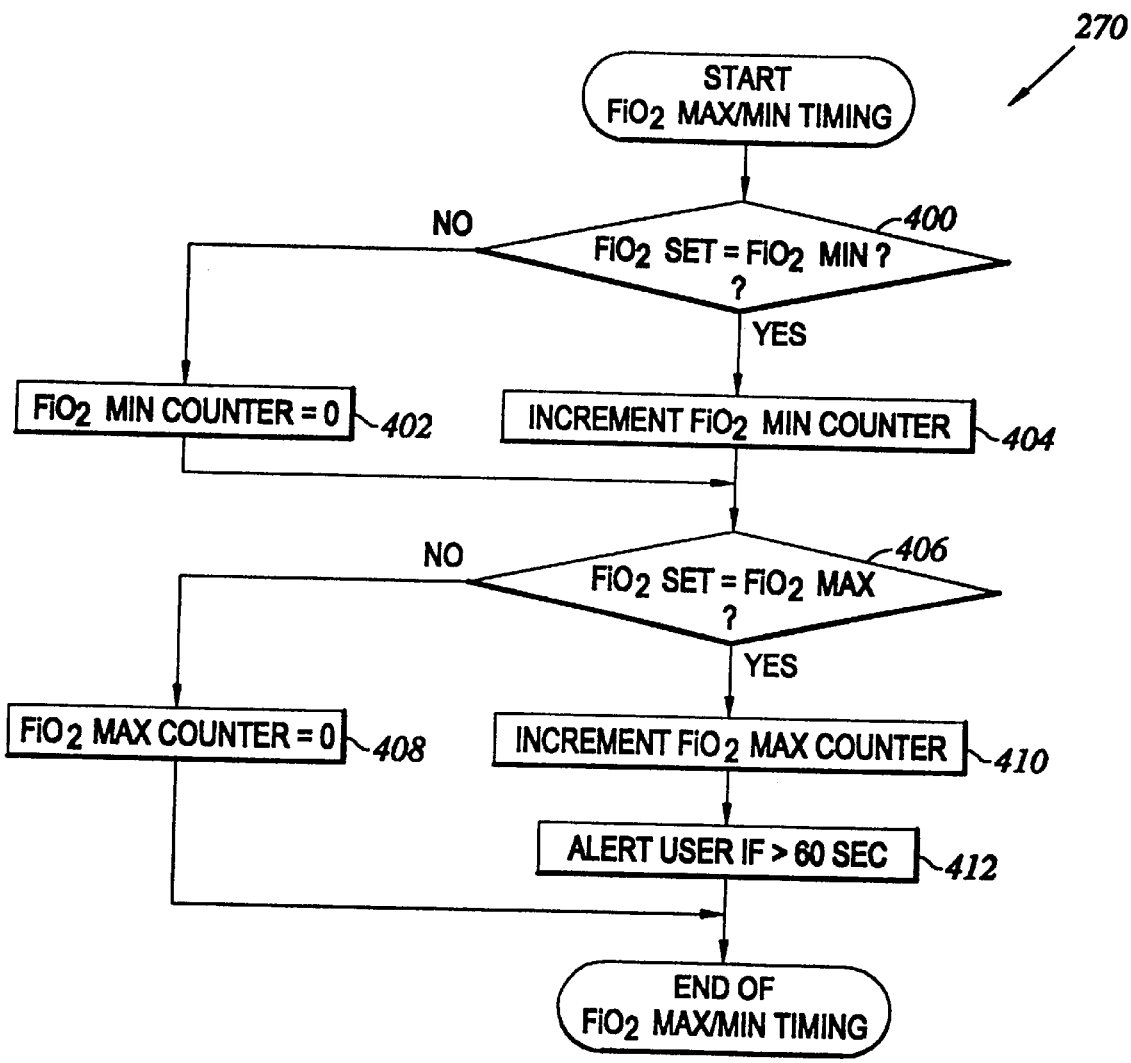
Figure 18:
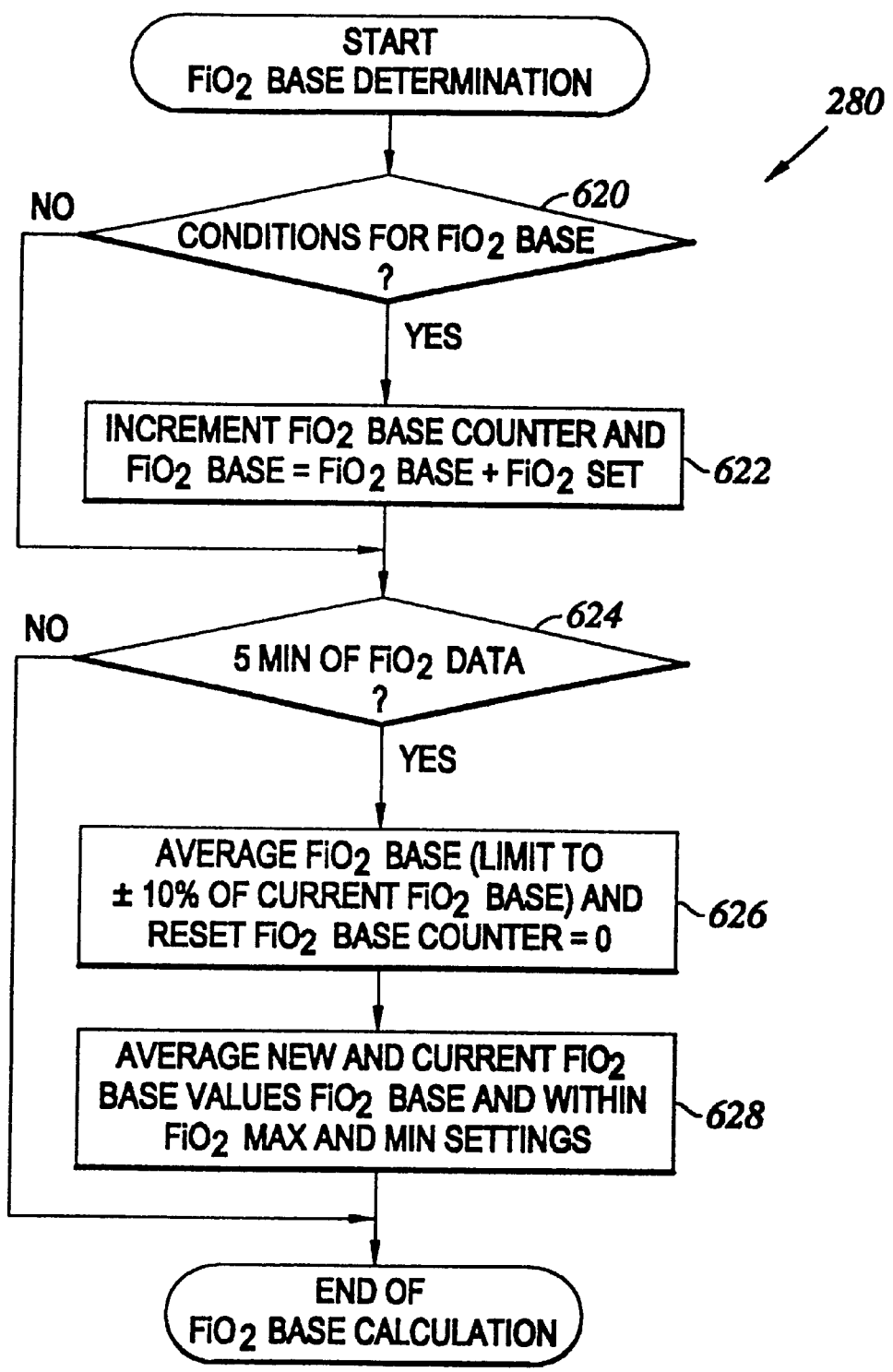

The logic of FIG. 13 illustrates exemplary logic for performing $FiO_2$ Max/Min timing in accordance with the present invention. The algorithm monitors the actual value for $FiO_2$ Set by counting the time at the maximum and minimum $FiO_2$ limits. If $FiO_2$ has been continuously at the maximum limit longer that $FiO_2$ Max Alarm Interval, the user is alerted. The time in $FiO_2$ max and min is also used later for calculation of $FiO_2$ Base (FIG. 18).

The logic of FIG. 13 moves from a start block to decision block 400 where a test is made to determine if $FiO_2$ Set is equal to $FiO_2$ Min. If not, the logic moves to block 402 where $FiO_2$ Min Counter is set to zero. If so, the logic moves to block 404 where $FiO_2$ Min Counter is incremented. Next, the logic moves to decision block 406 where a test is made to determine if $FiO_2$ Set is equal to $FiO_2$ Max. If not, the logic moves to block 408 where $FiO_2$ Max Counter is set to zero and the logic of FIG. 13 ends and processing returns to FIG. 8.

If, however, $FiO_2$ Set is not equal to $FiO_2$ Max, the logic moves from decision block 406 to block 410 where $FiO_2$ Max Counter is incremented. The logic then moves to block 412 where the user is alerted if it ($FiO_2$ Max Counter) is greater than 60 seconds. It will be appreciated that the time may be set to some value other than 60 seconds in various embodiments. The logic of FIG. 13 then ends and processing returns to FIG. 8.

Returning to FIG. 8, after $FiO_2$ Max/Min timing has been performed, the logic moves to decision block 272 where a test is made to determine if closed-loop control is enabled. If so, the logic moves to block 273 where $FiO_2$ Set Determination is performed as illustrated in detail in FIG. 14 and described next.

Figure 14:
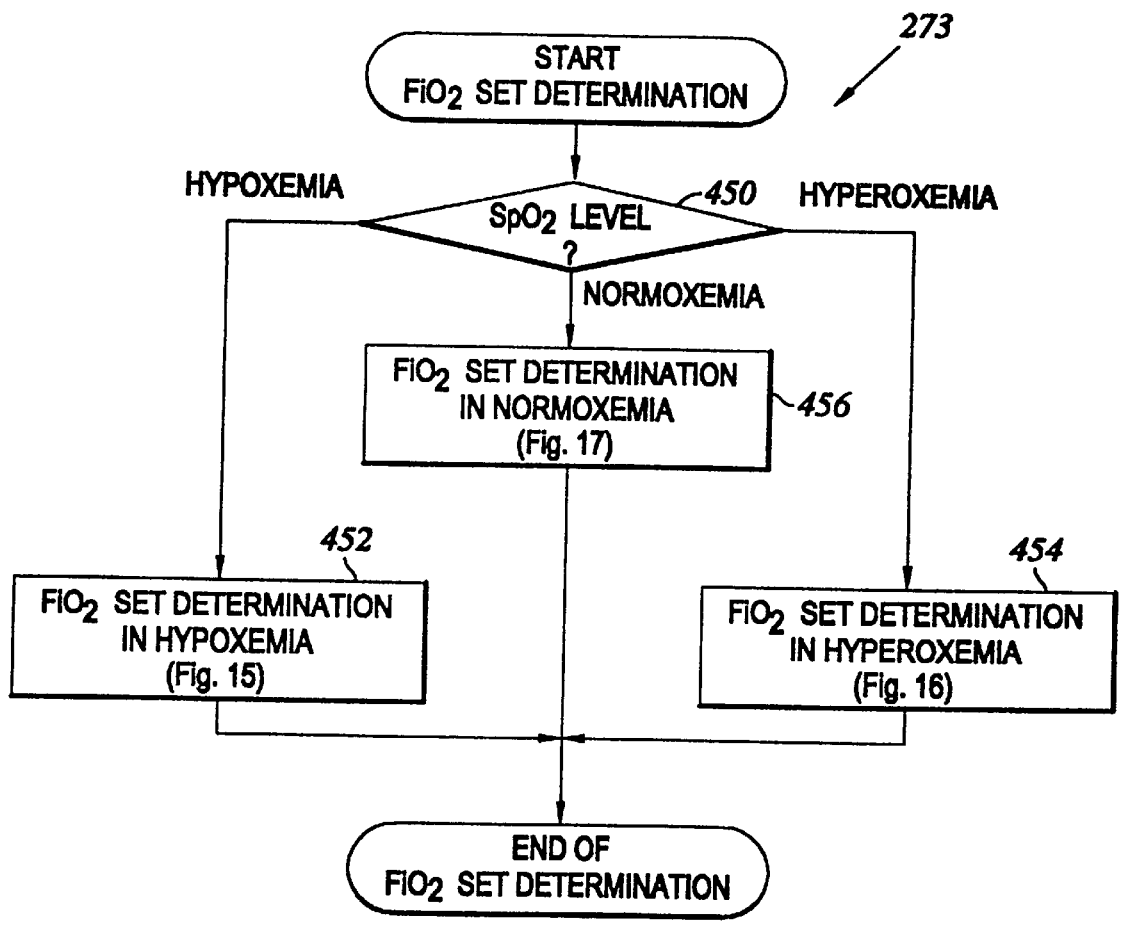

The logic of FIG. 14 illustrates exemplary logic for performing $FiO_2$ Set Determination in accordance with the present invention. $SpO_2$ Read values are classified into $SpO_2$ levels: normoxemia, hyperoxemia and hypoxemia. The updated $FiO_2$ Set value is calculated in different ways according to the oxygenation range ($SpO_2$ level) that $SpO_2$ Read is currently in. The logic of FIG. 14 moves from a start block to decision block 450 where a test is made to determine the $SpO_2$ level. Appropriate processing is then performed based on the $SpO_2$ level. If the $SpO_2$ level indicates hypoxemia, the logic moves to block 452 where $FiO_2$ Set Determination in Hypoxemia is performed as illustrated in detail in FIG. 15 and described below. If the $SpO_2$ level indicates hyperoxemia, the logic moves to block 454 where $FiO_2$ Set Determination in Hyperoxemia is performed as illustrated in detail in FIG. 16 and described below. If the $SpO_2$ level indicates normoxemia, the logic moves to block 456 where $FiO_2$ Set Determination in Normoxemia is performed as illustrated in detail in FIG. 17 and described below.

Figure 15A:
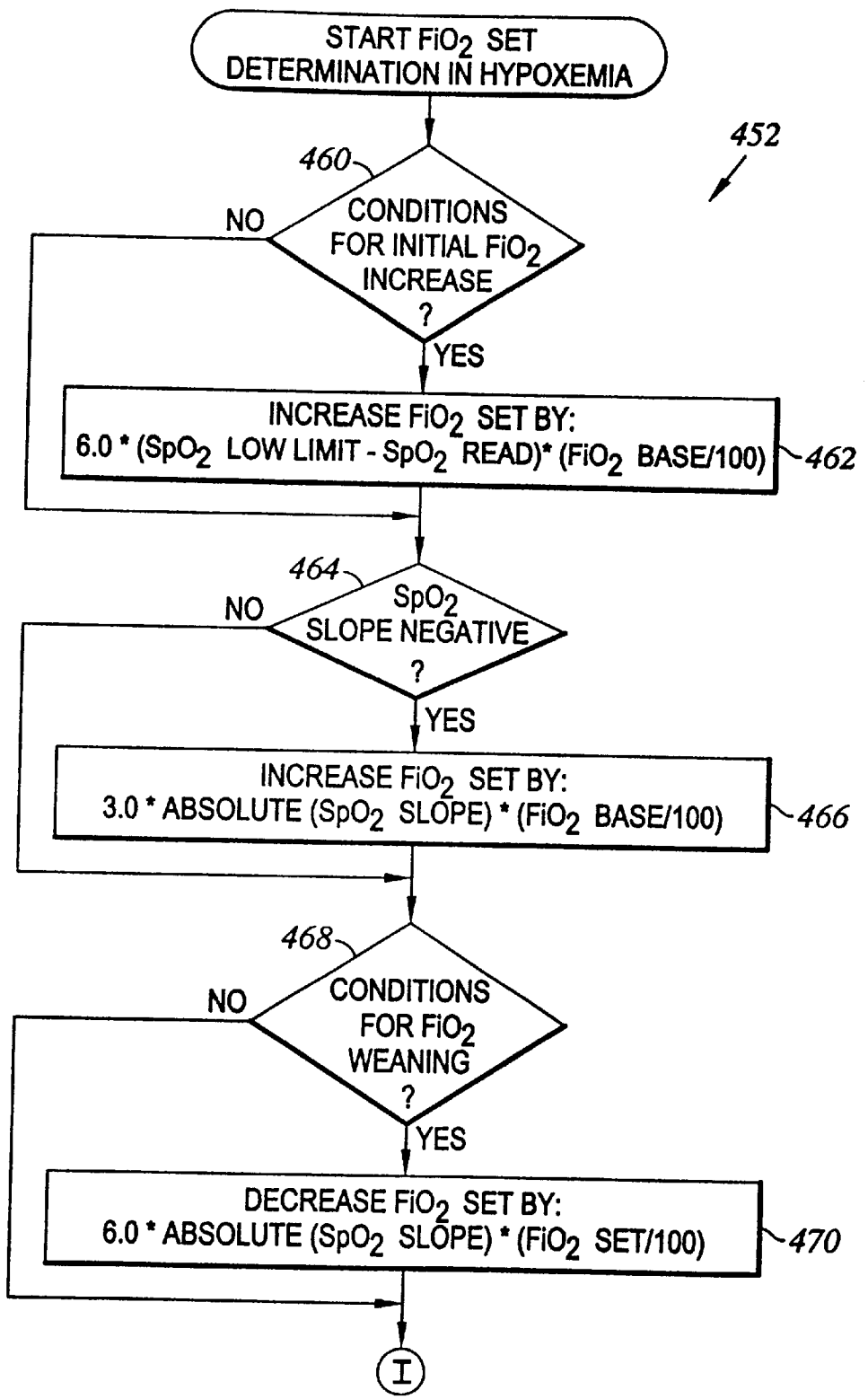
Figure 15B:
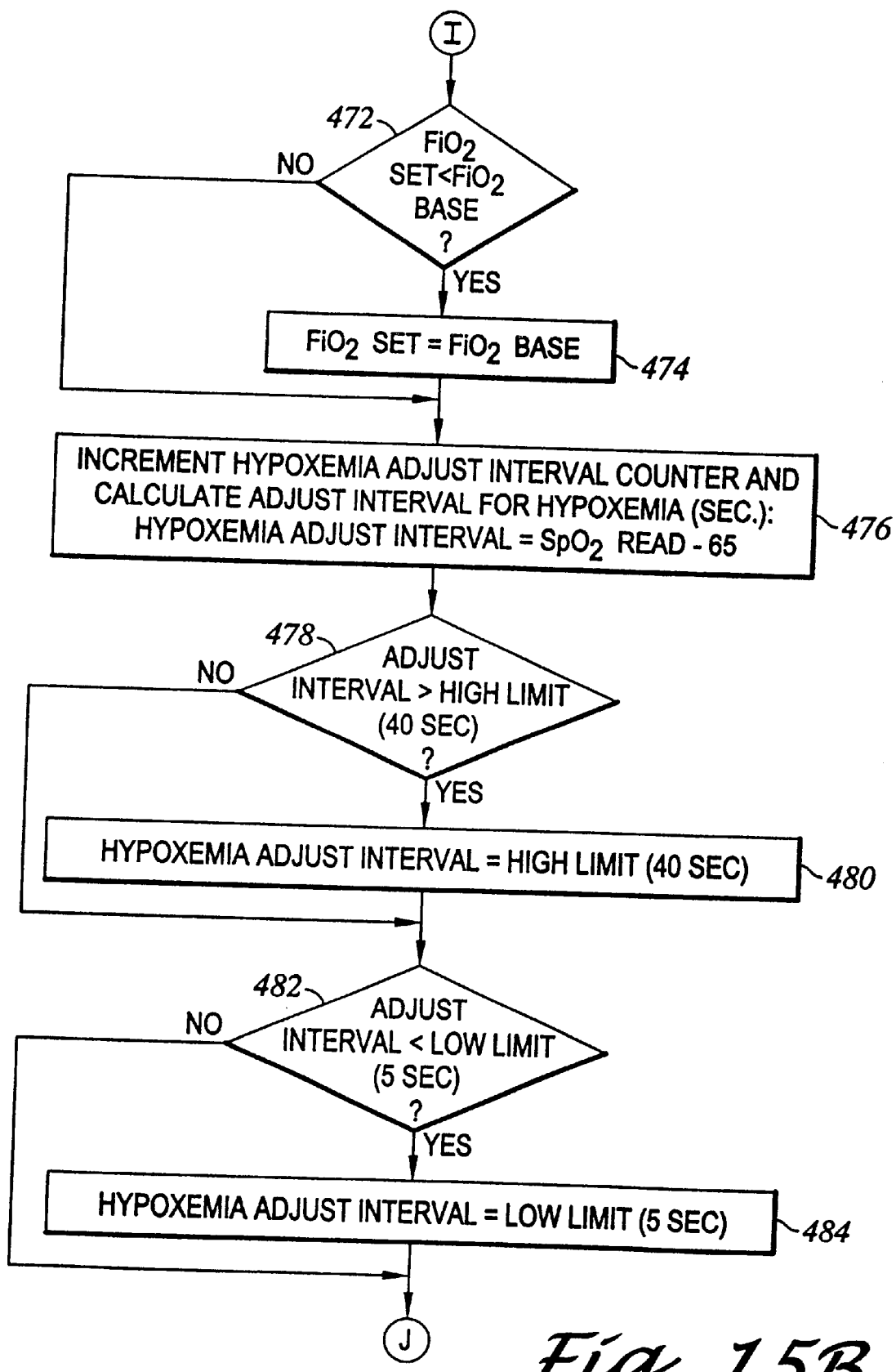
Figure 15C:
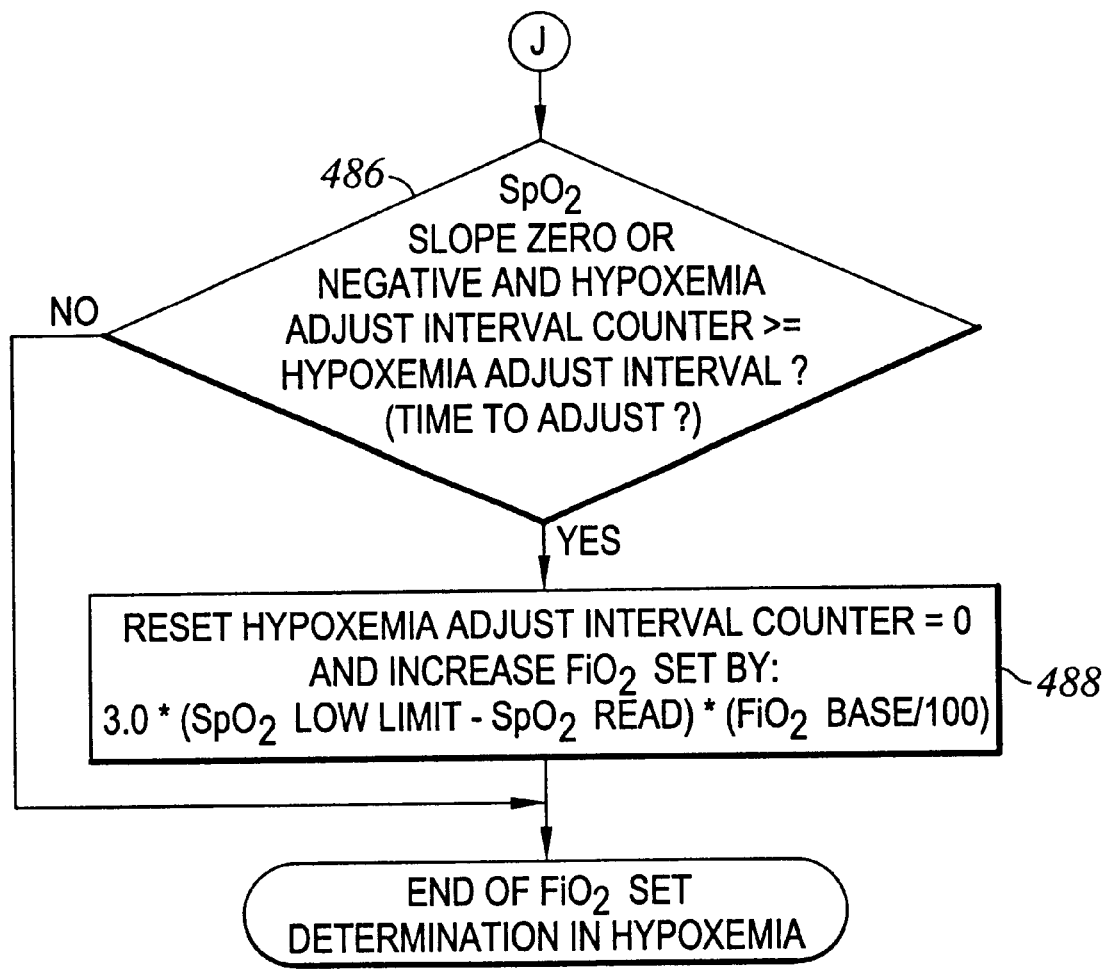
Figure 16A:
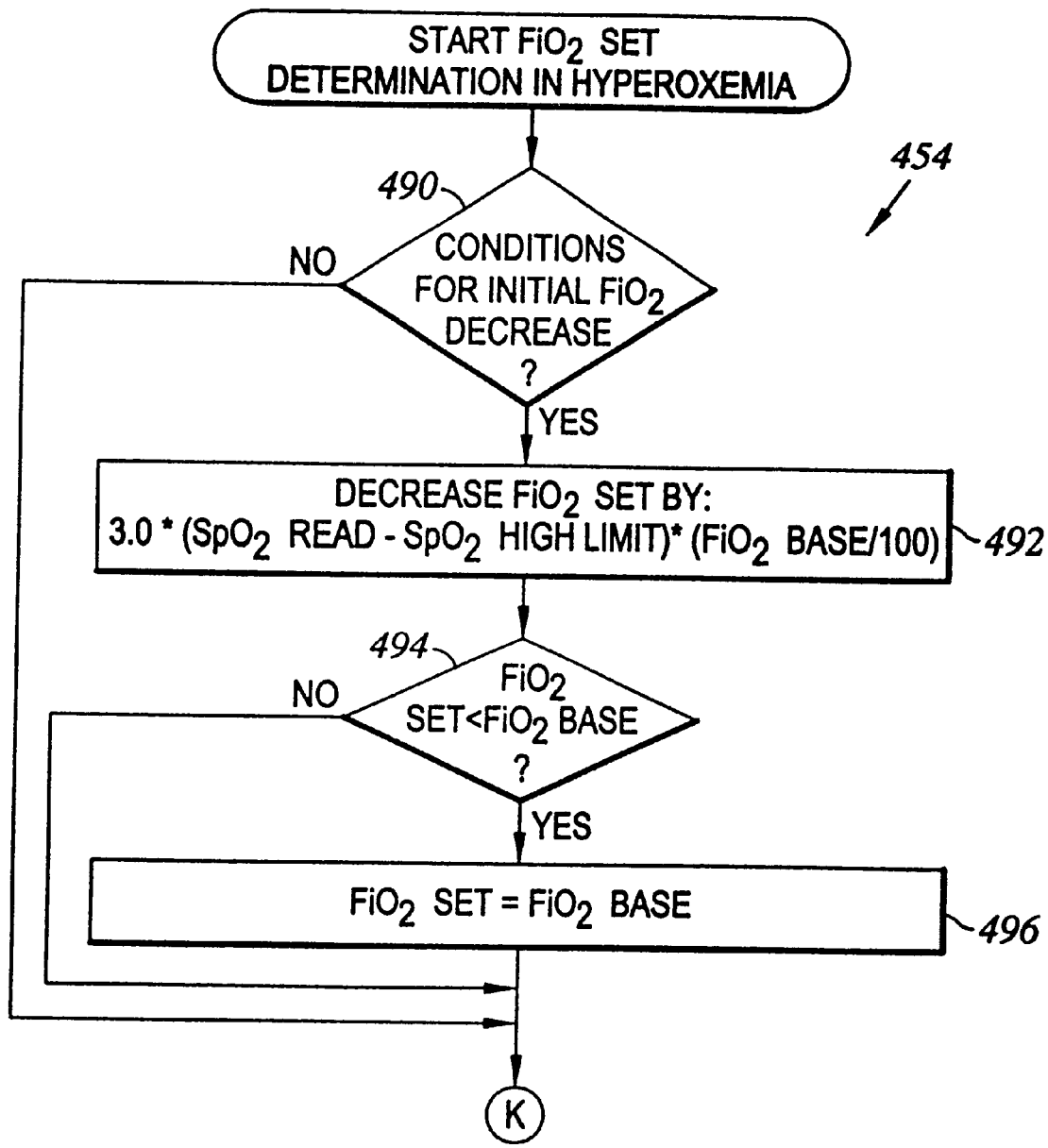
Figure 16B:
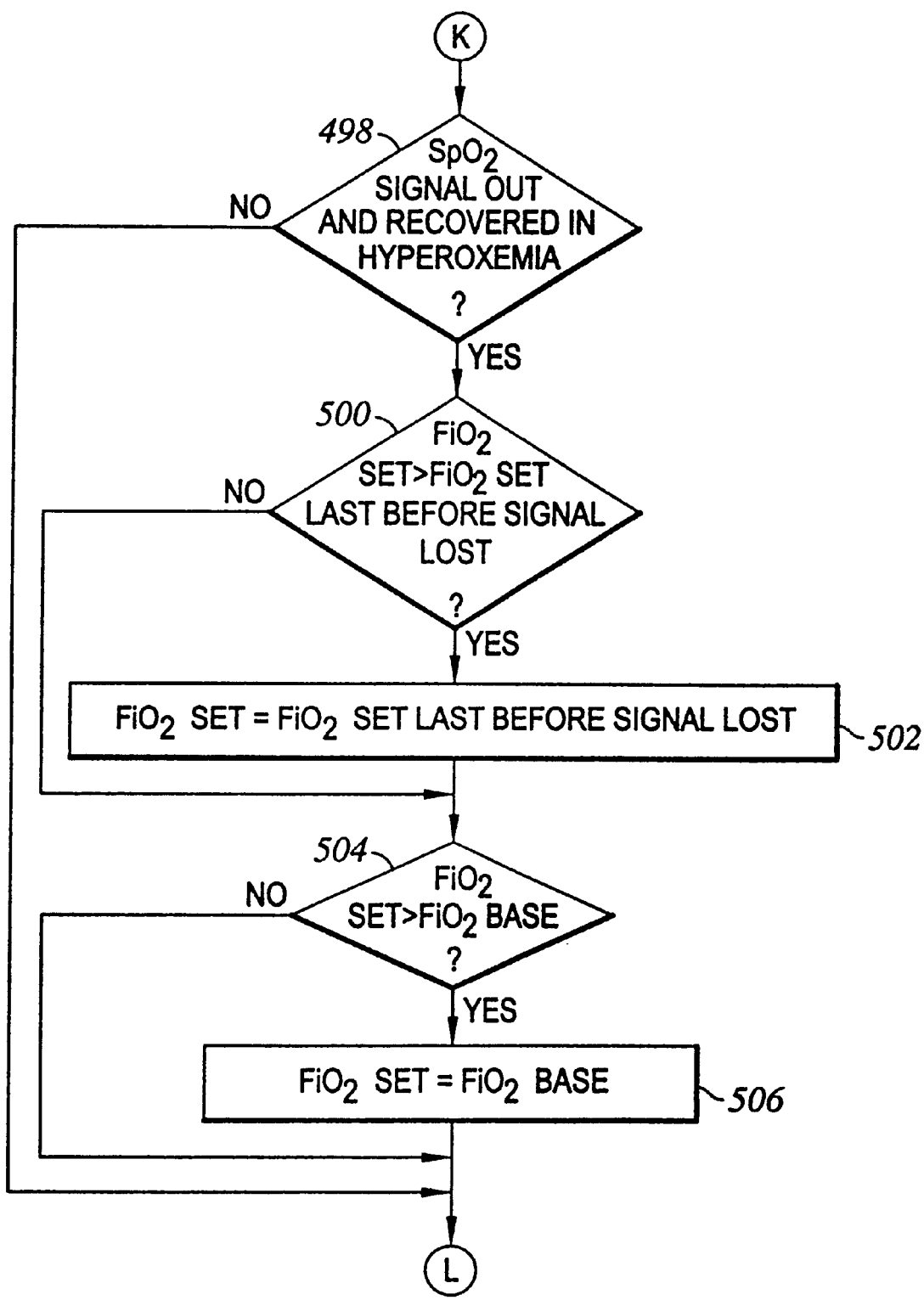
Figure 16C:
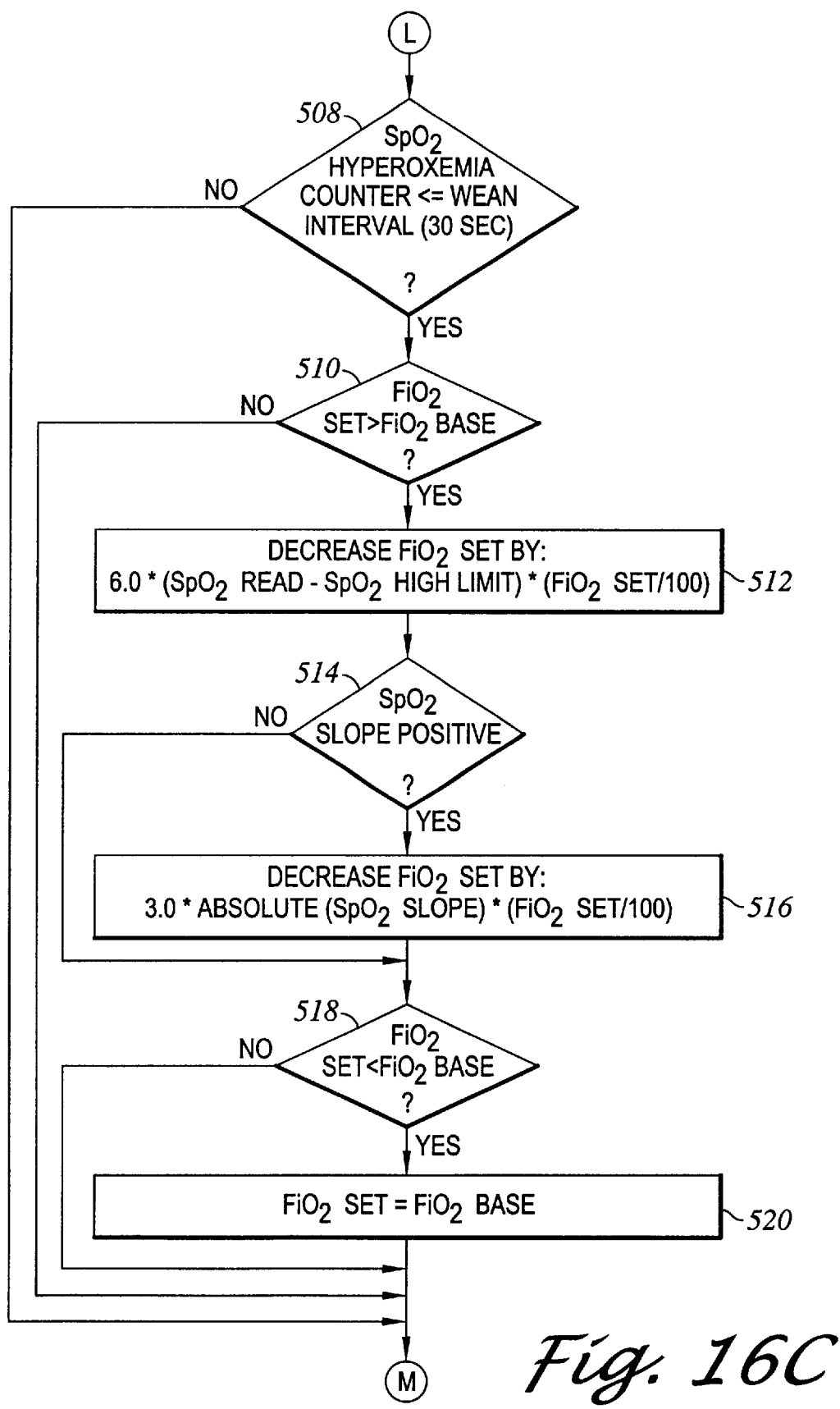
Figure 16D:
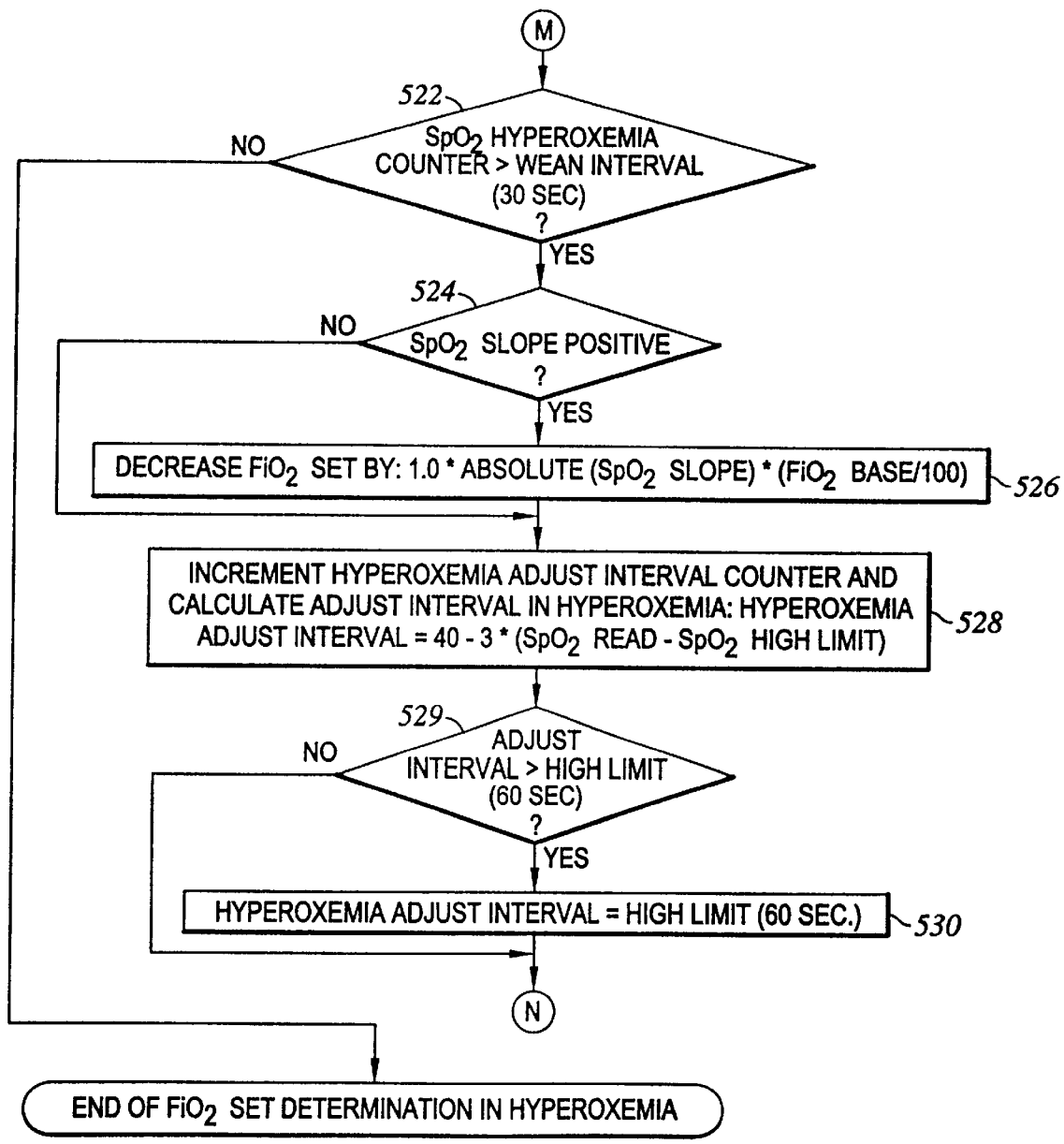
Figure 16E:
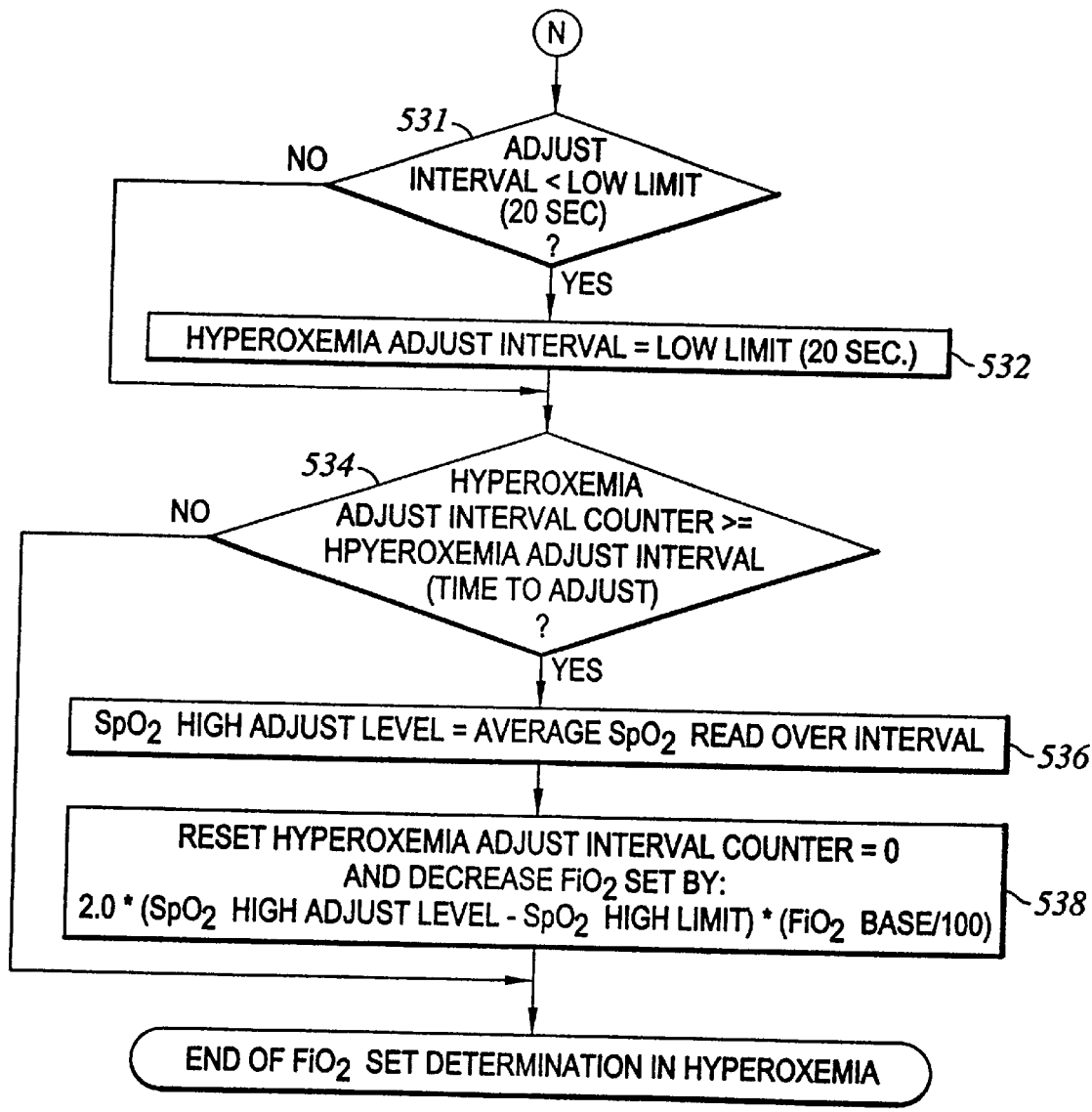
Figure 17A:
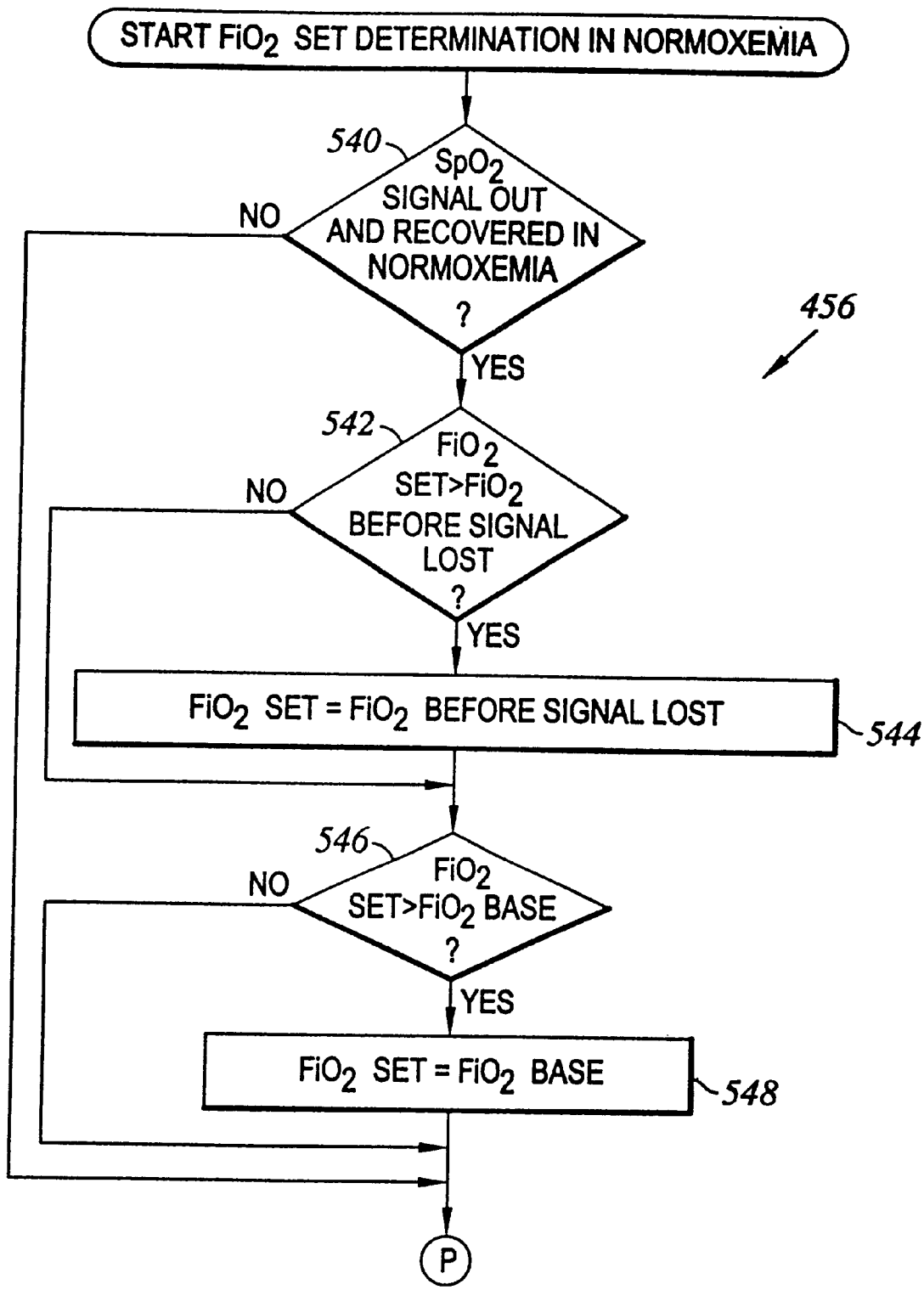
Figure 17B:
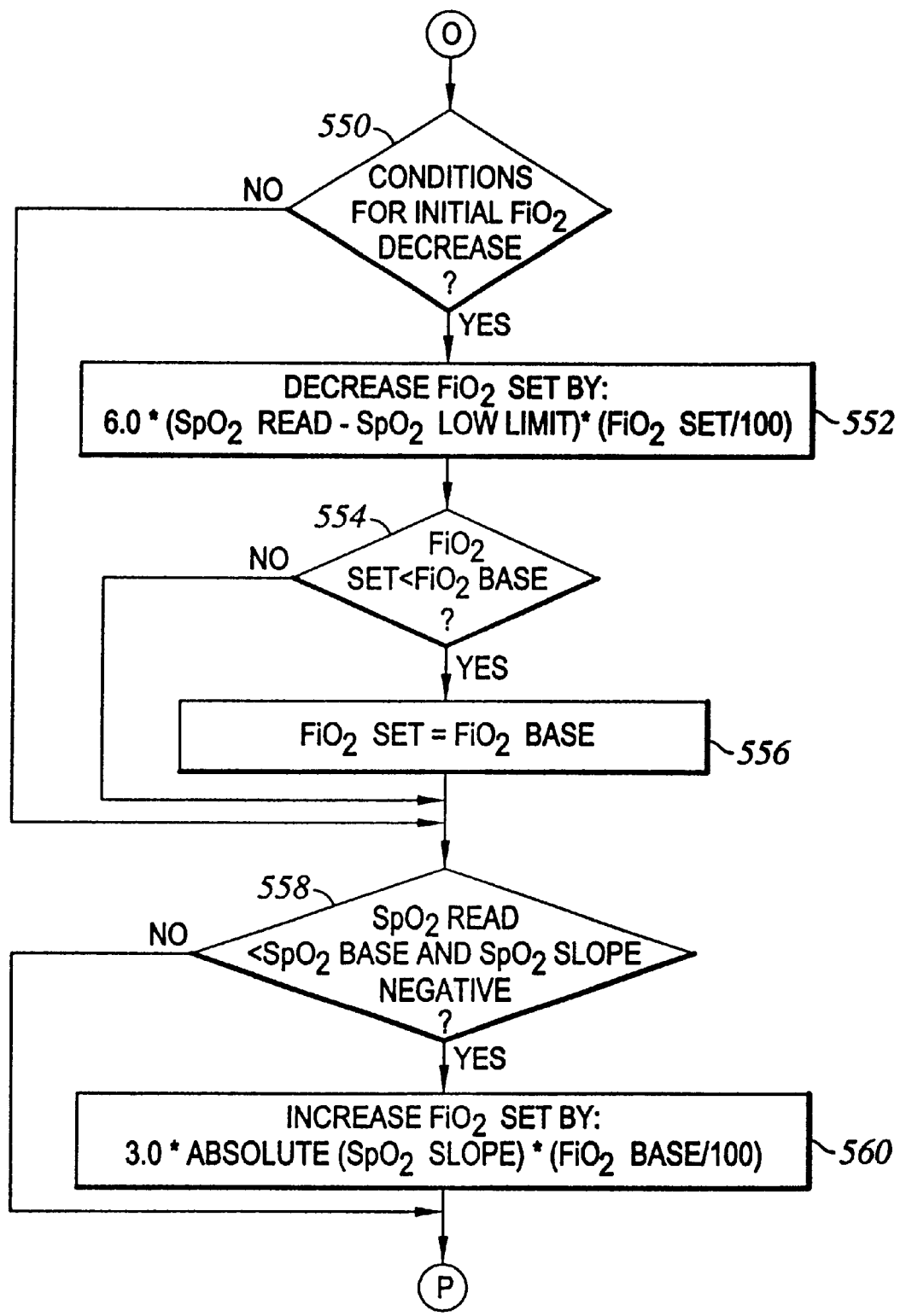
Figure 17C:
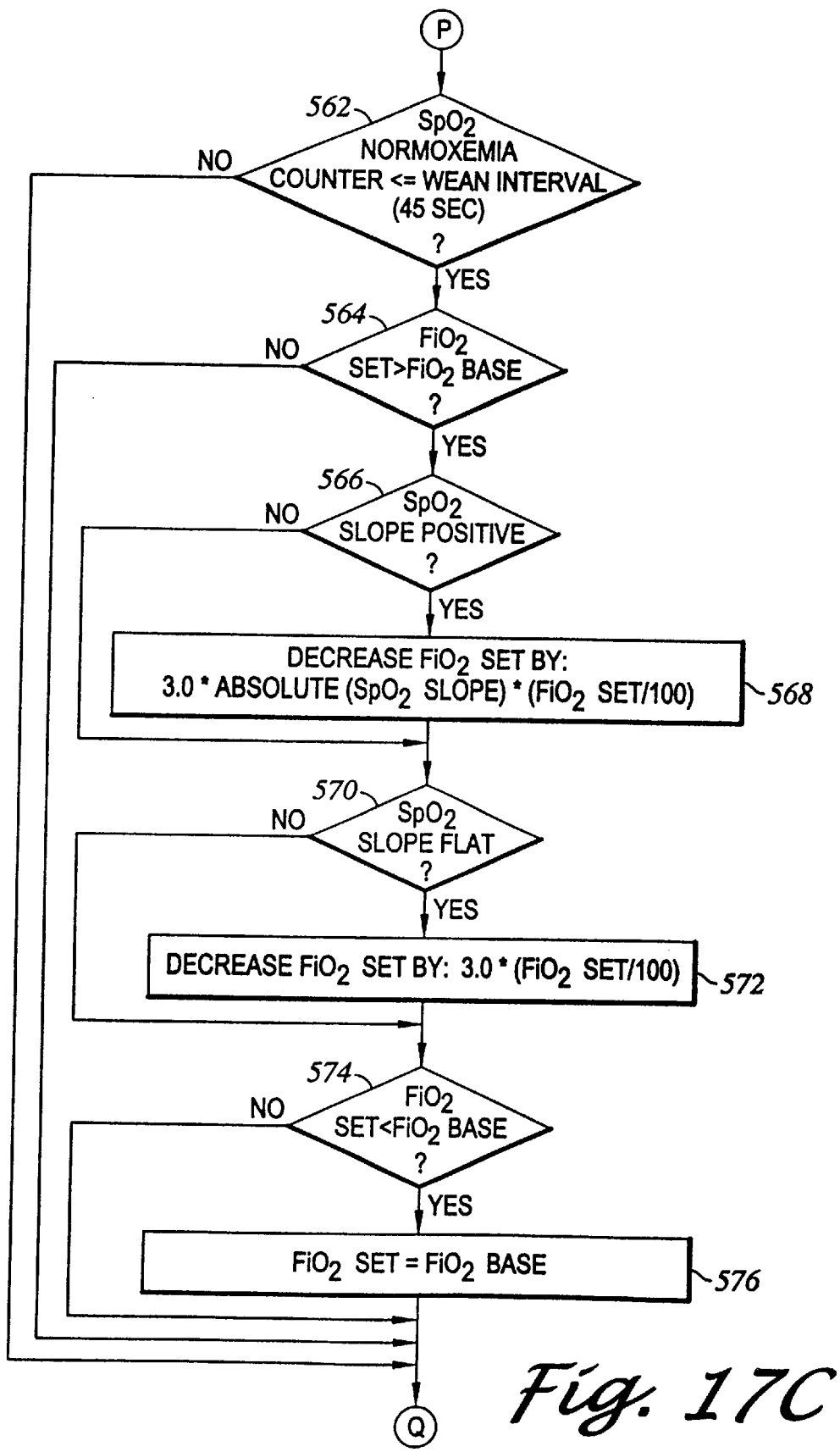
Figure 17D:
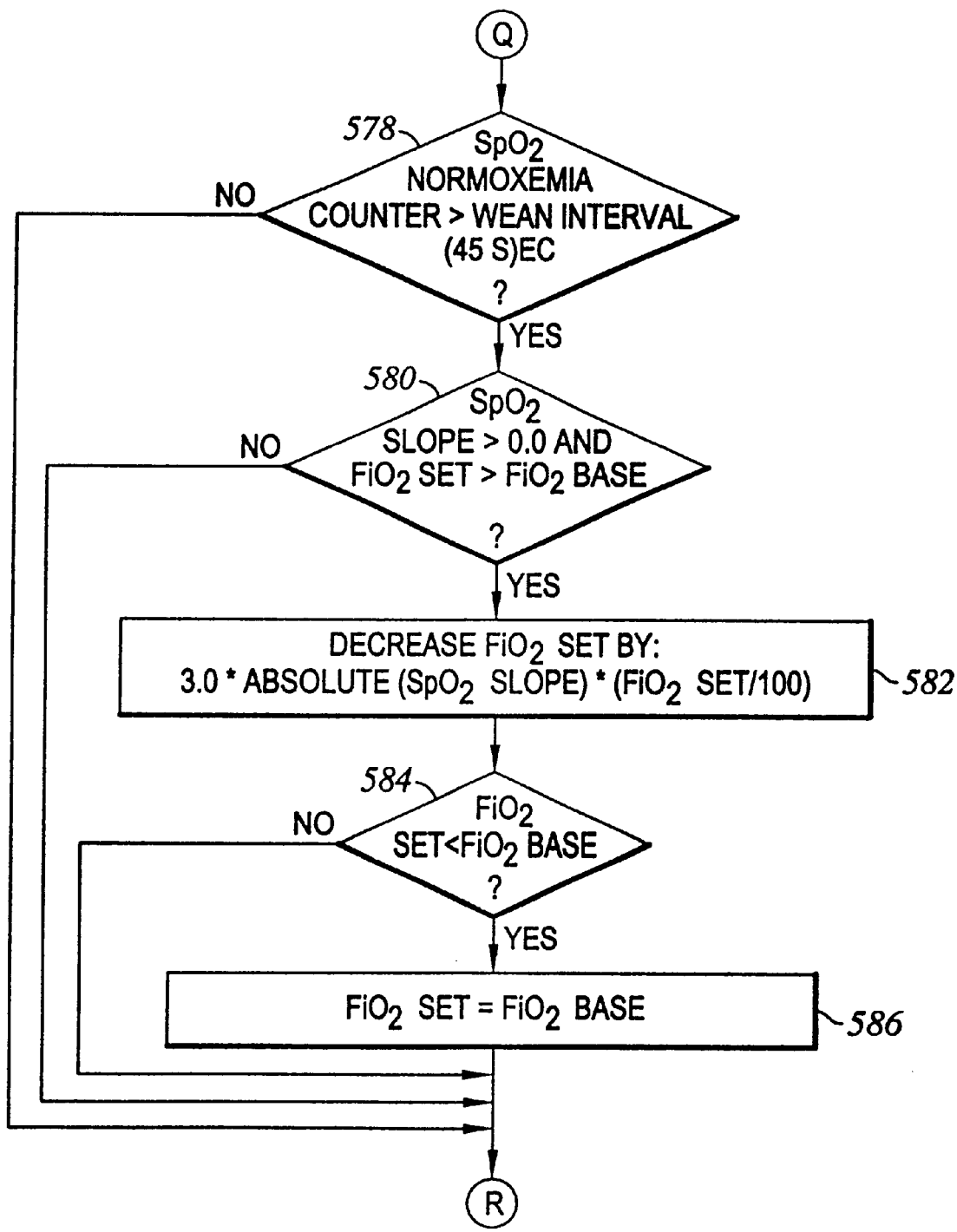
Figure 17E:
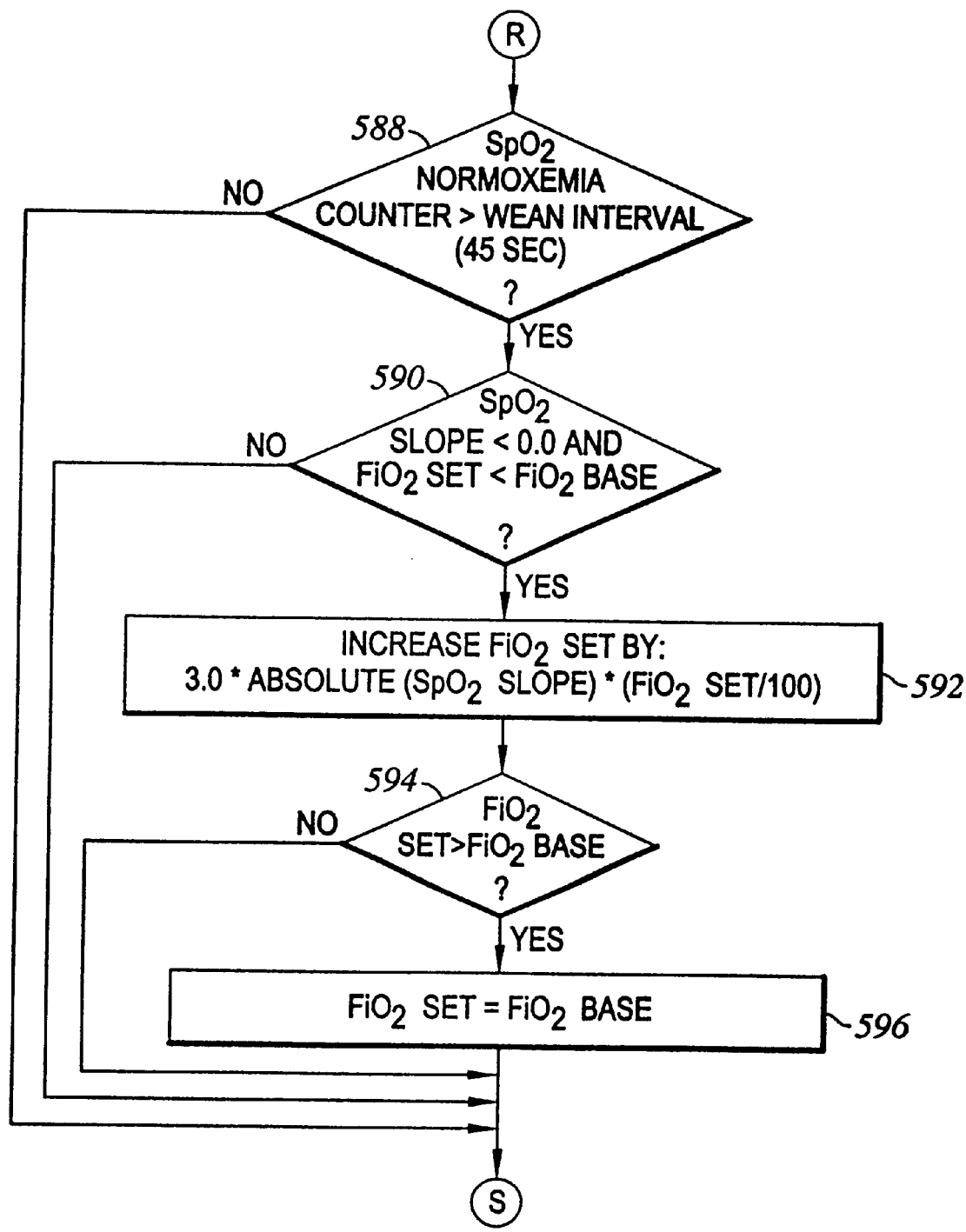
Figure 17F:
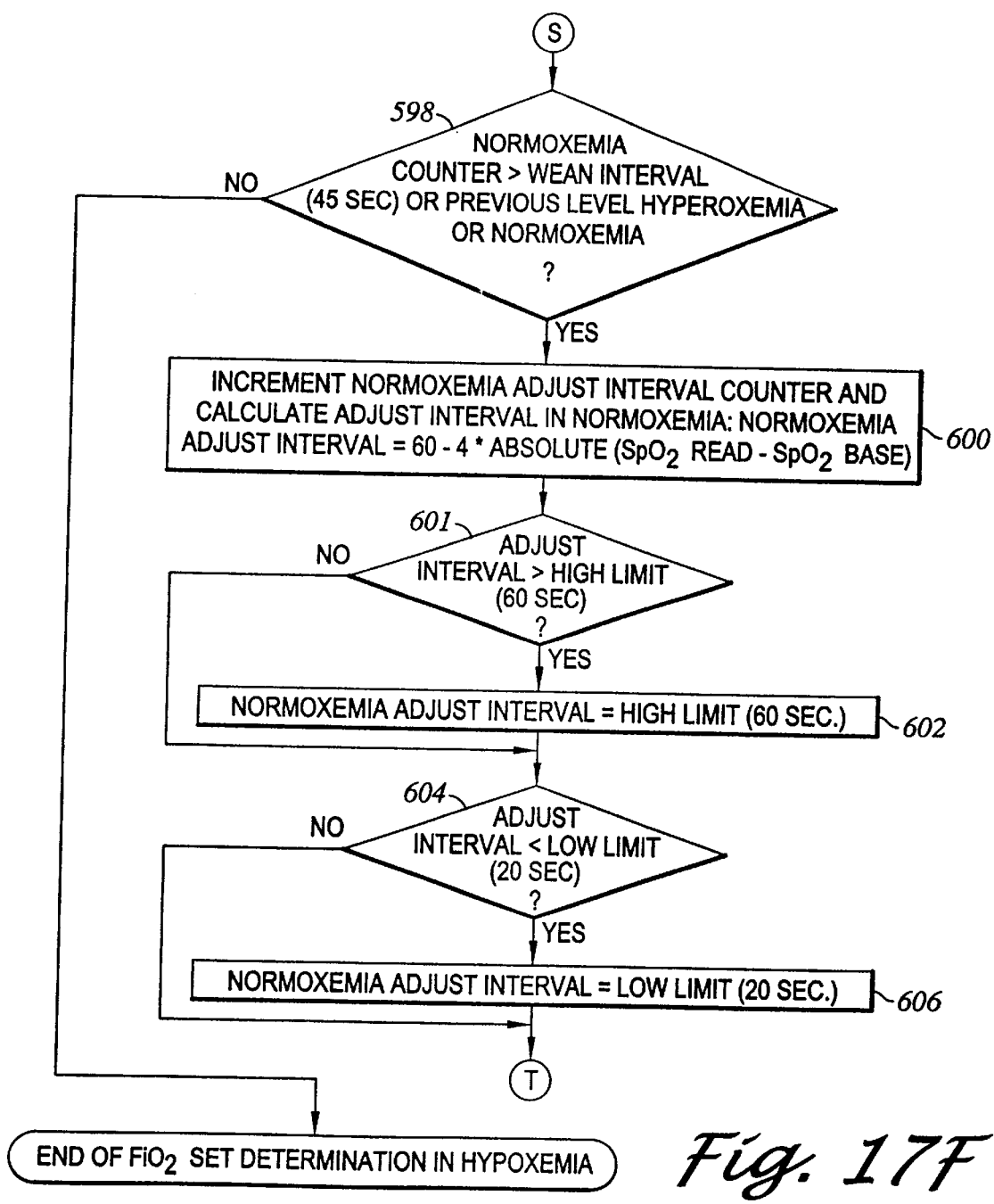
Figure 17G:
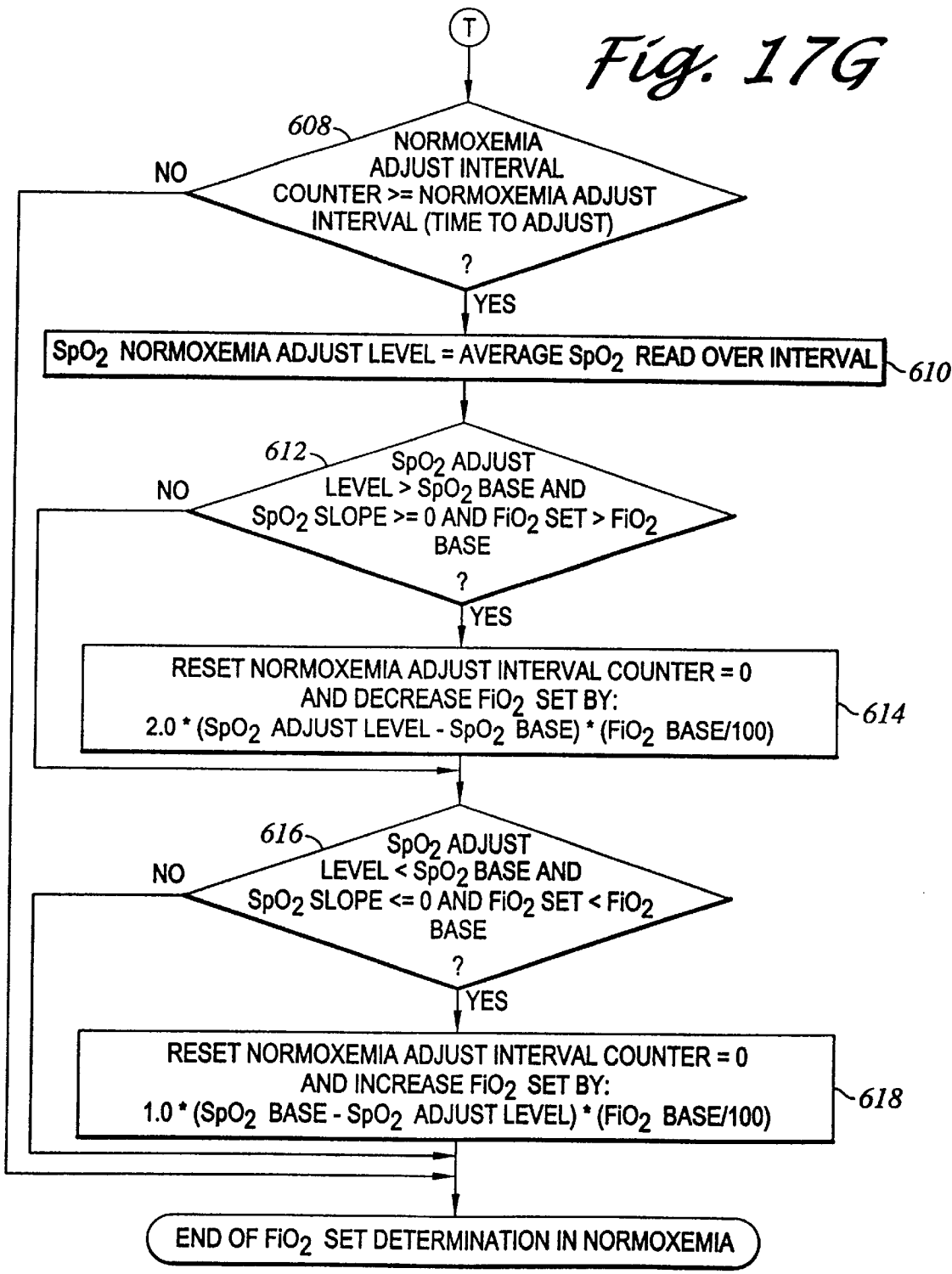

FIG. 15 illustrates exemplary logic for performing $FiO_2$ Set Determination in Hypoxemia in accordance with the present invention. When hypoxemia occurs, the algorithm of the present invention determines an initial increase in $FiO_2$ Set of significant magnitude sufficient to offset the initial cascade effect of hypoxia as well as any lag time in changing the inspired $O_2$ concentration by the delivery mode. As soon as the $SpO_2$ Read value drops below the low limit of the target range set by the user and remains for the minimum required time (e.g., three seconds), the algorithm increases $FiO_2$ Set (occurring once for every time it drops to the hypoxemic range). Simultaneously, if the calculated $SpO_2$ slope is negative (trend is a decrease in $SpO_2$), $FiO_2$ Set is increased in direct proportion to the speed of change (e.g., every second). To prevent overshoot because of the system and intrinsic delays from the time inspired $O_2$ concentration changes until $SpO_2$ returns to normoxemia, $FiO_2$ Set is weaned down in steps proportional to the actual $FiO_2$ Set (e.g., every second) as soon as the $SpO_2$ shows signs of recovery (positive slope). Weaning (reduction) of the excess inspired oxygen concentration prevents arterial unnecessary supplemental oxygen exposure while oxygen saturation levels are in the normal range. $FiO_2$ is not weaned down below the basal level. Weaning is halted if the $SpO_2$ slope is flat or negative. If $SpO_2$ remains in the hypoxemia range and does not show signs of recovery (slope is flat or negative), successive increments of magnitude proportional to the difference between the target range and the $SpO_2$ Read are made. The intervals at which these steps occur vary in duration in inverse proportion to the degree of hypoxemia (a lower $SpO_2$ Read will cause larger increments at shorter intervals).

The logic of FIG. 15 moves from a start block to decision block 460 where a test is made to determine if conditions for initial $FiO_2$ increase are present. In exemplary embodiments, conditions for initial $FiO_2$ increase when $SpO_2$ has just dropped below range are:

$SpO_2$ signal lost and recovered in Hypoxemia

OR $SpO_2$ in Hypoxemia 85-Low Limit and previously $SpO_2$ in Normoxemia

OR $SpO_2$ in Hypoxemia 75–85% and previously $SpO_2$ in Normoxemia or $SpO_2$ in Hypoxemia 85-Low Limit

OR $SpO_2$ in Hypoxemia less than 75% and previously $SpO_2$ in Normoxemia or $SpO_2$ in Hypoxemia 85-Low Limit or $SpO_2$ in Hypoxemia 75–85%.

If conditions for initial $FiO_2$ increase (such as those described above) are present, the logic moves to block 462 where $FiO_2$ Set is increased using the following equation:

$$FiO_2\ Set = FiO_2\ Set + 6.0*(SpO_2\ Low\ Limit - SpO_2\ Read)*(FiO_2\ Base/100) \quad (1)$$

Next, the logic moves to decision block 464 where a test is made to determine if the slope is negative. If so, the logic moves to block 466 where $FiO_2$ Set is increased in direct proportion to the speed of change using the following equation:

$$FiO_2\ Set = FiO_2\ Set + 3.0*absolute\ (SpO_2\ Slope)*(FiO_2\ Base/100) \quad (2)$$

The logic then moves to decision block 468 where a test is made to determine whether conditions for $FiO_2$ weaning are present. In exemplary embodiments, conditions for $FiO_2$ weaning when $SpO_2$ begins to recover include:

$SpO_2$ Read>75

AND $SpO_2$ Slope>0

AND $FiO_2$ Set>$FiO_2$ Base

AND $SpO_2$ Signal OK Counter>$SpO_2$ OK Time Min (e.g., five seconds).

If conditions for weaning are present, the logic moves to block 470 where $FiO_2$ Set is decreased using the following equation:

$$FiO_2\ Set = FiO_2\ Set - 6.0*absolute\ (SpO_2\ Slope)*(FiO_2\ Set/100) \quad (3)$$

Next, the logic moves to decision block 472 where a test is made to determine if $FiO_2$ Set is less than $FiO_2$ Base. If so, the logic moves to block 474 where $FiO_2$ Set is set to $FiO_2$ Base. The logic then moves to block 476 where Hypoxemia Adjust Interval Counter (in seconds) is incremented and Hypoxemia Adjust Interval is calculated using the following equation:

$$Hypoxemia\ Adjust\ Interval = SpO_2\ Read - 65 \quad (4)$$

The Hypoxemia Adjust Interval is limited to a specific range. The logic moves to decision block 478 where a test is made to determine if the Hypoxemia Adjust Interval is greater than the High Limit ($SpO_2$ Low Adjust Interval High Limit), for example, 40 seconds. If so, the logic moves to block 480 where the Hypoxemia Adjust Interval is set to the High Limit, e.g., 40 seconds. The logic proceeds to decision block 482 where a test is made to determine if the Hypoxemia Adjust Interval is less than the Low Limit ($SpO_2$ Low Adjust Interval Low Limit), for example, 5 seconds. If so, the logic moves to block 484 where the Hypoxemia Adjust Interval is set to the Low Limit, e.g., five seconds.

Next, a determination must be made as to whether it is time to adjust. The logic moves to decision block 486 where a test is made to determine if $SpO_2$ Slope is negative or zero and Hypoxemia Adjust Interval Counter is greater than or equal to Hypoxemia Adjust Interval. If so, the logic moves to block 488 where Hypoxemia Adjust Interval Counter is reset to zero and $FiO_2$ Set is increased using the following equation:

$$FiO_2\ Set = FiO_2\ Set + 3.0*(SpO_2\ Low\ Limit - SpO_2\ Read)*(FiO_2\ Base/100) \quad (5)$$

The logic of FIG. 15 then ends and processing returns to FIG. 14.

FIG. 16 illustrates exemplary logic for performing $FiO_2$ Set Determination in Hyperoxemia in accordance with the present invention. When hyperoxemia occurs, the system determines an appropriate initial decrease of $FiO_2$ Set that is of significant magnitude. This reduction is smaller than that occurring initially with hypoxemia. As soon as $SpO_2$ Read exceeds the limit of the target range set by the user and remains for the minimum required time within each range (e.g., three seconds), the algorithm decreases $FiO_2$ Set (once each time it reaches the hyperoxemic range). If $SpO_2$ signal was lost (OUT) and when recovered shows values in hyperoxemia, the $FiO_2$ Set value is changed to the $FiO_2$ Set value that was last recorded when $SpO_2$ dropped out. The new $FiO_2$ Set value should not exceed the $FiO_2$ Base level. When $SpO_2$ Read values reach the hyperoxemic range, the algorithm allows for weaning of $FiO_2$ Set during a wean interval (e.g., 30 seconds) occurring every second only if the current $FiO_2$ Set value is above the $FiO_2$ Base level or the $SpO_2$ Slope is positive (more hyperoxemic). Under both circumstances the $FiO_2$ Set value is weaned down only to the $FiO_2$ Base level. Once $SpO_2$ Read values have been in the hyperoxemic range longer than the initial wean interval (e.g., 30 seconds), the current $FiO_2$ Set value is decreased in proportion to a positive $SpO_2$ Slope (every second, but smaller adjustments). $FiO_2$ Set value can be lowered below the $FiO_2$ Base level. After the initial wean interval (e.g., 30 seconds) has elapsed, $FiO_2$ Set value is decreased at steps of magnitude proportional to the difference between the hyperoxemic $SpO_2$ Read value and the target $SpO_2$ range and the $FiO_2$ Base level. These adjustments, however, are smaller than those observed during hypoxemia. The intervals at which these adjustments occur are in inverse proportion to the degree of hyperoxemia. Therefore, an $SpO_2$ reading average of 97% will result in a smaller reduction than a 99% reading and at longer intervals. These reductions can lower $FiO_2$ Set below $FiO_2$ Base level.

The logic of FIG. 16 moves from a start block to decision block 490 where a test is made to determine if conditions for initial $FiO_2$ decrease are present. In exemplary embodiments of the invention, conditions for initial $FiO_2$ decrease when $SpO_2$ has just crossed the high limit of the target range are:

$SpO_2$ Hyperoxemia Counter=Min Time in Range (e.g., three seconds)

AND $SpO_2$ previously in Normoxemia OR $SpO_2$ Previously in Hypoxemia

AND $FiO_2$ Set>$FiO_2$ Base.

If conditions for initial $FiO_2$ decrease are present, he logic moves to block 492 where $FiO_2$ Set is decreased using the following equation:

$$FiO_2 \text{ Set}=FiO_2 \text{ Set}-3.0*(SpO_2 \text{ Read}-SpO_2 \text{ High Limit})*(FiO_2 \text{ Base}/100) \quad (6)$$

Next, the logic moves to decision block 494 where a test is made to determine if $FiO_2$ Set is less than $FiO_2$ Base. If so, the logic moves to block 496 where $FiO_2$ Set is set to $FiO_2$ Base. Next, the logic moves to decision block 498 where a test is made to determine if $SpO_2$ Signal was OUT and recovered in hyperoxemia. If so, the logic moves from decision block 498 to decision block 500 where a test is made to determine if $FiO_2$ Set is greater than $FiO_2$ Set Last Before Signal Lost. If the outcomes of decision blocks 498 and 500 are both true, the logic moves to block 502 where $FiO_2$ Set is set to $FiO_2$ Set Last Before Signal Lost. If the outcome of decision block 498 is true, the logic proceeds to decision block 504 where a test is made to determine if $FiO_2$ Set is greater than $FiO_2$ Base. If so, the logic moves to block 506 where $FiO_2$ Set is set to $FiO_2$ Base.

Regardless of the outcome of decision block 498, the logic proceeds to decision block 508 where a test is made to determine if $SpO_2$ Hyperoxemia Counter is less than or equal to Wean Interval (e.g., 30 seconds). If so, the logic moves to decision block 510 where a test is made to determine if $FiO_2$ Set is greater than $FiO_2$ Base. If so, the logic moves to block 512 where $FiO_2$ Set is decreased according to the following equation:

$$FiO_2 \text{ Set}=FiO_2 \text{ Set}-6.0*(SpO_2 \text{ Read}-SpO_2 \text{ High Limit})*(FiO_2 \text{ Set}/100) \quad (7)$$

The logic proceeds to decision block 514 where a test is made to determine if $SpO_2$ Slope is positive (e.g., greater than zero). If $SpO_2$ Slope is positive, the logic moves to lock 516 where $FiO_2$ is decreased using the following equation:

$$FiO_2 \text{ Set}=FiO_2 \text{ Set}-3.0*\text{absolute }(SpO_2 \text{ Slope})*(FiO_2 \text{ Set}/100) \quad (8)$$

Regardless of the outcome of decision block 514, the logic proceeds to decision block 518 where a test is made to determine if $FiO_2$ Set is less than $FiO_2$ Base. If so, the logic moves to block 520 where $FiO_2$ Set is set to $FiO_2$ Base. Regardless of the outcome of decision blocks 508, 510, 514 and 518, the logic proceeds to decision block 522 where a test is made to determine if $SpO_2$ Hyperoxemia Counter is greater than Wean Interval (e.g., 30 seconds). If so, the logic moves to decision block 524 where a test is made to determine if $SpO_2$ Slope is positive. If so, the logic moves to block 526 where $FiO_2$ Set is decreased using the following equation:

$$FiO_2 \text{ Set}=FiO_2 \text{ Set}-\text{absolute }(SpO_2 \text{ Slope})*(FiO_2 \text{ Base}/100) \quad (9)$$

Regardless of the outcome of decision block 524, the logic proceeds to block 528 where Hyperoxemia Adjust Interval Counter is incremented and Hyperoxemia Adjust Interval is calculated using the following equation:

$$\text{Hyperoxemia Adjust Interval}=40.0-3.0*(SpO_2 \text{ Read}-SpO_2 \text{ High Limit}) \quad (10)$$

Hyperoxemia Adjust Interval is limited to a specific range. The logic proceeds to decision block 529 where a test is made to determine if Hyperoxemia Adjust Interval is greater than $SpO_2$ High Adjust Interval High Limit (e.g., 60 seconds). If so, the logic moves to block 530 where Hyperoxemia Adjust Interval is set to $SpO_2$ High Adjust Interval High Limit, (e.g., 60 seconds). Next, the logic moves to decision block 531 where a test is made to determine if Hyperoxemia Adjust Interval is less than $SpO_2$ High Adjust Interval Low Limit (e.g., 20 seconds). If so, the logic moves to block 532 where Hyperoxemia Adjust Interval is set to $SpO_2$ High Adjust Interval Low Limit (e.g., 20 seconds). The logic then moves to decision block 534 where a test is made to determine whether it is time to adjust (i.e., whether the Hyperoxemia Adjust Interval Counter is greater than or equal to Hyperoxemia Adjust Interval). If it is time to adjust, the logic moves to block 536 where $SpO_2$ High Adjust Level is calculated as the average of the $SpO_2$ over the Hyperoxemia Adjust Interval. Next, the logic moves to block 538 where Hyperoxemia Adjust Interval Counter is reset to zero and $FiO_2$ is decreased based on the following equation:

$$FiO_2 \text{ Set}=FiO_2 \text{ Set}-2.0*(SpO_2 \text{ High Adjust Level}-SpO_2 \text{ High Limit})*(FiO_2 \text{ Base}/100) \quad (11)$$

The logic of FIG. 16 then ends and processing returns to FIG. 14.

FIG. 17 illustrates exemplary logic for performing $FiO_2$ Set Determination in Normoxemia in accordance with the present invention. If the $SpO_2$ signal was lost (OUT) and when recovered it shows values in normoxemia and $FiO_2$ Set is greater than the $FiO_2$ Set value that was last recorded when $SpO_2$ dropped out, the $FiO_2$ Set value is changed to that recorded value. This new $FiO_2$ Set value should not exceed the $FiO_2$ Base level. When $SpO_2$ Read values reach the normoxemic range after recovering from hypoxemia while the current $FiO_2$ Set value is above the $FiO_2$ Set Base level and the $SpO_2$ Slope does not show a decrease (is not negative), the algorithm decreases the $FiO_2$ Set value (one time). The $FiO_2$ Set value is not weaned down below the $FiO_2$ Base level. When $SpO_2$ Read values fall in the lower half of the normoxemic range (between the low limit of the target range of normoxemia and the default mid-value $SpO_2$ Base) and it shows signs of worsening (negative $SpO_2$ Slope), the $FiO_2$ Set value is increased in proportion to $SpO_2$ slope and the $FiO_2$ Base level. This is done to avert any onset of hypoxemia. When $SpO_2$ Read values reach the normoxemic range, the algorithm allows for weaning of $FiO_2$ Set every second during a wean interval (e.g., 45 seconds). This weaning occurs if the current $FiO_2$ Set value is above the $FiO_2$ Base level and the $SpO_2$ Slope is positive (towards hyperoxemia). The reduction is proportional to the slope. If the current $FiO_2$ Set value is above the $FiO_2$ Base level but the $SpO_2$ Slope is flat, the reduction is proportional only to the actual $FiO_2$ Set value. Under both conditions, the $FiO_2$ Set value is not weaned down below the $FiO_2$ Base level.

Once $SpO_2$ read values have been in the normoxemic range longer than initial wean interval (e.g., 45 seconds) and the current $FiO_2$ Set value is greater than the $FiO_2$ Base level and there is a positive $SpO_2$ Slope, the $FiO_2$ Set value is decreased (every second) in proportion to the slope and actual $FiO_2$ Set value. $FiO_2$ Set value is not weaned down below the $FiO_2$ Base level. After the initial wean interval (e.g., 45 seconds) has elapsed and the $FiO_2$ Set value is less than the $FiO_2$ Base level and there is a negative $SpO_2$ Slope and the $FiO_2$ Set value is increased in proportion to the $SpO_2$ Slope and the current $FiO_2$ Set level. This increase cannot cause the $FiO_2$ Set level to be above the $FiO_2$ Base level.

Once $SpO_2$ Read values have been in the normoxemic range longer than the initial wean interval (e.g., 45 seconds)

or previous $SpO_2$ level was hyperoxemia or normoxemia and $SpO_2$ was lost and recovered (even before the initial wean interval of 45 seconds in both cases) the algorithm averages $SpO_2$ Read values. The duration of these averaging intervals is in proportion to the departure of $SpO_2$ Read from the mid-point of normoxemia (e.g., $SpO_2$ Base=94%). If the average $SpO_2$ adjust value exceeds the $SpO_2$ Base level (e.g., 94%) and $FiO_2$ Set value is greater than the $FiO_2$ Base level, $FiO_2$ Set value is decreased in proportion to the difference of averaged to base $SpO_2$ and $FiO_2$ Base level. If the averaged $SpO_2$ adjust value is below the $SpO_2$ Base level (e.g., 94%) and $FiO_2$ Set value is less than the $FiO_2$ Base level, $FiO_2$ Set value is increased in proportion to the difference of averaged to base $SpO_2$ and $FiO_2$ Base level. The magnitude of the $FiO_2$ Set change is larger when the average $SpO_2$ is above the mid $SpO_2$ Base and $FiO_2$ Set is above $FiO_2$ Base than when the average $SpO_2$ is below the mid $SpO_2$ Base and $FiO_2$ Set is below $FiO_2$ Base. The purpose of this difference is to allow lower $O_2$, provided that $SpO_2$ is within normoxemia.

The logic of FIG. 17 moves from a start block to decision block 540 where a test is made to determine if $SpO_2$ Signal was OUT and recovered in Normoxemia. If so, the logic moves to decision block 542 where a test is made to determine if $FiO_2$ Set is greater than $FiO_2$ Before Signal Lost. If so, the logic moves to block 544 where $FiO_2$ Set is set to $FiO_2$ Before Signal Lost. Regardless of the outcome of decision block 542, the logic proceeds to decision block 546 where a test is made to determine if $FiO_2$ Set is greater than $FiO_2$ Base. If so, the logic proceeds to block 548 where $FiO_2$ Set is set to $FiO_2$ Base. Regardless of the outcome of decision block 540, the logic proceeds to decision block 550 where a test is made to determine if conditions for initial $FiO_2$ decrease are present. In exemplary embodiments of the invention, conditions for initial $FiO_2$ decrease when $SpO_2$ just crossed the low limit of the target range recovering from hypoxemia are:

$SpO_2$ Normoxemia Counter=Min Time in Range (e.g., 3 seconds)
AND
$SpO_2$ was previously in Hypoxemia
AND
$FiO_2$ Set>$FiO_2$ Base
AND
$SpO_2$ Slope is flat (zero) or positive.

If conditions for initial $FiO_2$ decrease are present, the logic moves from decision block 550 to block 552 where $FiO_2$ Set is decreased using the following equation:

$$FiO_2 \text{ Set}=FiO_2 \text{ Set}-6.0*(SpO_2 \text{ Read}-SpO_2 \text{ Low Limit})*(FiO_2 \text{ Set}/100) \quad (12)$$

The logic then moves to decision block 554 where a test is made to determine if $FiO_2$ Set is less than $FiO_2$ Base. If so, the logic moves to block 556 where $FiO_2$ Set is set to $FiO_2$ Base. Regardless of the outcome of decision block 550, the logic proceeds to decision block 558 where a test is made to determine if $SpO_2$ Read is less than $SpO_2$ Base and $SpO_2$ Slope is negative. If so, the logic moves to block 560 where $FiO_2$ Set is increased according to the following equation:

$$FiO_2 \text{ Set}=FiO_2 \text{ Set}+3.0*\text{absolute }(SpO_2 \text{ Slope})*(FiO_2 \text{ Base}/100) \quad (13)$$

Regardless of the outcome of decision block 558, the logic proceeds to decision block 562 where a test is made to determine if $SpO_2$ Normoxemia Counter is less than or equal to Wean interval (e.g., 45 seconds) If so, the logic moves to decision block 564 where a test is made to determine if $FiO_2$ Set is greater than $FiO_2$ Base. If so, $FiO_2$ may be decreased based on the slope. If $SpO_2$ Slope is positive (yes in decision block 566), the logic moves to block 568 where $FiO_2$ Set is decreased using the following equation:

$$FiO_2 \text{ Set}=FiO_2 \text{ Set}-3.0*\text{absolute }(SpO_2 \text{ Slope})*(FiO_2 \text{ Set}/100) \quad (14)$$

If $SpO_2$ Slope is flat, i.e., zero (yes in decision block 570), the logic moves to block 572 where $FiO_2$ is decreased using the following equation:

$$FiO_2 \text{ Set}=FiO_2 \text{ Set}-3.0*(FiO_2 \text{ Set}/100) \quad (15)$$

The logic then moves to decision block 574 where a test is made to determine if $FiO_2$ Set is less than $FiO_2$ Base. If so, the logic moves to block 576 where $FiO_2$ Set is set to $FiO_2$ Base.

Regardless of the outcome of decision block 562, the logic proceeds to decision block 578 where a test is made to determine if $SpO_2$ Normoxemia Counter is greater than Wean Interval (e.g., 45 seconds). If so, the logic moves to decision block 580 where a test is made to determine if $SpO_2$ Slope is greater than zero and $FiO_2$ Set is greater than $FiO_2$ Base. If so, the logic moves to block 582 where $FiO_2$ Set is decreased using the following equation:

$$FiO_2 \text{ Set}=FiO_2 \text{ Set}-3.0*\text{absolute }(SpO_2 \text{ Slope})*(FiO_2 \text{ Set}/100) \quad (16)$$

The logic then moves to decision block 584 where a test is made to determine if $FiO_2$ Set is less than $FiO_2$ Base. If so, the logic moves to block 586 where $FiO_2$ Set is set to $FiO_2$ Base.

Regardless of the outcome of decision block 578, the logic proceeds to decision block 588 where a test is made to determine if $SpO_2$ Normoxemia Counter is greater than Wean Interval (e.g., 45 seconds). If so, the logic moves to decision block 590 where a test is made to determine if $SpO_2$ Slope is greater than zero and $FiO_2$ Set is less than $FiO_2$ Base. If so, the logic moves to block 592 where $FiO_2$ Set is increased using the following equation:

$$FiO_2 \text{ Set}=FiO_2 \text{ Set}+3.0*\text{absolute }(SpO_2 \text{ Slope})*(FiO_2 \text{ Set}/100) \quad (17)$$

The logic then moves to decision block 594 where a test is made to determine if $FiO_2$ Set is greater than $FiO_2$ Base. If so, the logic moves to block 596 where $FiO_2$ Set is set to $FiO_2$ Base.

Regardless of the outcome of decision block 588, the logic proceeds to decision block 598 where a test is made to determine if $SpO_2$ Counter is greater than Wean interval (e.g. 45 seconds) or if the previous level is Hyperoxemia or Normoxemia. If so, the logic moves to block 600 where Normoxemia Adjust Interval Counter is incremented and Normoxemia Adjust Level is calculated using the following equation:

$$\text{Normoxemia Adjust Interval}=60.0-4.0*\text{absolute }(SpO_2 \text{ Read}-SpO_2 \text{ Base}) \quad (18)$$

Normoxemia Adjust Interval is limited to a specific range. The logic moves to decision block 601 where a test is made to determine if Normoxemia Adjust Interval is greater than $SpO_2$ Normal Adjust Interval High Limit (e.g., 60 seconds).

If so, the logic moves to block 602 where Normoxemia Adjust Interval is set to SpO₂ Normal Adjust Interval High Limit (e.g., 60 seconds). Next, the logic moves to decision block 604 where a test is made to determine if Normoxemia Adjust Interval is less than SpO₂ Normal Adjust Interval Low Limit (e.g., 20 seconds). If so, the logic moves to block 606 where Normoxemia Adjust Interval is set to SpO₂ Normal Adjust Interval Low Limit (e.g., 20 seconds). The logic then moves to decision block 608 where a test is made to determine if it is time to adjust (i.e., Normoxemia Adjust Interval Counter is greater than or equal to Normoxemia Adjust Interval). If so, the logic moves to block 610 where SpO₂ Normoxemia Adjust Level is calculated as the average of the SpO₂ over the Normoxemia Interval. Next, the logic moves to decision block 612 where a test is made to determine if SpO₂ Adjust Level is greater than SpO₂ Base AND SpO₂ Slope is greater than or equal to zero AND FiO₂ Set is greater than FiO₂ Base. If so, the logic moves to block 614 where Normoxemia Adjust Interval Counter is reset to zero and FiO₂ Set is decreased using the following equation:

$$\text{FiO}_2 \text{ Set} = \text{FiO}_2 \text{ Set} - 2.0*(\text{SpO}_2 \text{ Adjust Level} - \text{SpO}_2 \text{ Base})*(\text{FiO}_2 \text{ Base}/100) \quad (19)$$

The logic then moves to decision block 616 where a test is made to determine if SpO₂ Adjust Level is less than SpO₂ Base AND SpO₂ Slope is less than or equal to zero AND FiO₂ Set is less than FiO₂ Base. If so, the logic moves to block 618 where FiO₂ Set is increased using the following equation:

$$\text{FiO}_2 \text{ Set} = \text{FiO}_2 \text{ Set} + (\text{SpO}_2 \text{ Base} - \text{SpO}_2 \text{ Adjust Level})*(\text{FiO}_2 \text{ Base}/100) \quad (20)$$

The logic of FIG. 17 then ends and processing returns to FIG. 14.

Returning to FIG. 14, after the appropriate processing has been performed based on the SpO₂ level (hypoxemia in block 452, hyperoxemia in block 454 or normoxemia in block 456), the logic of FIG. 14 ends and processing returns to FIG. 8.

Returning to FIG. 8, if closed-loop control is not enabled (no in decision block 272), the logic moves to block 274 where FiO₂ Set is set to FiO₂ Backup. Next, the logic moves to block 276 where the user is alerted. Regardless of whether closed-loop control is enabled (decision block 272), the logic proceeds to decision block 278 where a test is made to determine if FiO₂ Base Calc is enabled. If so, the logic moves to block 280 where FiO₂ Base Determination is performed as shown in detail in FIG. 18 and described next.

FIG. 18 illustrates in detail exemplary logic for performing FiO₂ Base Determination in accordance with the present invention. When FiO₂ Base Calc is enabled, the algorithm automatically updates the basal oxygen when specific conditions are met as shown in FIG. 18. In exemplary embodiments, when FiO₂ Base Calc is enabled by the user, the algorithm averages five minutes (not necessarily continuous) worth of FiO₂ Set values occurring during specific conditions. The calculated average for FiO₂ Base is limited to +/−10% of the current FiO₂ Base value. The newly calculated FiO₂ Base value is averaged with the current FiO₂ Base value. The resulting value is the new FiO₂ Base value. The average interval duration is five minutes. This parameter can be modified according to the patient condition, either as a system default, by the user or automatically.

The logic of FIG. 18 moves from a start block to decision block 620 where a test is made to determine if there are conditions for FiO₂ Base. Exemplary conditions for inclusion of current FiO₂ Set value in FiO₂ base determination are:

SpO₂ in Normoxemia AND SpO₂ Normoxemia Counter>SpO₂ Normoxemia Base Min (e.g., 30 sec)

OR

SpO₂ in Hyperoxemia AND FiO₂ Set=FiO₂ Min AND FiO₂ Min Counter>FiO₂ Base Min (e.g., 30 sec)

OR

SpO₂ in Hypoxemia AND FiO₂ Set=FiO₂ Max AND FiO₂ Max Counter>FiO₂ Base Max (e.g., 60 sec)

OR

SpO₂ in Hyperoxemia AND FiO₂ Set<FiO₂ Base AND SpO₂ Hyperoxemia Counter>SpO₂ High wean interval (e.g., 30 sec)

OR

SpO₂ in Hypoxemia AND FiO₂ Set>FiO₂ Base AND SpO₂ Hypoxemia Counter>SpO₂ Low Alarm Limit (e.g., 60 sec).

In exemplary embodiments, at least one of the following conditions must be met to include a specific FiO₂ value in the calculation of FiO₂ base:

(1) Current SpO₂ should be in normoxemia and SpO₂ has been in normoxemia for at last 30 seconds (base min);

(2) Current SpO₂ should be in hyperoxemia and FiO₂ is at the FiO₂ minimum level and FiO₂ has been at the minimum FiO₂ level for at least 30 seconds (base min);

(3) Current SpO₂ should be in hypoxemia and FiO₂ is at the FiO₂ max level and FiO₂ has been at the max FiO₂ level for at least 60 seconds (base max);

(4) Current SpO₂ in Hyperoxemia and current FiO₂ is below FiO₂ base and SpO₂ has been in hyperoxemia longer than 30 seconds; or (5) Current SpO₂ in Hypoxemia and current FiO₂ is above FiO₂ Base and SpO₂ has been in hypoxemia longer than 60 seconds.

If conditions for FiO₂ base exist, the logic moves to block 622 where FiO₂ Base Counter is incremented using the following equation:

$$\text{FiO}_2 \text{ Base} = \text{FiO}_2 \text{ Base} + \text{FiO}_2 \text{ Set} \quad (21)$$

Regardless of the outcome of decision block 620, the logic proceeds to decision block 624 where a test is made to determine if there are 5 minutes (or whatever value is specified) of FiO₂ data. If so, the logic moves to block 626 where FiO₂ Base is averaged and set to be within the specified limit (e.g., +/−10%) of the current FiO₂ Base. FiO₂ Base Counter is reset to zero. The logic then moves to block 628 where the new and current FiO₂ Base values are averaged and set to be within the Max and Min settings. The logic of FIG. 18 then ends and processing returns to FIG. 8.

Returning to FIG. 8, regardless of whether FiO₂ Base Calc is enabled (decision block 278), the logic proceeds to block 282 where FiO₂ Set checking is performed as shown in detail in FIG. 19 and described next.

Figure 19:
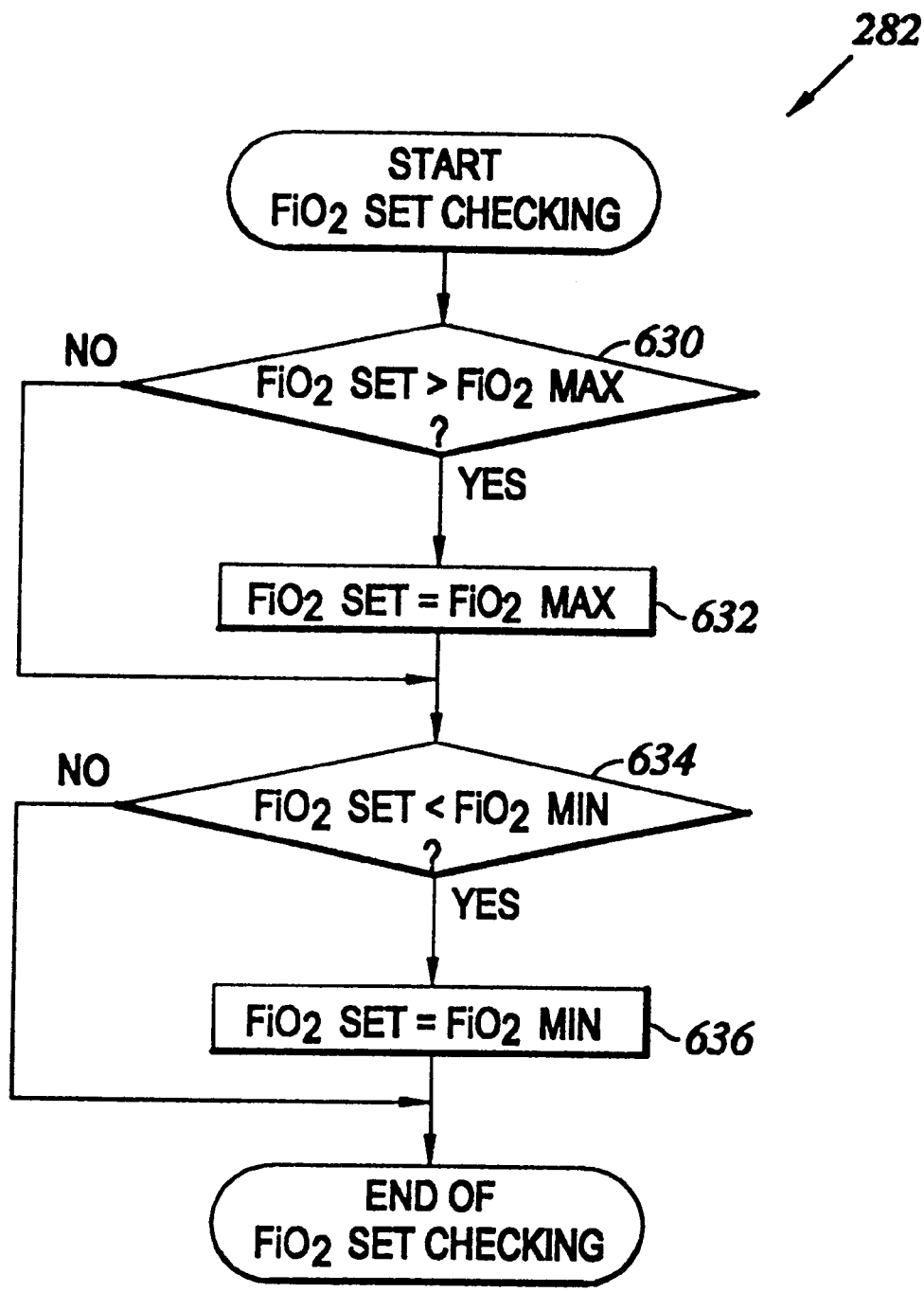

FIG. 19 illustrates exemplary logic for performing FiO₂ Set checking in accordance with the present invention. The logic of FIG. 19 ensures that FiO₂ Set is within the allowable range. If it is determined in decision block 630 that FiO₂ Set is greater than FiO₂ Max, FiO₂ Set is set to FiO₂ Max in block 632. If it is determined in decision block 634 that FiO₂ Set is less than FiO₂ Min, FiO₂ Set is set to FiO₂ Min in block 636. The logic of FIG. 19 then ends and processing returns to FIG. 8.

Returning to FIG. 8, the logic proceeds to block 284 where FiO₂ Base/Backup checking is performed as shown in detail in FIG. 20 and described next.

Figure 20:
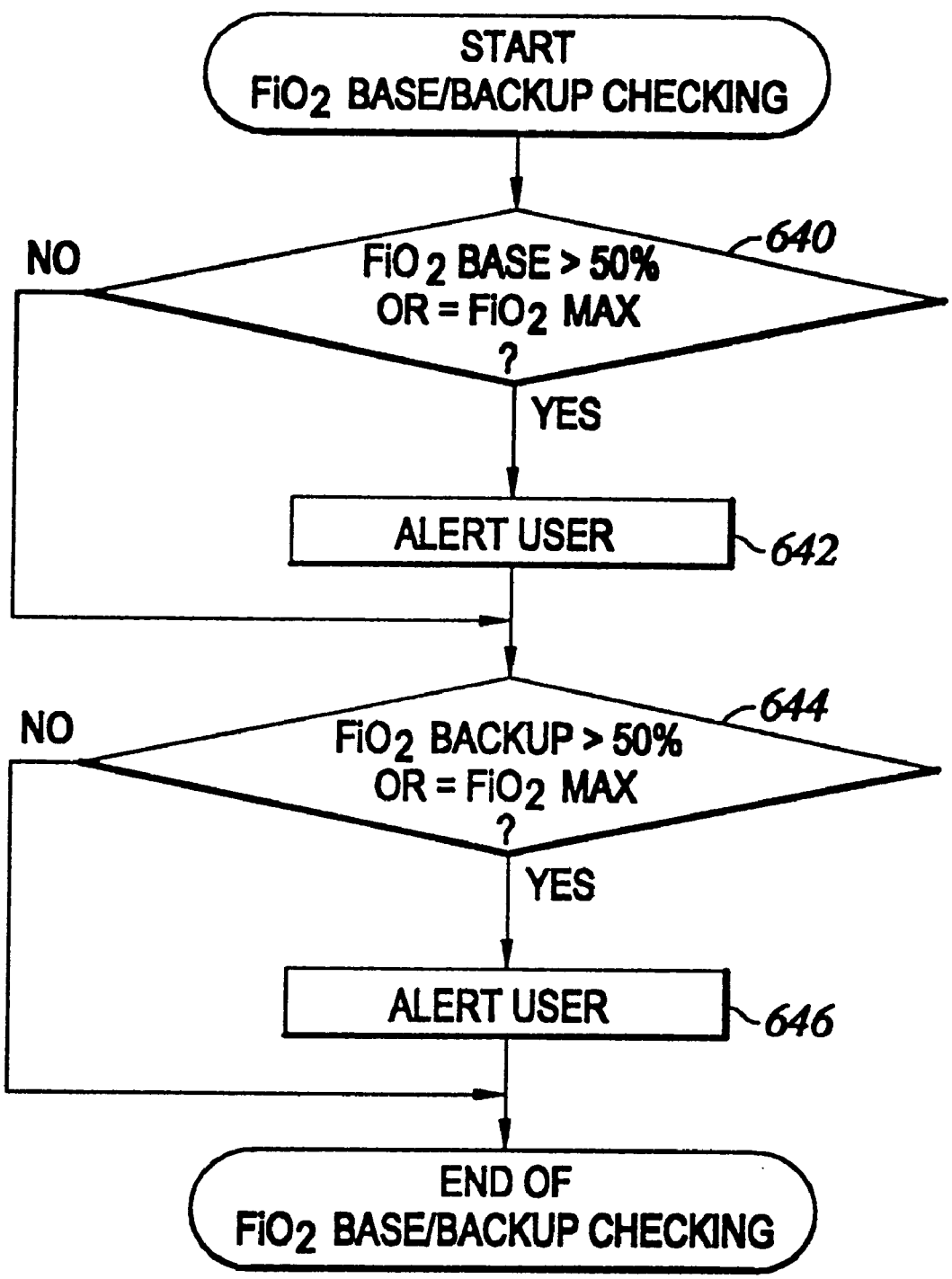

FIG. 20 illustrates exemplary logic for performing $FiO_2$ Base/Backup checking in accordance with the present invention. New $FiO_2$ Base and Backup values determined by the algorithm or set by the user are checked to ensure that they fall within the minimum and maximum ranges. If they don't, the user is alerted. In exemplary embodiments, if the value is not within acceptable limits, the value is set to an appropriate value. The logic of FIG. 20 alerts the user (block 642) if it is determined that $FiO_2$ Base is greater than 50% or if $FiO_2$ Base is equal to $FiO_2$ Max as determined in decision block 640.

Similarly, if it is determined in decision block 644 that $FiO_2$ Backup is greater than 50% or $FiO_2$ Backup is equal to $FiO_2$ Max, the user is alerted in block 646. The logic of FIG. 20 then ends and processing returns to FIG. 8.

Returning to FIG. 8, the logic then proceeds to block 286 where $FiO_2$ Set Output Control to Mixer. Once the new $FiO_2$ value is confirmed, the updated $FiO_2$ Set value should be passed to the output routine that controls the air-oxygen blender. In exemplary embodiments, the output routine outputs a specific voltage to drive an external blender. In various embodiments, additional monitoring is provided to ensure correct mixing by monitoring data from a built-in $FiO_2$ analyzer. The logic of FIG. 8 then ends and processing returns to FIG. 6.

FIG. 21 illustrates an exemplary graphical user interface 700. The exemplary user interface 700 shown in FIG. 21 displays $SpO_2$ and $FiO_2$ parameters over a period of time. In an exemplary embodiment, the last five minutes and thirty minutes of data are displayed simultaneously. It will be appreciated that various other user displays are possible, for example in alternate embodiments, the user can select the time interval(s) for display data. The user interface also allows the user to interactively change various parameters. More specifically, the exemplary user interface 700 shown in FIG. 21 displays:

the current $SpO_2$ value read by the oximeter 702;

five minutes of tracing of $SpO_2$ at 60 second divisions 704;

the current $FiO_2$ set at the blender 706;

five minutes of tracing of $FiO_2$ Set values at 60 second divisions 708;

30 minutes of tracing of $SpO_2$ Read and $FiO_2$ Set values at five minute divisions 710;

the $SpO_2$ level (e.g., 0=normoxemia, 1=hypoxemia and 2=hyperoxemia) 712;

the previous $SpO_2$ level 714;

the calculated $SpO_2$ Slope 716;

the calculated $SpO_2$ trend based on $SpO_2$ slope magnitude 718;

an $SpO_2$ high counter (hyperoxemia) 720;

an $SpO_2$ normal counter (normoxemia) 722;

an $SpO_2$ low counter (hypoxemia) 724;

an $SpO_2$ low counter for the range of 85%–the low $SpO_2$ limit 726;

an $SpO_2$ low counter for the range of 75%–85% 728;

an $SpO_2$ low counter for the range of less than 75% 730;

an $SpO_2$ High Limit of the target range 732;

an $SpO_2$ Low Limit of the target range 734;

an $SpO_2$ signal OK counter 736;

an $SpO_2$ signal OUT counter 738;

a control button 744 which is the main switch to start closed loop adjustments (i.e., when OFF, $FiO_2$ is at backup level);

a record button 746 which is used to record certain parameters (e.g., write to a file);

an $FiO_2$ Base Cal switch 750 which is switched on and off to calculate the basal oxygen requirement;

the $FiO_2$ Base value 752;

a $FiO_2$ Base counter 754 which is used when $FiO_2$ Base Calc is enabled;

an $FiO_2$ backup value 756; and an $FiO_2$ Minimum level 758.

As discussed earlier, the user can modify various parameters at any time. For example, in the exemplary embodiment shown in FIG. 21, the user can use the arrows to modify the values for the associated parameters.

Additional modifications and improvements of the present invention may also be apparent to those of ordinary skill in the art. Thus, the particular parts described and illustrated herein is intended to represent only one embodiment of the present invention, and is not intended to serve as limitations of alternative devices within the spirit and scope of the invention.

What is claimed is:

1. A method for adjusting fractionally inspired oxygen delivery to a patient in response to receiving an arterial hemoglobin oxygen saturation signal, said method comprising:

a. specifying a plurality of hemoglobin oxygen saturation levels;
   b. reading the arterial hemoglobin oxygen saturation signal;
   c. determining if the arterial hemoglobin oxygen saturation signal is a valid signal;
   d. if the hemoglobin oxygen saturation signal is a not a valid signal, determining a value for the fractionally inspired oxygen delivery to the patient based on backup value;
   e. if the hemoglobin oxygen saturation signal is a valid signal,
      i. determining the hemoglobin oxygen saturation level based on the arterial hemoglobin oxygen saturation signal;
      ii. determining a trend by calculating a slope using a plurality of recent hemoglobin oxygen saturation signals;
      iii. if a closed loop mode is enabled, determining the fractionally inspired oxygen to deliver to the patient based on the hemoglobin oxygen saturation level and the trend;
      iv. if the closed loop mode is not enabled, determining the fractionally inspired oxygen to deliver to the patient based on the backup value; and
   f. delivering the fractionally inspired oxygen to the patient.

2. The method of claim 1, wherein the fractionally inspired oxygen is continuously delivered to the patient by repeating b–f.

3. The method of claim 1, further comprising providing a user interface.

4. The method of claim 3, wherein the user interface provides a status display.

5. The method of claim 3, wherein the user interface allows the user to update a plurality of settings.

6. The method according to claim 3, wherein the user interface displays a user alert.

7. The method of claim 1, wherein specifying the plurality of hemoglobin oxygen saturation levels further comprises:
 a. specifying a normoxemic target range;
 b. specifying a hyperoxemic range; and
 c. specifying a hypoxemic range.

8. The method of claim 7, wherein determining the fractionally inspired oxygen to deliver to the patient comprises increasing the amount of fractionally inspired oxygen delivered to the patient in response to receiving an arterial oxygen-hemoglobin oxygen saturation signal value less than the normoxemic target range for a specified amount of time.

9. The method of claim 7, wherein determining the fractionally inspired oxygen to deliver to the patient comprises decreasing the amount of fractionally inspired oxygen delivered to the patient in response to receiving an arterial oxygen-hemoglobin oxygen saturation signal value greater than the normoxemic target range for a specified amount of time.

10. The method of claim 1, wherein determining the backup value for the fractionally inspired oxygen delivery to the patient comprises maintaining the amount of fractionally inspired oxygen delivered to the patient until the signal is restored.

11. The method according to claim 1, further comprising calculating a plurality of slopes simultaneously.

12. The method according to claim 1, further comprising weaning the fractionally inspired oxygen delivered to the patient.

13. The method according to claim 1, wherein the closed loop mode is user selectable.

14. A computer readable medium having an executable component for adjusting fractionally inspired oxygen delivery for a patient in response to receiving an arterial hemoglobin oxygen saturation signal, wherein the executable component contains computer-executable instruction for:
 a. specifying a plurality of hemoglobin oxygen saturation levels;
 b. reading the arterial hemoglobin oxygen saturation signal;
 c. determining if the arterial hemoglobin oxygen saturation signal is a valid signal;
 d. if the hemoglobin oxygen saturation signal is a not a valid signal, determining a value for the fractionally inspired oxygen delivery to the patient based on backup value;
 e. if the hemoglobin oxygen saturation signal is a valid signal,
  i. determining the hemoglobin oxygen saturation level based on the arterial hemoglobin oxygen saturation signal;
  ii. determining a trend by calculating a slope using a plurality of recent hemoglobin oxygen saturation signals;
  iii. if a closed loop mode is enabled, determining the fractionally inspired oxygen to deliver to the patient based on the hemoglobin oxygen saturation level and the trend;
  iv. if the closed loop mode is not enabled, determining the fractionally inspired oxygen to deliver to the patient based on the backup value; and
 f. delivering the fractionally inspired oxygen to the patient.

* * * * *